US008162987B2

(12) United States Patent
Zucherman et al.

(10) Patent No.: US 8,162,987 B2
(45) Date of Patent: Apr. 24, 2012

(54) MODULAR SPINE TREATMENT KIT FOR DYNAMIC STABILIZATION AND MOTION PRESERVATION OF THE SPINE

(75) Inventors: James F. Zucherman, San Francisco, CA (US); Ken Y. Hsu, San Francisco, CA (US); Charles J. Winslow, Walnut Creek, CA (US); Henry A. Klyce, Piedmont, CA (US); Donald L. Cain, Oakland, CA (US); H. Adam Klyce, Berkeley, CA (US); John J. Flynn, Walnut Creek, CA (US); Jay A. Markwart, Castro Valley, CA (US)

(73) Assignee: Spartek Medical, Inc., Concord, CA (US)

( * ) Notice: Subject to any disclaimer, the term of this patent is extended or adjusted under 35 U.S.C. 154(b) by 1294 days.

(21) Appl. No.: 11/832,527

(22) Filed: Aug. 1, 2007

(65) Prior Publication Data

US 2008/0306521 A1    Dec. 11, 2008

Related U.S. Application Data

(60) Provisional application No. 60/942,162, filed on Jun. 5, 2007.

(51) Int. Cl.
    *A61B 17/70* (2006.01)
(52) U.S. Cl. ...................................... 606/264
(58) Field of Classification Search .............. 606/246, 606/264–268, 270, 272, 273, 279, 301, 305, 606/308, 328; 411/393; 403/362, 150
See application file for complete search history.

(56) References Cited

U.S. PATENT DOCUMENTS

| | | |
|---|---|---|
| 4,041,939 A | 8/1977 | Hall |
| 4,065,817 A | 1/1978 | Branemark et al. |
| 4,347,845 A | 9/1982 | Mayfield |
| 4,369,770 A | 1/1983 | Bacal et al. |
| 4,382,438 A | 5/1983 | Jacobs |
| 4,409,968 A | 10/1983 | Drummond |
| 4,411,259 A | 10/1983 | Drummond |
| 4,422,451 A | 12/1983 | Kalamchi |
| 4,479,491 A | 10/1984 | Martin |
| 4,567,885 A | 2/1986 | Androphy |
| 4,573,454 A | 3/1986 | Hoffman |
| 4,604,995 A | 8/1986 | Stephens et al. |
| 4,611,580 A | 9/1986 | Wu |

(Continued)

FOREIGN PATENT DOCUMENTS

DE    2649042 B1    10/1976

(Continued)

OTHER PUBLICATIONS

International Search Report for PCT/US/08/65443 dated Sep. 16, 2008, 4 pages.

(Continued)

*Primary Examiner* — Eduardo C Robert
*Assistant Examiner* — David Comstock
(74) *Attorney, Agent, or Firm* — Fliesler Meyer LLP

(57) ABSTRACT

A dynamic stabilization, motion preservation spinal implant system includes an anchor system, a horizontal rod system and a vertical rod system. The systems are modular so that various constructs and configurations can be created and customized to a patient.

24 Claims, 39 Drawing Sheets

U.S. PATENT DOCUMENTS

| | | | |
|---|---|---|---|
| 4,611,581 A | 9/1986 | Steffee | |
| 4,611,582 A | 9/1986 | Duff | |
| 4,641,636 A | 2/1987 | Cotrel | |
| 4,648,388 A | 3/1987 | Steffee | |
| 4,653,481 A | 3/1987 | Howland et al. | |
| 4,653,489 A | 3/1987 | Tronzo | |
| 4,655,199 A | 4/1987 | Steffee | |
| 4,658,809 A | 4/1987 | Ulrich et al. | |
| 4,696,290 A | 9/1987 | Steffee | |
| 4,719,905 A | 1/1988 | Steffee | |
| 4,763,644 A | 8/1988 | Webb | |
| 4,773,402 A | 9/1988 | Asher et al. | |
| 4,805,602 A | 2/1989 | Puno et al. | |
| 4,815,453 A | 3/1989 | Cotrel | |
| 4,887,595 A | 12/1989 | Heinig et al. | |
| 4,913,134 A | 4/1990 | Luque | |
| 4,946,458 A | 8/1990 | Harms et al. | |
| 4,950,269 A | 8/1990 | Gaines, Jr. | |
| 4,955,885 A | 9/1990 | Meyers | |
| 4,987,892 A | 1/1991 | Krag et al. | |
| 5,005,562 A | 4/1991 | Cotrel | |
| 5,024,213 A | 6/1991 | Asher et al. | |
| 5,030,220 A | 7/1991 | Howland | |
| 5,042,982 A | 8/1991 | Harms et al. | |
| 5,047,029 A | 9/1991 | Aebi et al. | |
| 5,067,955 A | 11/1991 | Cotrel | |
| 5,074,864 A | 12/1991 | Cozad et al. | |
| 5,084,049 A | 1/1992 | Asher et al. | |
| 5,092,866 A | 3/1992 | Breard et al. | |
| 5,102,412 A | 4/1992 | Rogozinski | |
| 5,112,332 A | 5/1992 | Cozad et al. | |
| 5,113,685 A | 5/1992 | Asher et al. | |
| 5,127,912 A | 7/1992 | Ray et al. | |
| 5,129,388 A | 7/1992 | Vignaud et al. | |
| 5,129,900 A | 7/1992 | Asher et al. | |
| 5,147,359 A | 9/1992 | Cozad et al. | |
| 5,154,718 A | 10/1992 | Cozad et al. | |
| 5,176,680 A | 1/1993 | Vignaud et al. | |
| 5,180,393 A | 1/1993 | Commarmond | |
| 5,190,543 A | 3/1993 | Schläpfer | |
| 5,201,734 A | 4/1993 | Cozad et al. | |
| 5,207,678 A | 5/1993 | Harms et al. | |
| 5,261,911 A | 11/1993 | Carl | |
| 5,261,912 A | 11/1993 | Frigg | |
| 5,261,913 A | 11/1993 | Marnay | |
| 5,281,222 A | 1/1994 | Allard et al. | |
| 5,282,801 A | 2/1994 | Sherman | |
| 5,282,863 A | 2/1994 | Burton | |
| 5,290,289 A | 3/1994 | Sanders et al. | |
| 5,312,402 A | 5/1994 | Schläpfer et al. | |
| 5,312,404 A | 5/1994 | Asher et al. | |
| 5,344,422 A | 9/1994 | Frigg | |
| 5,346,493 A | 9/1994 | Stahurski et al. | |
| 5,360,429 A | 11/1994 | Jeanson et al. | |
| 5,360,431 A | 11/1994 | Puno et al. | |
| 5,380,325 A | 1/1995 | Lahille et al. | |
| 5,380,326 A | 1/1995 | Lin | |
| 5,382,248 A | 1/1995 | Jacobson et al. | |
| 5,385,583 A | 1/1995 | Cotrel | |
| 5,387,213 A | 2/1995 | Breard et al. | |
| 5,415,661 A | 5/1995 | Holmes | |
| 5,429,639 A | 7/1995 | Judet | |
| 5,437,671 A * | 8/1995 | Lozier et al. | 606/252 |
| 5,437,672 A | 8/1995 | Alleyne | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,487,742 A | 1/1996 | Cotrel | |
| 5,496,321 A | 3/1996 | Puno et al. | |
| 5,498,264 A | 3/1996 | Schlapfer et al. | |
| 5,520,689 A | 5/1996 | Schläpfer et al. | |
| 5,534,001 A | 7/1996 | Schlapfer et al. | |
| 5,536,268 A | 7/1996 | Griss | |
| 5,540,688 A | 7/1996 | Navas | |
| 5,545,167 A | 8/1996 | Lin | |
| 5,549,607 A | 8/1996 | Olson et al. | |
| 5,562,737 A | 10/1996 | Graf | |
| 5,569,248 A | 10/1996 | Mathews | |
| 5,609,592 A | 3/1997 | Brumfield et al. | |
| 5,609,593 A | 3/1997 | Errico et al. | |
| 5,611,800 A | 3/1997 | Davis et al. | |
| 5,624,441 A | 4/1997 | Sherman et al. | |
| 5,628,740 A | 5/1997 | Mullane | |
| 5,630,816 A | 5/1997 | Kambin | |
| 5,643,260 A | 7/1997 | Doherty | |
| 5,645,599 A | 7/1997 | Samani | |
| 5,651,789 A | 7/1997 | Cotrel | |
| 5,653,708 A | 8/1997 | Howland | |
| 5,658,284 A | 8/1997 | Sebastian et al. | |
| 5,667,506 A | 9/1997 | Sutterlin | |
| 5,667,507 A | 9/1997 | Corin et al. | |
| 5,669,910 A | 9/1997 | Korhonen et al. | |
| 5,672,175 A | 9/1997 | Martin | |
| 5,672,176 A | 9/1997 | Biedermann et al. | |
| 5,676,665 A | 10/1997 | Bryan | |
| 5,676,703 A | 10/1997 | Gelbard | |
| 5,681,311 A | 10/1997 | Foley et al. | |
| 5,681,319 A | 10/1997 | Biedermann et al. | |
| 5,683,391 A | 11/1997 | Boyd | |
| 5,683,392 A | 11/1997 | Richelsoph et al. | |
| 5,683,393 A | 11/1997 | Ralph | |
| 5,688,272 A | 11/1997 | Montague et al. | |
| 5,688,273 A | 11/1997 | Errico et al. | |
| 5,690,629 A | 11/1997 | Asher et al. | |
| 5,690,632 A | 11/1997 | Schwartz et al. | |
| 5,690,633 A | 11/1997 | Taylor et al. | |
| 5,693,053 A | 12/1997 | Estes | |
| 5,697,929 A | 12/1997 | Mellinger | |
| 5,700,292 A | 12/1997 | Margulies | |
| 5,702,392 A | 12/1997 | Wu et al. | |
| 5,702,394 A | 12/1997 | Henry et al. | |
| 5,702,395 A | 12/1997 | Hopf | |
| 5,702,396 A | 12/1997 | Hoenig et al. | |
| 5,702,399 A | 12/1997 | Kilpela et al. | |
| 5,702,452 A | 12/1997 | Argenson et al. | |
| 5,713,900 A | 2/1998 | Benzel et al. | |
| 5,713,904 A | 2/1998 | Errico et al. | |
| 5,716,355 A | 2/1998 | Jackson et al. | |
| 5,716,356 A | 2/1998 | Biedermann et al. | |
| 5,716,357 A | 2/1998 | Rogozinski | |
| 5,716,358 A | 2/1998 | Ochoa et al. | |
| 5,716,359 A | 2/1998 | Ojima et al. | |
| 5,720,751 A | 2/1998 | Jackson | |
| 5,725,528 A | 3/1998 | Errico et al. | |
| 5,725,582 A | 3/1998 | Bevan et al. | |
| 5,728,098 A | 3/1998 | Sherman et al. | |
| 5,733,286 A | 3/1998 | Errico et al. | |
| 5,735,851 A | 4/1998 | Errico et al. | |
| 5,741,254 A | 4/1998 | Henry et al. | |
| 5,743,907 A | 4/1998 | Asher et al. | |
| 5,743,911 A | 4/1998 | Cotrel | |
| 5,752,957 A | 5/1998 | Ralph et al. | |
| 5,766,254 A | 6/1998 | Gelbard | |
| 5,776,135 A | 7/1998 | Errico et al. | |
| 5,782,833 A | 7/1998 | Haider | |
| 5,785,711 A | 7/1998 | Errico et al. | |
| 5,797,911 A | 8/1998 | Sherman et al. | |
| 5,800,435 A | 9/1998 | Errico et al. | |
| 5,810,819 A | 9/1998 | Errico et al. | |
| 5,863,293 A | 1/1999 | Richelsoph | |
| 5,879,350 A | 3/1999 | Sherman et al. | |
| 5,885,286 A | 3/1999 | Sherman et al. | |
| 5,891,145 A | 4/1999 | Morrison et al. | |
| 5,899,904 A | 5/1999 | Errico et al. | |
| RE36,221 E | 6/1999 | Breard et al. | |
| 5,910,142 A | 6/1999 | Tatar | |
| 5,925,047 A | 7/1999 | Errico et al. | |
| 5,928,231 A | 7/1999 | Klein et al. | |
| 5,928,232 A | 7/1999 | Howland et al. | |
| 5,928,233 A | 7/1999 | Apfelbaum et al. | |
| 5,947,965 A | 9/1999 | Bryan | |
| 5,947,969 A | 9/1999 | Errico et al. | |
| 5,954,725 A | 9/1999 | Sherman et al. | |
| 5,961,517 A | 10/1999 | Biedermann et al. | |
| 5,964,760 A | 10/1999 | Richelsoph | |
| 5,980,521 A | 11/1999 | Montague et al. | |
| 5,980,523 A | 11/1999 | Jackson | |

| | | | | | | |
|---|---|---|---|---|---|---|
| 5,984,922 A | 11/1999 | McKay | | 6,626,908 B2 | 9/2003 | Cooper et al. |
| 5,989,251 A | 11/1999 | Nichols | | 6,645,207 B2 | 11/2003 | Dixon et al. |
| 5,989,254 A | 11/1999 | Katz | | 6,652,526 B1 | 11/2003 | Arafiles |
| 6,001,098 A | 12/1999 | Metz-Stavenhagen et al. | | 6,656,181 B2 | 12/2003 | Dixon et al. |
| 6,004,322 A | 12/1999 | Bernstein | | 6,660,004 B2 | 12/2003 | Barker et al. |
| 6,010,503 A | 1/2000 | Richelsoph et al. | | 6,660,005 B2 | 12/2003 | Toyama et al. |
| 6,015,409 A | 1/2000 | Jackson | | 6,695,845 B2 | 2/2004 | Dixon et al. |
| 6,036,693 A | 3/2000 | Yuan et al. | | 6,706,045 B2 | 3/2004 | Lin et al. |
| 6,050,997 A | 4/2000 | Mullane | | 6,709,434 B1 | 3/2004 | Gournay et al. |
| 6,053,917 A | 4/2000 | Sherman et al. | | 6,716,213 B2 | 4/2004 | Shitoto |
| 6,063,089 A | 5/2000 | Errico et al. | | 6,716,214 B1 | 4/2004 | Jackson |
| 6,077,262 A | 6/2000 | Schläpfer et al. | | 6,726,689 B2 | 4/2004 | Jackson |
| 6,086,588 A | 7/2000 | Ameil et al. | | 6,736,820 B2 | 5/2004 | Biedermann et al. |
| 6,090,111 A | 7/2000 | Nichols | | 6,740,086 B2 | 5/2004 | Richelsoph |
| 6,096,039 A | 8/2000 | Stoltenberg et al. | | 6,749,614 B2 | 6/2004 | Teitelbaum et al. |
| 6,113,600 A | 9/2000 | Drummond et al. | | 6,752,807 B2 | 6/2004 | Lin et al. |
| 6,113,601 A | 9/2000 | Tatar | | 6,755,829 B1 | 6/2004 | Bono et al. |
| 6,127,597 A | 10/2000 | Beyar et al. | | 6,755,835 B2 | 6/2004 | Schultheiss et al. |
| 6,132,430 A | 10/2000 | Wagner | | 6,761,719 B2 | 7/2004 | Justis et al. |
| 6,132,434 A | 10/2000 | Sherman et al. | | 6,783,526 B1 | 8/2004 | Lin et al. |
| 6,136,000 A | 10/2000 | Louis et al. | | 6,783,527 B2 | 8/2004 | Drewry et al. |
| 6,146,383 A | 11/2000 | Studer et al. | | 6,786,907 B2 | 9/2004 | Lange |
| 6,171,311 B1 | 1/2001 | Richelsoph | | 6,793,656 B1 | 9/2004 | Mathews |
| 6,193,720 B1 | 2/2001 | Yuan et al. | | 6,805,695 B2 | 10/2004 | Keith et al. |
| 6,197,028 B1 | 3/2001 | Ray et al. | | 6,805,714 B2 | 10/2004 | Sutcliffe |
| 6,210,413 B1 | 4/2001 | Justis et al. | | 6,811,567 B2 | 11/2004 | Reiley |
| 6,217,578 B1 | 4/2001 | Crozet et al. | | 6,832,999 B2 | 12/2004 | Ueyama et al. |
| 6,248,106 B1 | 6/2001 | Ferree | | 6,840,940 B2 | 1/2005 | Ralph et al. |
| 6,254,602 B1 | 7/2001 | Justis | | 6,843,791 B2 | 1/2005 | Serhan |
| 6,261,287 B1 | 7/2001 | Metz-Stavenhagen | | 6,852,128 B2 | 2/2005 | Lange |
| 6,273,888 B1 | 8/2001 | Justis | | 6,858,030 B2 | 2/2005 | Martin et al. |
| 6,273,914 B1 | 8/2001 | Papas | | 6,869,433 B2 | 3/2005 | Glascott |
| 6,280,443 B1 | 8/2001 | Gu et al. | | 6,875,211 B2 | 4/2005 | Nichols et al. |
| 6,287,311 B1 | 9/2001 | Sherman et al. | | 6,881,215 B2 | 4/2005 | Assaker et al. |
| 6,293,949 B1 | 9/2001 | Justis et al. | | 6,883,520 B2 | 4/2005 | Lambrecht |
| 6,302,882 B1 | 10/2001 | Lin et al. | | 6,887,242 B2 | 5/2005 | Doubler et al. |
| 6,302,888 B1 | 10/2001 | Mellinger et al. | | 6,899,714 B2 | 5/2005 | Vaughan |
| 6,309,391 B1 | 10/2001 | Crandall et al. | | 6,918,911 B2 | 7/2005 | Biedermann et al. |
| 6,325,802 B1 | 12/2001 | Frigg | | 6,932,817 B2 | 8/2005 | Baynham et al. |
| 6,328,740 B1 | 12/2001 | Richelsoph | | 6,945,974 B2 | 9/2005 | Dalton |
| 6,344,057 B1 | 2/2002 | Rabbe et al. | | 6,951,561 B2 | 10/2005 | Warren et al. |
| 6,355,040 B1 | 3/2002 | Richelsoph et al. | | 6,964,666 B2 | 11/2005 | Jackson |
| 6,379,354 B1 | 4/2002 | Rogozinski | | 6,966,910 B2 | 11/2005 | Ritland |
| 6,402,749 B1 | 6/2002 | Ashman | | 6,986,771 B2 | 1/2006 | Paul et al. |
| 6,402,751 B1 | 6/2002 | Hoeck et al. | | 6,991,632 B2 | 1/2006 | Ritland |
| 6,402,752 B2 | 6/2002 | Schäffler-Wachter et al. | | 7,008,423 B2 | 3/2006 | Assaker et al. |
| 6,413,257 B1 | 7/2002 | Lin et al. | | 7,011,685 B2 | 3/2006 | Arnin et al. |
| 6,416,515 B1 | 7/2002 | Wagner | | 7,018,378 B2 | 3/2006 | Biedermann et al. |
| 6,423,064 B1 | 7/2002 | Kluger | | 7,018,379 B2 | 3/2006 | Drewry |
| 6,440,169 B1 | 8/2002 | Elberg et al. | | 7,022,122 B2 | 4/2006 | Amrein et al. |
| 6,451,021 B1 | 9/2002 | Ralph et al. | | 7,029,475 B2 | 4/2006 | Panjabi |
| 6,454,773 B1 | 9/2002 | Sherman et al. | | 7,048,736 B2 | 5/2006 | Robinson et al. |
| 6,458,131 B1 | 10/2002 | Ray | | 7,051,451 B2 | 5/2006 | Augostino et al. |
| 6,458,132 B2 | 10/2002 | Choi | | 7,060,066 B2 | 6/2006 | Zhao et al. |
| 6,468,276 B1 | 10/2002 | McKay | | 7,074,237 B2 | 7/2006 | Goble et al. |
| 6,471,705 B1 | 10/2002 | Biedermann et al. | | 7,081,117 B2 | 7/2006 | Bono et al. |
| 6,478,797 B1 | 11/2002 | Paul | | 7,083,621 B2 | 8/2006 | Shaolian et al. |
| 6,482,207 B1 | 11/2002 | Errico | | 7,083,622 B2 | 8/2006 | Simonson |
| 6,485,491 B1 | 11/2002 | Farris et al. | | 7,087,056 B2 | 8/2006 | Vaughan |
| 6,488,681 B2 | 12/2002 | Martin et al. | | 7,087,057 B2 | 8/2006 | Konieczynski et al. |
| 6,520,962 B1 | 2/2003 | Taylor et al. | | 7,087,084 B2 | 8/2006 | Reiley |
| 6,520,990 B1 | 2/2003 | Ray | | 7,090,698 B2 | 8/2006 | Goble et al. |
| 6,537,276 B2 | 3/2003 | Metz-Stavenhagen | | 7,101,398 B2 | 9/2006 | Dooris et al. |
| 6,540,748 B2 | 4/2003 | Lombardo | | 7,104,992 B2 | 9/2006 | Bailey |
| 6,540,749 B2 | 4/2003 | Schäfer et al. | | 7,107,091 B2 | 9/2006 | Jutras et al. |
| 6,547,789 B1 | 4/2003 | Ventre et al. | | 7,125,410 B2 | 10/2006 | Freudiger |
| 6,554,832 B2 | 4/2003 | Shluzas | | 7,125,426 B2 | 10/2006 | Moumene et al. |
| 6,554,834 B1 | 4/2003 | Crozet et al. | | 7,214,227 B2 | 5/2007 | Colleran et al. |
| 6,565,565 B1 | 5/2003 | Yuan et al. | | 7,250,052 B2 | 7/2007 | Landry et al. |
| 6,565,566 B1 | 5/2003 | Wagner et al. | | 7,282,064 B2 | 10/2007 | Chin |
| 6,565,567 B1 | 5/2003 | Haider | | 7,294,129 B2 | 11/2007 | Hawkins et al. |
| 6,565,605 B1 | 5/2003 | Goble et al. | | 7,306,603 B2 | 12/2007 | Boehm, Jr. et al. |
| 6,572,617 B1 | 6/2003 | Senegas | | 7,306,606 B2 | 12/2007 | Sasing |
| 6,572,653 B1 | 6/2003 | Simonson | | 7,326,210 B2 | 2/2008 | Jahng et al. |
| 6,579,290 B1 | 6/2003 | Hardcastle et al. | | 7,335,201 B2 | 2/2008 | Doubler et al. |
| 6,585,737 B1 | 7/2003 | Baccelli et al. | | 2002/0013586 A1 | 1/2002 | Justis et al. |
| 6,616,669 B2 | 9/2003 | Ogilvie et al. | | 2002/0026192 A1 | 2/2002 | Schmiel et al. |
| 6,623,485 B2 | 9/2003 | Doubler et al. | | 2002/0068975 A1 | 6/2002 | Teitelbaum et al. |
| 6,626,905 B1 | 9/2003 | Schmiel et al. | | 2002/0082603 A1 | 6/2002 | Dixon et al. |

| | | | | | | |
|---|---|---|---|---|---|---|
| 2002/0120271 A1 | 8/2002 | Dixon et al. | | 2005/0267470 A1 | 12/2005 | McBride |
| 2002/0143329 A1 | 10/2002 | Serhan et al. | | 2005/0267472 A1 | 12/2005 | Biedermann et al. |
| 2002/0169450 A1 | 11/2002 | Lange | | 2005/0277922 A1 | 12/2005 | Trieu et al. |
| 2003/0004511 A1 | 1/2003 | Ferree | | 2005/0277925 A1 | 12/2005 | Mujwid |
| 2003/0073996 A1 | 4/2003 | Doubler et al. | | 2005/0277927 A1 | 12/2005 | Guenther et al. |
| 2003/0073997 A1 | 4/2003 | Doubler et al. | | 2005/0277928 A1 | 12/2005 | Boschert |
| 2003/0083657 A1 | 5/2003 | Drewry et al. | | 2005/0288670 A1 | 12/2005 | Panjabi et al. |
| 2003/0125742 A1 | 7/2003 | Yuan et al. | | 2005/0288671 A1 | 12/2005 | Yuan et al. |
| 2003/0171749 A1 | 9/2003 | Le Couedic et al. | | 2006/0004357 A1 | 1/2006 | Lee et al. |
| 2003/0191470 A1* | 10/2003 | Ritland ............................ 606/61 | | 2006/0025771 A1 | 2/2006 | Jackson |
| 2004/0015166 A1 | 1/2004 | Gorek | | 2006/0030839 A1 | 2/2006 | Park et al. |
| 2004/0030337 A1 | 2/2004 | Alleyne et al. | | 2006/0036242 A1 | 2/2006 | Nilsson et al. |
| 2004/0039384 A1 | 2/2004 | Boehm, Jr. et al. | | 2006/0036324 A1 | 2/2006 | Sachs et al. |
| 2004/0097925 A1 | 5/2004 | Boehm, Jr. et al. | | 2006/0052783 A1 | 3/2006 | Dant et al. |
| 2004/0097933 A1 | 5/2004 | Lourdel et al. | | 2006/0052784 A1 | 3/2006 | Dant et al. |
| 2004/0111088 A1 | 6/2004 | Picetti et al. | | 2006/0052786 A1 | 3/2006 | Dant et al. |
| 2004/0116929 A1 | 6/2004 | Barker et al. | | 2006/0058787 A1 | 3/2006 | David |
| 2004/0122425 A1 | 6/2004 | Suzuki et al. | | 2006/0058788 A1 | 3/2006 | Hammer et al. |
| 2004/0138662 A1 | 7/2004 | Landry et al. | | 2006/0058790 A1 | 3/2006 | Carl et al. |
| 2004/0143265 A1 | 7/2004 | Landry et al. | | 2006/0064090 A1 | 3/2006 | Park |
| 2004/0147928 A1 | 7/2004 | Landry et al. | | 2006/0064091 A1 | 3/2006 | Ludwig et al. |
| 2004/0153077 A1 | 8/2004 | Biedermann et al. | | 2006/0069391 A1 | 3/2006 | Jackson |
| 2004/0158245 A1 | 8/2004 | Chin | | 2006/0074419 A1 | 4/2006 | Taylor et al. |
| 2004/0158247 A1 | 8/2004 | Sitiso et al. | | 2006/0079894 A1 | 4/2006 | Colleran et al. |
| 2004/0162560 A1 | 8/2004 | Raynor et al. | | 2006/0079896 A1 | 4/2006 | Kwak et al. |
| 2004/0172022 A1 | 9/2004 | Landry et al. | | 2006/0084978 A1 | 4/2006 | Mokhtar |
| 2004/0172024 A1 | 9/2004 | Gorek | | 2006/0084980 A1 | 4/2006 | Melkent et al. |
| 2004/0215192 A1 | 10/2004 | Justis et al. | | 2006/0084982 A1 | 4/2006 | Kim |
| 2004/0225289 A1 | 11/2004 | Biedermann et al. | | 2006/0084983 A1 | 4/2006 | Kim |
| 2004/0230192 A1 | 11/2004 | Graf | | 2006/0084984 A1 | 4/2006 | Kim |
| 2004/0236327 A1 | 11/2004 | Paul et al. | | 2006/0084985 A1 | 4/2006 | Kim |
| 2004/0236330 A1 | 11/2004 | Purcell et al. | | 2006/0084987 A1 | 4/2006 | Kim |
| 2005/0033441 A1 | 2/2005 | Lambrecht et al. | | 2006/0084988 A1 | 4/2006 | Kim |
| 2005/0049589 A1 | 3/2005 | Jackson | | 2006/0084989 A1 | 4/2006 | Dickinson et al. |
| 2005/0065515 A1 | 3/2005 | Jahng | | 2006/0084990 A1 | 4/2006 | Gournay et al. |
| 2005/0070899 A1 | 3/2005 | Doubler et al. | | 2006/0084993 A1 | 4/2006 | Landry et al. |
| 2005/0070901 A1 | 3/2005 | David | | 2006/0084995 A1 | 4/2006 | Biedermann et al. |
| 2005/0080415 A1 | 4/2005 | Keyer et al. | | 2006/0085069 A1 | 4/2006 | Kim |
| 2005/0085813 A1 | 4/2005 | Spitler et al. | | 2006/0085070 A1 | 4/2006 | Kim |
| 2005/0090822 A1 | 4/2005 | DiPoto | | 2006/0089643 A1 | 4/2006 | Mujwid |
| 2005/0096652 A1 | 5/2005 | Burton | | 2006/0089644 A1 | 4/2006 | Felix |
| 2005/0096659 A1 | 5/2005 | Freudiger | | 2006/0095035 A1 | 5/2006 | Jones et al. |
| 2005/0107788 A1 | 5/2005 | Beaurain et al. | | 2006/0095038 A1 | 5/2006 | Jackson |
| 2005/0113927 A1 | 5/2005 | Malek | | 2006/0100621 A1 | 5/2006 | Jackson |
| 2005/0113929 A1 | 5/2005 | Cragg et al. | | 2006/0100622 A1 | 5/2006 | Jackson |
| 2005/0119658 A1 | 6/2005 | Ralph et al. | | 2006/0106380 A1 | 5/2006 | Colleran et al. |
| 2005/0124991 A1 | 6/2005 | Jahng | | 2006/0106383 A1 | 5/2006 | Biedermann et al. |
| 2005/0131404 A1 | 6/2005 | Mazda et al. | | 2006/0111712 A1 | 5/2006 | Jackson |
| 2005/0131405 A1 | 6/2005 | Molz, IV et al. | | 2006/0111715 A1 | 5/2006 | Jackson |
| 2005/0131406 A1 | 6/2005 | Reiley et al. | | 2006/0116676 A1 | 6/2006 | Gradel et al. |
| 2005/0143737 A1 | 6/2005 | Pafford et al. | | 2006/0122597 A1 | 6/2006 | Jones et al. |
| 2005/0143823 A1 | 6/2005 | Boyd et al. | | 2006/0122599 A1 | 6/2006 | Drewry et al. |
| 2005/0171537 A1 | 8/2005 | Mazel et al. | | 2006/0122620 A1 | 6/2006 | Kim |
| 2005/0171543 A1 | 8/2005 | Timm et al. | | 2006/0129147 A1 | 6/2006 | Biedermann et al. |
| 2005/0177156 A1 | 8/2005 | Timm et al. | | 2006/0129148 A1 | 6/2006 | Simmons et al. |
| 2005/0177157 A1 | 8/2005 | Jahng | | 2006/0129149 A1 | 6/2006 | Iott et al. |
| 2005/0177164 A1 | 8/2005 | Walters et al. | | 2006/0142761 A1 | 6/2006 | Landry et al. |
| 2005/0177166 A1 | 8/2005 | Timm et al. | | 2006/0149231 A1 | 7/2006 | Bray |
| 2005/0182400 A1 | 8/2005 | White | | 2006/0149232 A1 | 7/2006 | Sasing |
| 2005/0182401 A1 | 8/2005 | Timm et al. | | 2006/0149234 A1 | 7/2006 | de Coninck |
| 2005/0182409 A1 | 8/2005 | Callahan et al. | | 2006/0149237 A1 | 7/2006 | Markworth et al. |
| 2005/0187548 A1 | 8/2005 | Butler et al. | | 2006/0149238 A1 | 7/2006 | Sherman et al. |
| 2005/0192569 A1 | 9/2005 | Nichols et al. | | 2006/0149240 A1 | 7/2006 | Jackson |
| 2005/0192571 A1 | 9/2005 | Abdelgany | | 2006/0149242 A1 | 7/2006 | Kraus et al. |
| 2005/0192572 A1 | 9/2005 | Abdelgany et al. | | 2006/0149244 A1 | 7/2006 | Amrein et al. |
| 2005/0203514 A1 | 9/2005 | Jahng et al. | | 2006/0149380 A1 | 7/2006 | Lotz et al. |
| 2005/0203517 A1 | 9/2005 | Jahng et al. | | 2006/0155277 A1 | 7/2006 | Metz-Stavenhagen |
| 2005/0203518 A1 | 9/2005 | Biedermann et al. | | 2006/0155278 A1 | 7/2006 | Warnick |
| 2005/0222570 A1 | 10/2005 | Jackson | | 2006/0161153 A1 | 7/2006 | Hawkes et al. |
| 2005/0228375 A1 | 10/2005 | Mazda et al. | | 2006/0173456 A1 | 8/2006 | Hawkes et al. |
| 2005/0228382 A1 | 10/2005 | Richelsoph et al. | | 2006/0195093 A1 | 8/2006 | Jahng |
| 2005/0228385 A1 | 10/2005 | Iott et al. | | 2006/0200128 A1 | 9/2006 | Mueller |
| 2005/0234451 A1 | 10/2005 | Markworth | | 2006/0200130 A1 | 9/2006 | Hawkins et al. |
| 2005/0234454 A1 | 10/2005 | Chin | | 2006/0200131 A1 | 9/2006 | Chao et al. |
| 2005/0234557 A1 | 10/2005 | Lambrecht et al. | | 2006/0200133 A1 | 9/2006 | Jackson |
| 2005/0240180 A1 | 10/2005 | Vienney et al. | | 2006/0217716 A1 | 9/2006 | Baker et al. |
| 2005/0240265 A1 | 10/2005 | Kuiper et al. | | 2006/0229606 A1 | 10/2006 | Clement et al. |
| 2005/0240266 A1 | 10/2005 | Kuiper et al. | | 2006/0229607 A1 | 10/2006 | Brumfield |
| 2005/0261770 A1 | 11/2005 | Kuiper et al. | | 2006/0229613 A1 | 10/2006 | Timm et al. |

| | | |
|---|---|---|
| 2006/0229615 A1 | 10/2006 | Abdou |
| 2006/0229616 A1 | 10/2006 | Albert et al. |
| 2006/0235385 A1 | 10/2006 | Whipple |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241594 A1 | 10/2006 | McCarthy et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0241757 A1 | 10/2006 | Anderson |
| 2006/0247623 A1 | 11/2006 | Anderson et al. |
| 2006/0247624 A1 | 11/2006 | Bonouskou et al. |
| 2006/0247628 A1 | 11/2006 | Rawlins et al. |
| 2006/0247631 A1 | 11/2006 | Ahn et al. |
| 2006/0247636 A1 | 11/2006 | Yuan et al. |
| 2006/0247637 A1 | 11/2006 | Colleran et al. |
| 2006/0253118 A1 | 11/2006 | Bailey |
| 2006/0264935 A1 | 11/2006 | White |
| 2006/0264937 A1 | 11/2006 | White |
| 2006/0276897 A1 | 12/2006 | Winslow et al. |
| 2006/0282073 A1 | 12/2006 | Simanovsky |
| 2006/0282078 A1 | 12/2006 | Labrom et al. |
| 2007/0005062 A1 | 1/2007 | Lange et al. |
| 2007/0005063 A1 | 1/2007 | Bruneau et al. |
| 2007/0016190 A1 | 1/2007 | Martinez et al. |
| 2007/0016194 A1 | 1/2007 | Shaolian et al. |
| 2007/0016201 A1 | 1/2007 | Freudiger |
| 2007/0032123 A1 | 2/2007 | Timm et al. |
| 2007/0043356 A1 | 2/2007 | Timm et al. |
| 2007/0043358 A1 | 2/2007 | Molz, IV et al. |
| 2007/0049936 A1 | 3/2007 | Colleran et al. |
| 2007/0073289 A1 | 3/2007 | Kwak et al. |
| 2007/0083200 A1 | 4/2007 | Gittings et al. |
| 2007/0088359 A1 | 4/2007 | Woods et al. |
| 2007/0093814 A1 | 4/2007 | Callahan, II et al. |
| 2007/0093820 A1 | 4/2007 | Freudiger |
| 2007/0093821 A1 | 4/2007 | Freudiger |
| 2007/0093829 A1 | 4/2007 | Abdou |
| 2007/0118122 A1 | 5/2007 | Butler et al. |
| 2007/0123861 A1 | 5/2007 | Dewey et al. |
| 2007/0123871 A1 | 5/2007 | Jahng |
| 2007/0156143 A1 | 7/2007 | Lancial |
| 2007/0161994 A1 | 7/2007 | Lowery et al. |
| 2007/0161997 A1 | 7/2007 | Thramann et al. |
| 2007/0162007 A1 | 7/2007 | Shoham |
| 2007/0167947 A1 | 7/2007 | Gittings |
| 2007/0168035 A1 | 7/2007 | Koske |
| 2007/0198014 A1 | 8/2007 | Graf et al. |
| 2007/0213714 A1 | 9/2007 | Justis |
| 2007/0213719 A1 | 9/2007 | Hudgins et al. |
| 2007/0233068 A1 | 10/2007 | Bruneau et al. |
| 2007/0233072 A1 | 10/2007 | Dickinson et al. |
| 2007/0233075 A1 | 10/2007 | Dawson |
| 2007/0233090 A1 | 10/2007 | Naifeh et al. |
| 2007/0233091 A1 | 10/2007 | Naifeh et al. |
| 2007/0233092 A1 | 10/2007 | Falahee |
| 2007/0233093 A1 | 10/2007 | Falahee |
| 2007/0233094 A1 | 10/2007 | Colleran et al. |
| 2007/0244481 A1 | 10/2007 | Timm |
| 2007/0250061 A1 | 10/2007 | Chin et al. |
| 2007/0270819 A1 | 11/2007 | Justis et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0276380 A1 | 11/2007 | Jahng et al. |
| 2007/0288009 A1 | 12/2007 | Brown et al. |
| 2007/0288012 A1 | 12/2007 | Colleran et al. |
| 2008/0009864 A1 | 1/2008 | Forton et al. |
| 2008/0021285 A1 | 1/2008 | Drzyzga et al. |
| 2008/0021459 A1 | 1/2008 | Lim |
| 2008/0021461 A1 | 1/2008 | Barker et al. |
| 2008/0033433 A1 | 2/2008 | Implicito |
| 2008/0039838 A1 | 2/2008 | Landry et al. |
| 2008/0045951 A1 | 2/2008 | Fanger et al. |
| 2008/0045957 A1 | 2/2008 | Landry et al. |
| 2008/0051787 A1 | 2/2008 | Remington et al. |
| 2008/0065073 A1 | 3/2008 | Perriello et al. |
| 2008/0065075 A1 | 3/2008 | Dant et al. |
| 2008/0065079 A1 | 3/2008 | Bruneau et al. |
| 2008/0071273 A1 | 3/2008 | Hawkes et al. |
| 2008/0077139 A1 | 3/2008 | Landry et al. |

FOREIGN PATENT DOCUMENTS

| | | |
|---|---|---|
| DE | 3639810 A1 | 5/1988 |
| EP | 0128058 A1 | 12/1984 |
| EP | 0669109 B1 | 8/1995 |
| EP | 1281362 A2 | 2/2003 |
| EP | 1330987 A1 | 7/2003 |
| FR | 2612070 A1 | 9/1988 |
| FR | 2615095 A1 | 11/1988 |
| FR | 2880256 B1 | 7/2006 |
| GB | 780652 | 8/1957 |
| GB | 2173104 | 10/1986 |
| GB | 2382304 | 5/2003 |
| WO | WO 87/07134 | 12/1987 |
| WO | WO 94/21185 | 9/1994 |
| WO | WO 98/27884 | 7/1998 |
| WO | WO 01/45576 | 6/2001 |
| WO | WO 01/91656 | 12/2001 |
| WO | WO 02/07621 | 1/2002 |
| WO | WO 02/07622 | 1/2002 |
| WO | WO 02/17803 | 3/2002 |
| WO | WO 02/39921 | 5/2002 |
| WO | WO 02/43603 | 6/2002 |
| WO | WO 02/102259 | 12/2002 |
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO2004/024011 | 3/2004 |
| WO | WO2004/034916 | 4/2004 |
| WO | WO2006/033503 | 3/2006 |
| WO | WO2006/066685 | 6/2006 |
| WO | WO2006/105935 | 10/2006 |
| WO | WO2007/080317 | 7/2007 |
| WO | WO2008/034130 | 3/2008 |

OTHER PUBLICATIONS

International Search Report for PCT/US/08/65444 dated Sep. 16, 2008, 4 pages.

Mekanika—The Spinal Stabilization Company, product description for Modulus System, 2 pages, http://mekanika.com/htm/modsystem.htm.

Zimmer Spine, product description for Dynesis—The Dynamic Stabilization System, 5 pages, http://www.zimmer.com/ctl?template=IN&action=1&op=global&id=9165&pr=Y.

Itoika Medical Instruments, product description for S-Plate, 15 pages, http://ito-ika.co.jp/s-plate/splate1.pdf and http://ito-ika.co.jp/s-plate/splate1.pdf.

"Flexible rods and the case for dynamic stabilization," Jason M. Highsmith, M.D., et al., *Neurosurg. Focus*, vol. 22, Jan. 2007, pp. 1-5.

"The Spinous Process: The Forgotten Appendage," Kenneth R. Kattan, M. D. eta l., *Skeletal Radiology*, vol. 6, 1981, pp. 199-204.

"Morphological and functional changes of the lumbar spinous processes in the elderly," R. Scapinelli, *Surgical Radiologic Anatomy*, vol. 11, 1989, pp. 129-133.

"The Paraspinal Sacrospinalis-Splitting Approach to the Lumbar Spine," Leon L. Wiltse et al., *The Journal of Bone & Joint Surgery*, vol. 50-A, No. 5, Jul. 1968 pp. 919-926.

*Dynamic Reconstruction of the Spine*, D.H. Kim et al., 2006, cover through p. xix.

"Historical Review of Spinal Arthroplasty and Dynamic Stabilizations," K M. Shibata et al., *Dynamic Reconstruction of the Spine*, Section I, Motion Preservation of the Spine, Chapter 1, 2006, pp. 3-15.

"Current Concepts in Spinal Fusion versus Nonfusion," D.H. Walker et al., *Dynamic Reconstruction of the Spine*, Section I, Motion Preservation of the Spine, Chapter 2, 2006, pp. 16-23.

"Biomechanical Aspects Associated with Cervical Disk Arthroplasty," D.J. DiAngelo et al., *Dynamic Reconstruction of the Spine*, Section II, Restoration of Cervical Motion Segment, Chapter 3, 2006, pp. 27-32.

"Biomechanical Testing Protocol for Evaluating Cervical Disk Arthroplasty," D.J. DiAngelo et al., *Dynamic Reconstruction of the Spine*, Section II, Restoration of Cervical Motion Segment, Chapter 4, 2006, pp. 33-41.

"Cervical Disk Arthroplasty: Rationale, Indications, and Clinical Experience," M.R. Lim et al., *Dynamic Reconstruction of the Spine*, Section II, Restoration of Cervical Motion Segment, Chapter 5, 2006, pp. 42-51.

"Spinal Kinetics Cervical Disc," D.H. Kim et al., *Dynamic Reconstruction of the Spine*, Section II, Restoration of Cervical Motion Segment, Chapter 6, 2006, pp. 52-58.

"Bryan Cervical Disc Device," R. Hacker, *Dynamic Reconstruction of the Spine*, Section II, Restoration of Cervical Motion Segment, Chapter 7, 2006, pp. 59-66.

"Prestige Cervical Artificial Disk," J.T. Robertson, *Dynamic Reconstruction of the Spine*, Section II, Restoration of Cervical Motion Segment, Chapter 8, 2006, pp. 67-71.

"ProDisc-C Cervical Artificial Disk" G.K. Jeong et al., *Dynamic Reconstruction of the Spine*, Section II, Restoration of Cervical Motion Segment, Chapter 9, 2006, pp. 72-77.

"PCM (Porous Coated Motion) Artificial Cervical Disc," L Pimenta et al., *Dynamic Reconstruction of the Spine*, Section II, Restoration of Cervical Motion Segment, Chapter 10, 2006, pp. 78-85.

"Cervidisc Concept: Six-Year Follow-Up and Introducing Cervidisc II: DISCOCERV," A.S. Ramadan et al., *Dynamic Reconstruction of the Spine*, Section II, Restoration of Cervical Motion Segment, Chapter 11, 2006, pp. 86-91.

"CerviCore Cervical Intervertebral Disk Replacement," S.S. Lee et al., *Dynamic Reconstruction of the Spine*, Section II, Restoration of Cervical Motion Segment, Chapter 12, 2006, pp. 92-95.

"Prosthetic Disk Nucleus Partial Disk Replacement: Pathobiological and Biomechanical Rationale for Design and Function," C.D. Ray et al., *Dynamic Reconstruction of the Spine*, Section III, Restoration of Lumbar Motion Segment, A. Lumbar Nucleus Replacement, Chapter 13, 2006, pp. 99-104.

"The Raymedica Prosthetic Disk Nucleus (PDN): Stabilizing the Degenerated Lumbar Vertebral Segment without Fusion or Total Disk Replacement," C.D. Ray, *Dynamic Reconstruction of the Spine*, Section III, Restoration of Lumbar Motion Segment, A. Lumbar Nucleus Replacement, Chapter 14, pp. 105-113.

"Functional Lumbar Artificial Nucleus Replacement: The DASCOR System," J.E. Sherman et al., *Dynamic Reconstruction of the Spine*, Section III, Restoration of Lumbar Motion Segment, A. Lumbar Nucleus Replacement, Chapter 15, 2006, pp. 114-121.

"NeuDisc," R. Bertagnoli et al., *Dynamic Reconstruction of the Spine*, Section III, Restoration of Lumbar Motion Segment, A. Lumbar Nucleus Replacement, Chapter 16, 2006, pp. 122-126.

"Pioneer Surgical Technology NUBAC Artificial Nucleus," Q. Bao et al., *Dynamic Reconstruction of the Spine*, Section III, Restoration of Lumbar Motion Segment, A. Lumbar Nucleus Replacement, Chapter 17, 2006, pp. 128-136.

"SINUX (Sinitec)," J. Zoellner, *Dynamic Reconstruction of the Spine*, Section III, Restoration of Lumbar Motion Segment, A. Lumbar Nucleus Replacement, Chapter 18, 2006, pp. 137-141.

"Nucore Injectable Disk Nucleus," S.H. Kitchel et al., *Dynamic Reconstruction of the Spine*, Section III, Restoration of Lumbar Motion Segment, A. Lumbar Nucleus Replacement, Chapter 19, 2006, pp. 142-146.

"Biomechanical Considerations for Total Lumbar Disk Replacement," J. LeHuec et al., *Dynamic Reconstruction of the Spine*, Section III, Restoration of Lumbar Motion Segment, B. Lumbar Total Disk Replacement, Chapter 20, 2006, pp. 149-153.

"Indications for Total Lumbar Disk Replacement," R. Bertagnoli, *Dynamic Reconstruction of the Spine*, Section III, Restoration of Lumbar Motion Segment, B. Lumbar Total Disk Replacement, Chapter 21, 2006, pp. 154-159.

"CHARTÉ Artificial Disc," F.H. Geisler, *Dynamic Reconstruction of the Spine*, Section III, Restoration of Lumbar Motion Segment, B. Lumbar Total Disk Replacement, Chapter 22, 2006, pp. 160-178.

"ProDisc Lumbar Artificial Disk," J.E.Zigler et al., *Dynamic Reconstruction of the Spine*, Section III, Restoration of Lumbar Motion Segment, B. Lumbar Total Disk Replacement, Chapter 23, 2006, pp. 179-185.

"MAVERICK Total Disc Replacement," M.F.Gornet, *Dynamic Reconstruction of the Spine*, Section III, Restoration of Lumbar Motion Segment, B. Lumbar Total Disk Replacement, Chapter 24, 2006, pp. 186-195.

"The Mobidisc Prosthesis," J.P. Steib et al., *Dynamic Reconstruction of the Spine*, Section III, Restoration of Lumbar Motion Segment, B. Lumbar Total Disk Replacement, Chapter 25, 2006, pp. 196-203.

"Activ-L Lumbar (Aesculap) Total Disk Arthroplasty," J.J. Yue et al., *Dynamic Reconstruction of the Spine*, Section III, Restoration of Lumbar Motion Segment, B. Lumbar Total Disk Replacement, Chapter 26, 2006, pp. 204-211.

"The FlexiCore Disk," A.D. Sharan et al., *Dynamic Reconstruction of the Spine*, Section III, Restoration of Lumbar Motion Segment, B. Lumbar Total Disk Replacement, Chapter 27, 2006, pp. 212-220.

"Management of Vascular and Surgical Approach—Related Complications for Lumbar Total Disk Replacement," S.H. Lee et al., *Dynamic Reconstruction of the Spine*, Section III, Restoration of Lumbar Motion Segment, B. Lumbar Total Disk Replacement, Chapter 28, 2006, pp. 221-226.

"Complications of Lumbar Disk Arthroplasty," SH Lee et al., *Dynamic Reconstruction of the Spine*, Section III, Restoration of Lumbar Motion Segment, B. Lumbar Total Disk Replacement, Chapter 29, 2006, pp. 227-233.

"Rationale for Dynamic Stabilization," D.S. McNally, *Dynamic Reconstruction of the Spine*, Section III, Restoration of Lumbar Motion Segment, C. Dynamic Posterior Stabilization, Chapter 30, 2006, pp. 237-243.

"Rationale for Dynamic Stabilization II—SoftFlex System," D.K. Sengupta, *Dynamic Reconstruction of the Spine*, Section III, Restoration of Lumbar Motion Segment, C. Dynamic Posterior Stabilization, Chapter 31, 2006, pp. 244-250.

"The X STOP Interspinous Process Decompression System for the Treatment of Lumbar Neurogenic Claudication," R.M. Thunder et al., *Dynamic Reconstruction of the Spine*, Section III, Restoration of Lumbar Motion Segment, C. Dynamic Posterior Stabilization, Chapter 32, 2006, pp. 251-257.

"Dynamic Lumbar Stabilization with the Wallis Interspinous Implant," J. Sénégas, *Dynamic Reconstruction of the Spine*, Section III, Restoration of Lumbar Motion Segment, C. Dynamic Posterior Stabilization, Chapter 33, 2006, pp. 258-267.

"Coflex," ES Kim et al., *Dynamic Reconstruction of the Spine*, Section III, Restoration of Lumbar Motion Segment, C. Dynamic Posterior Stabilization, Chapter 34, 2006, pp. 268-273.

DIAM (Device for Intervertebral Assisted Motion) Spinal Stabilization System, K. Singh et al., *Dynamic Reconstruction of the Spine*, Section III, Restoration of Lumbar Motion Segment, C. Dynamic Posterior Stabilization, Chapter 35, 2006, pp. 274-283.

"Tension Band System," SH Lee et al., *Dynamic Reconstruction of the Spine*, Section III, Restoration of Lumbar Motion Segment, C. Dynamic Posterior Stabilization, Chapter 36, 2006, pp. 284-291.

"Shape Memory Implant (KIMPF-DI Fixing) System," YS Kim et al., *Dynamic Reconstruction of the Spine*, Section III, Restoration of Lumbar Motion Segment, C. Dynamic Posterior Stabilization, Chapter 37, 2006, pp. 292-298.

"Treatment of Mobile Vertebral Instability with Dynesys," G. Dubois et al., *Dynamic Reconstruction of the Spine*, Section III, Restoration of Lumbar Motion Segment, C. Dynamic Posterior Stabilization, Chapter 38, 2006, pp. 299-304.

"Graf Soft Stabilization: Graf Ligamentoplasty," YS Kim et al., *Dynamic Reconstruction of the Spine*, Section III, Restoration of Lumbar Motion Segment, C. Dynamic Posterior Stabilization, Chapter 39, 2006, pp. 305-311.

"Isobar TTL Dynamic Instrumentation," A.E. Castellvi et al., *Dynamic Reconstruction of the Spine*, Section III, Restoration of Lumbar Motion Segment, C. Dynamic Posterior Stabilization, Chapter 40, 2006, pp. 312-322.

"Minimally Invasive Posterior Dynamic Stabilization System," L. Pimenta et al., *Dynamic Reconstruction of the Spine*, Section III, Restoration of Lumbar Motion Segment, C. Dynamic Posterior Stabilization, Chapter 41, 2006, pp. 323-329.

"Nonfusion Stabilization of the Degenerated Lumbar Spine with Cosmic," A. von Strempel, *Dynamic Reconstruction of the Spine*, Section III, Restoration of Lumbar Motion Segment, C. Dynamic Posterior Stabilization, Chapter 42, 2006, pp. 330-339.

"BioFlex Spring Rod Pedicle Screw System," YS Kim et al., *Dynamic Reconstruction of the Spine*, Section III, Restoration of Lumbar Motion Segment, C. Dynamic Posterior Stabilization, Chapter 43, 2006, pp. 340-344.

"Facet Replacement Technologies," M.R. Lim et al., *Dynamic Reconstruction of the Spine*, Section III, Restoration of Lumbar Motion Segment, D. Facet Replacement, Chapter 44, 2006, pp. 347-353.

"TOPS—Total Posterior Facet Replacement and Dynamic Motion Segment Stabilization System," L.T. Khoo et al., *Dynamic Reconstruction of the Spine*, Section III, Restoration of Lumbar Motion Segment, D. Facet Replacement, Chapter 45, 2006, pp. 354-363.

"Total Facet Arthroplasty System (TFAS)," S. Webb, *Dynamic Reconstruction of the Spine*, Section III, Restoration of Lumbar Motion Segment, D. Facet Replacement, Chapter 46, 2006, pp. 364-371.

"Indications and Techniques in Annuloplasty," M.Y. Wang, *Dynamic Reconstruction of the Spine*, Section III, Restoration of Lumbar Motion Segment, E. Annular Repair, Chapter 47, 2006, pp. 375-379.

"Molecular Therapy of the Intervertebral Disk," S.T. Yoon, *Dynamic Reconstruction of the Spine*, Section IV, Future Biological Approaches to Disk Repair, Chapter 48, 2006, pp. 383-388.

*Dynamic Reconstruction of the Spine*, D.H. Kim et al., 2006, Index, pp. 389-402.

International Search Report for PCT/US07/70981 dated Apr. 23, 2008, 7 pages.

* cited by examiner

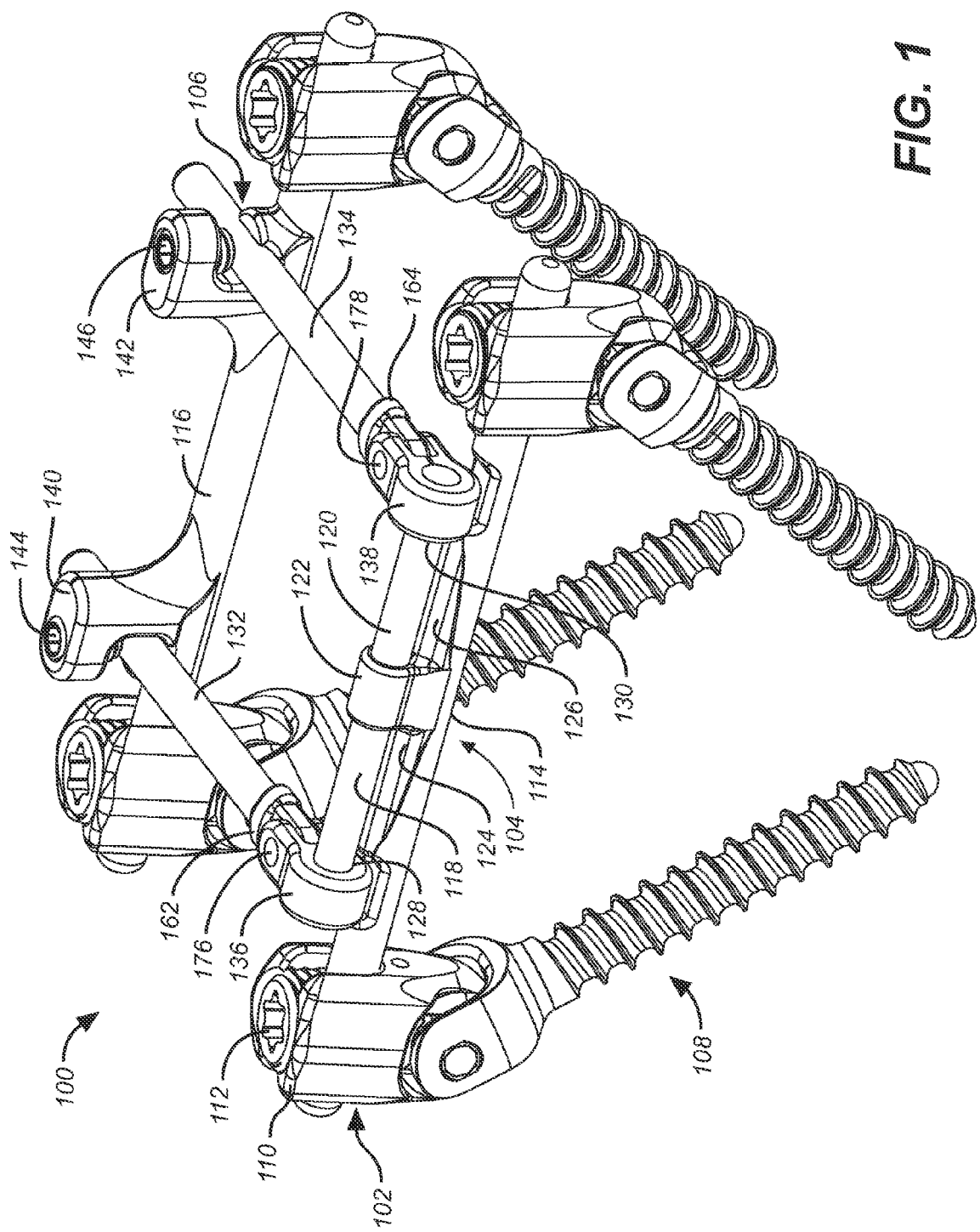

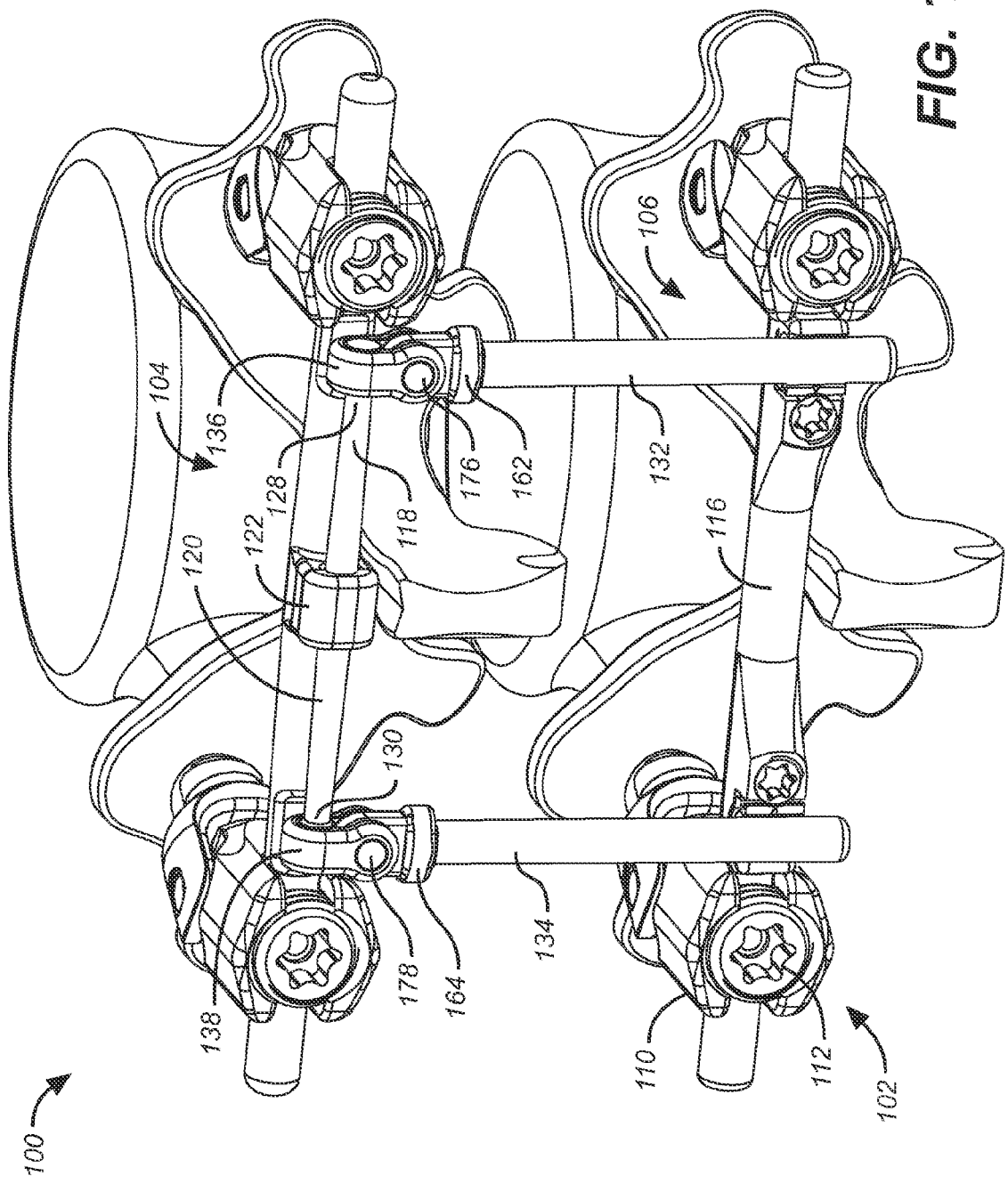

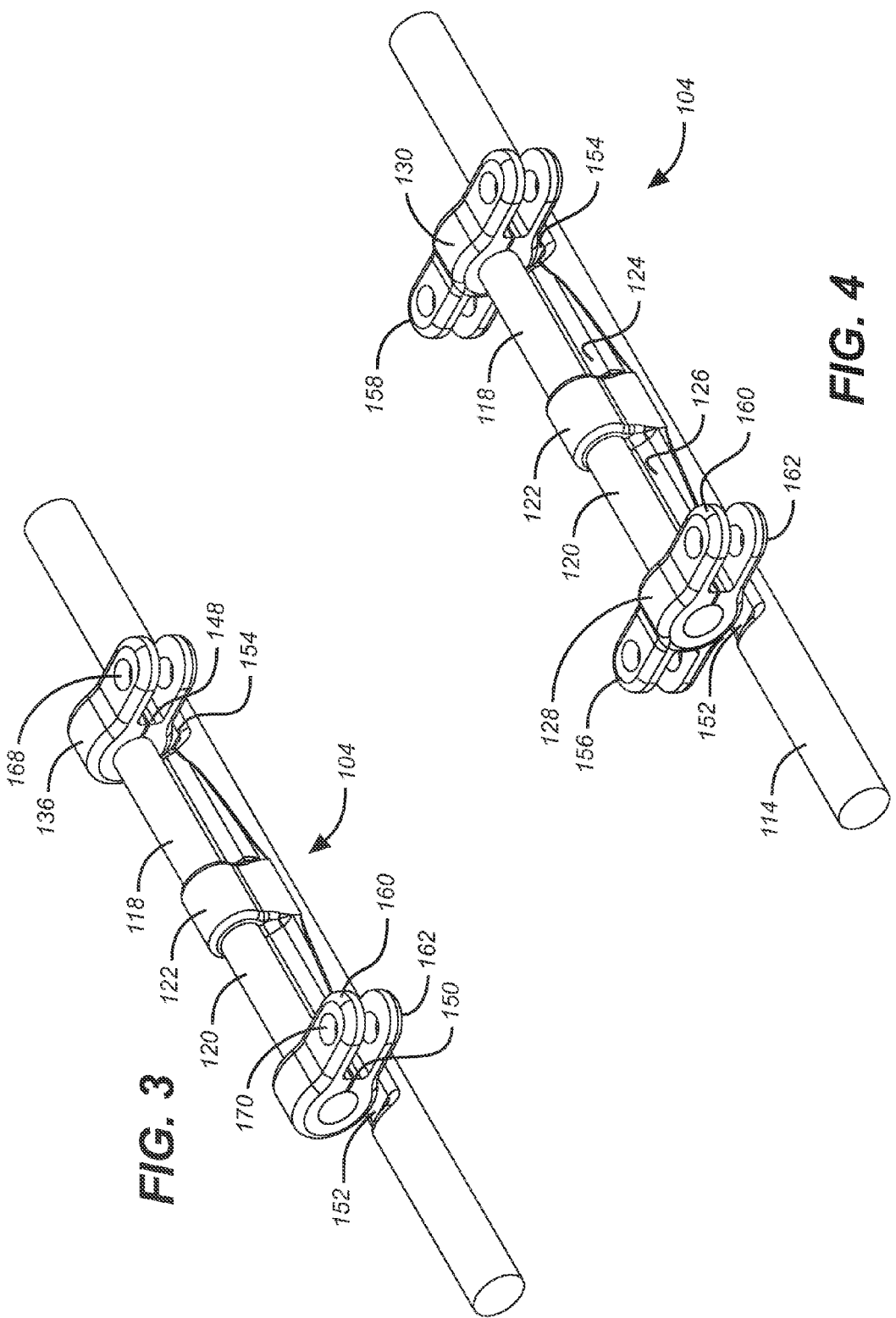

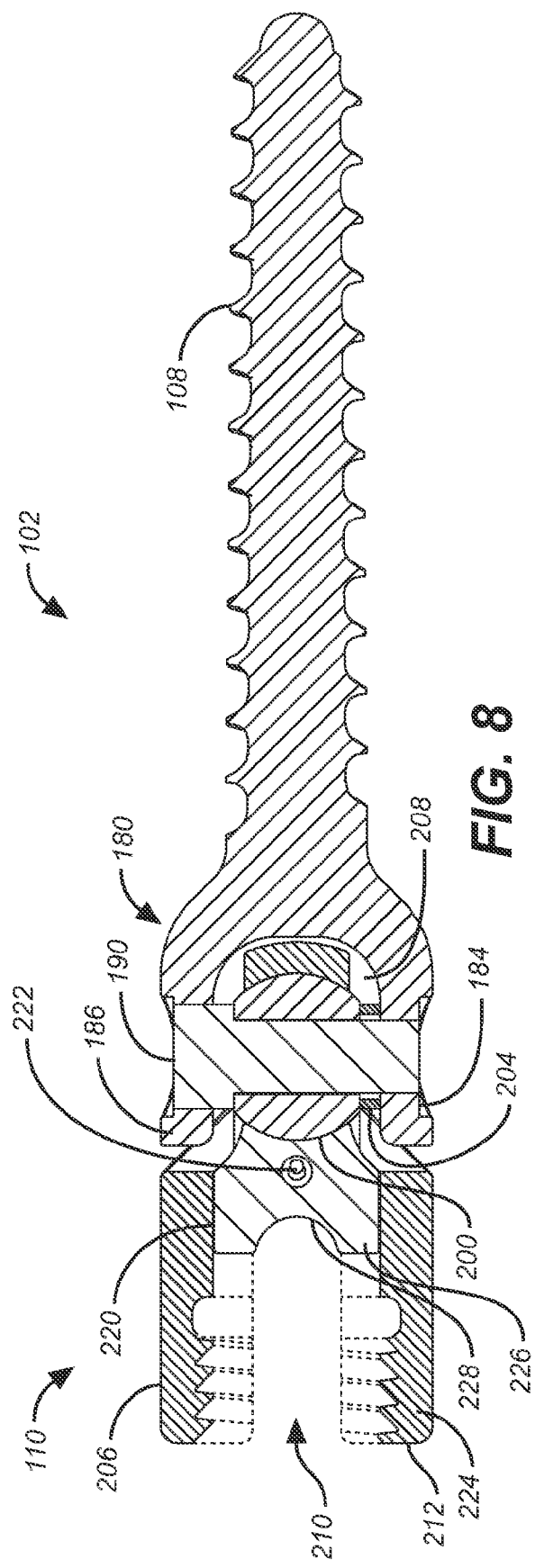

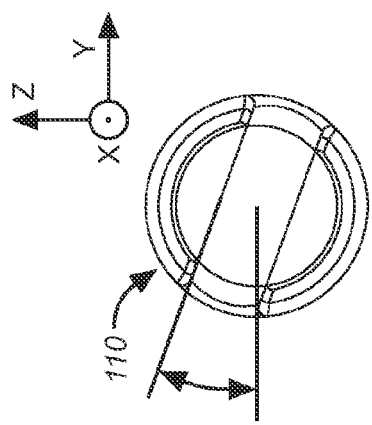
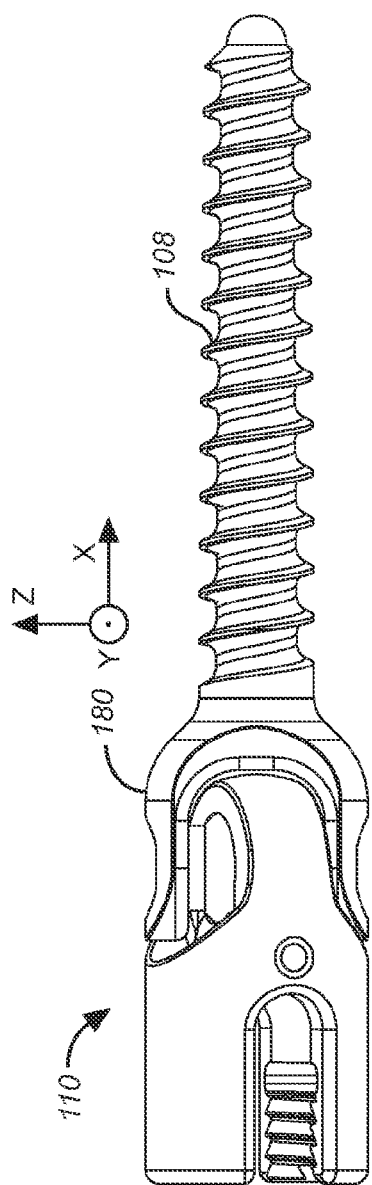
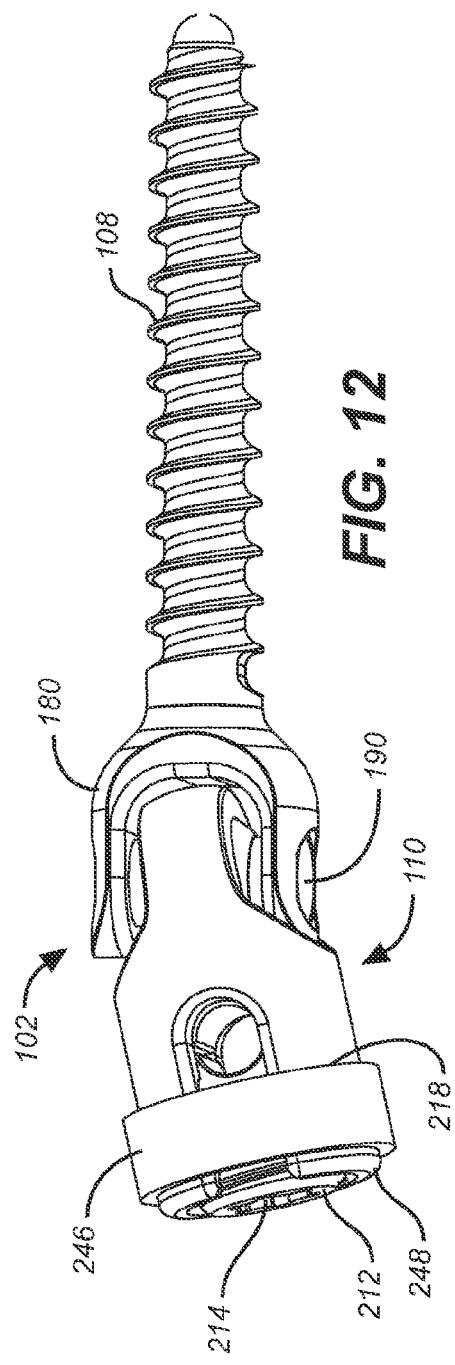

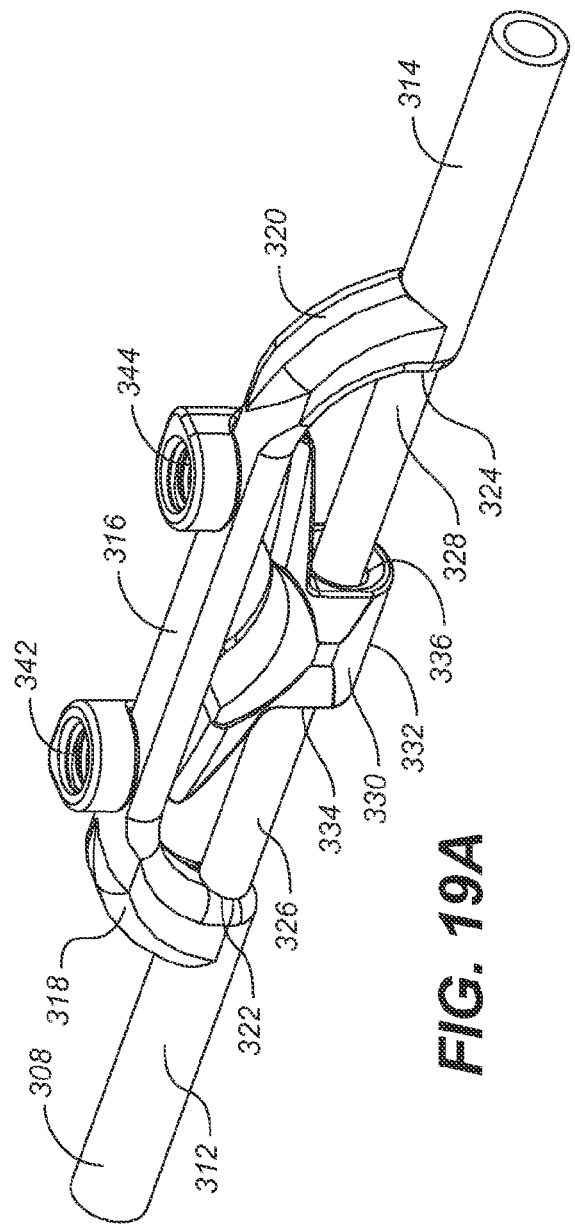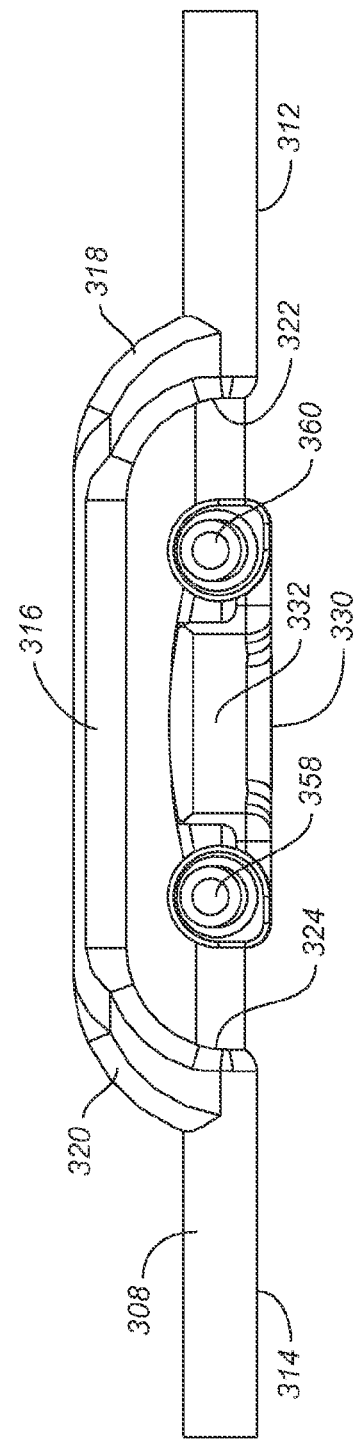

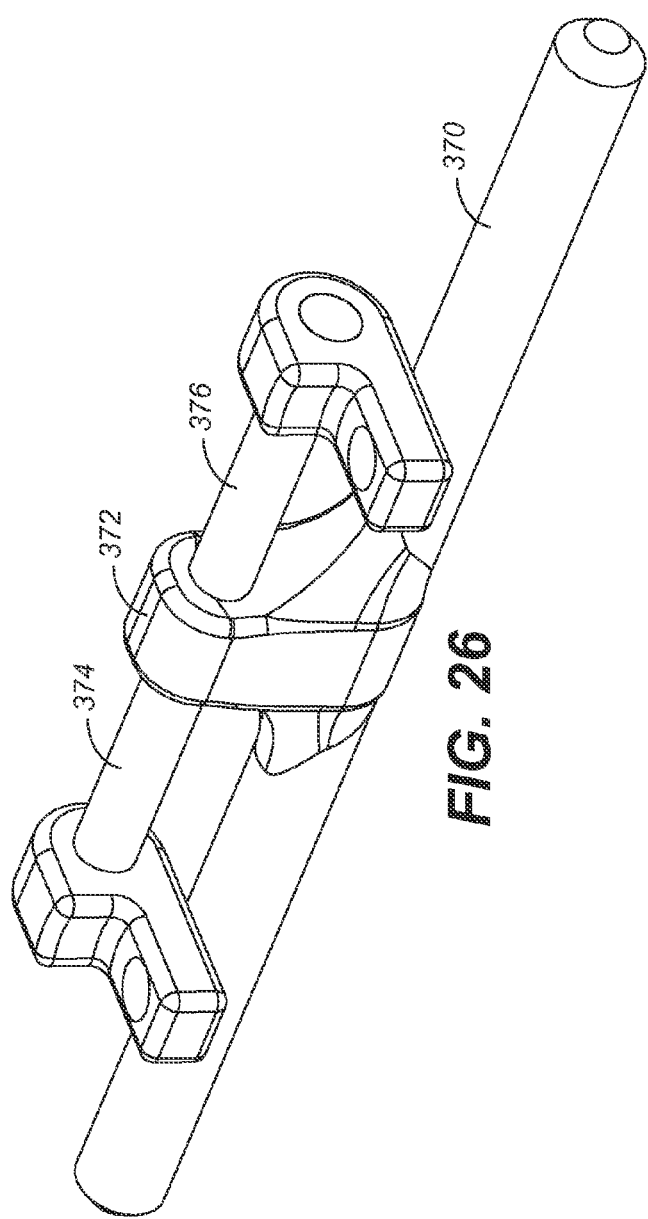
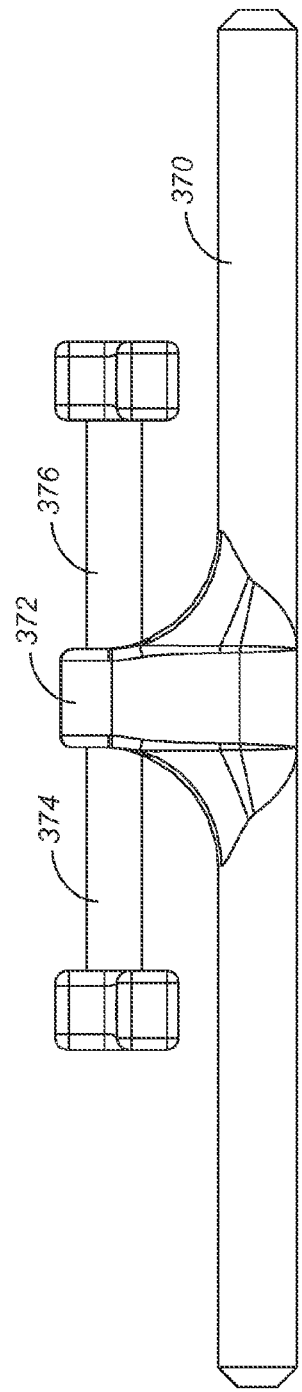
FIG. 26
FIG. 27

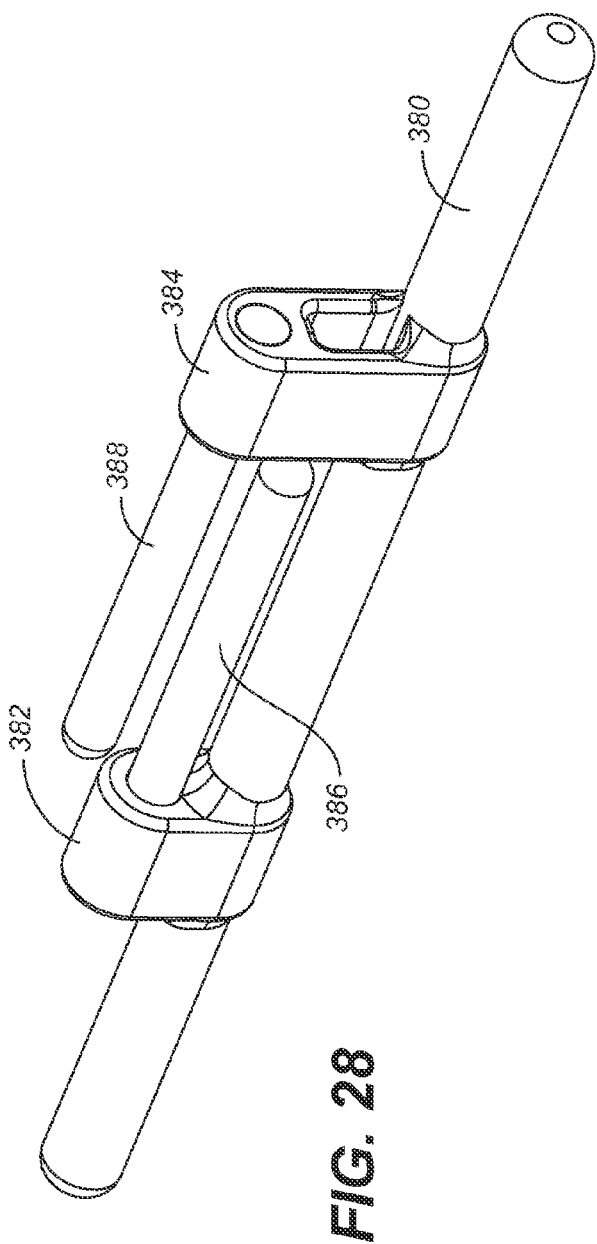
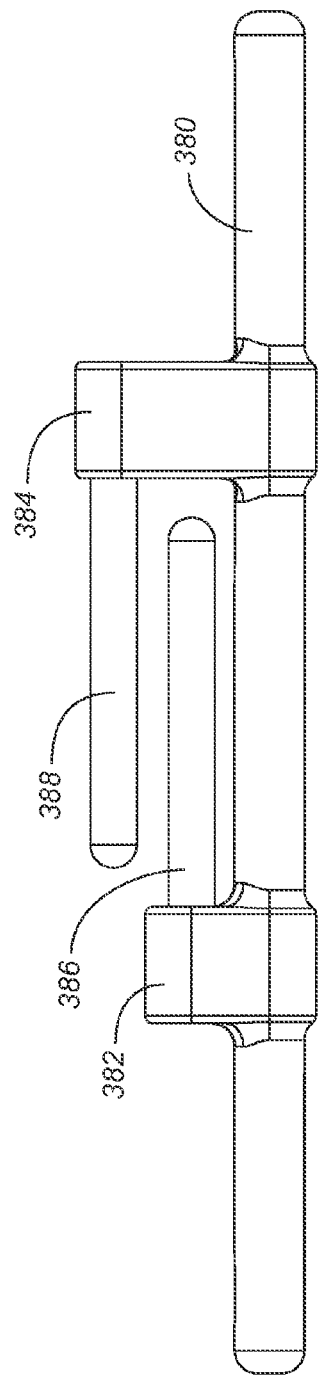
FIG. 28
FIG. 29

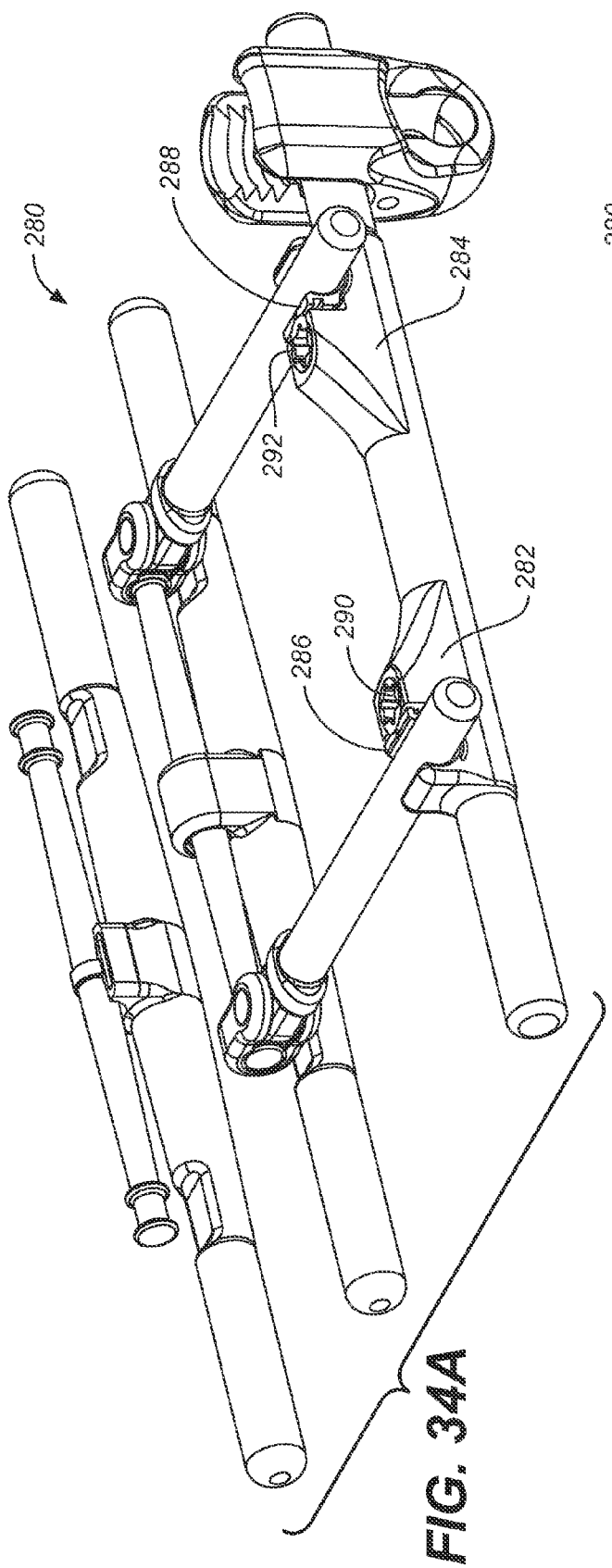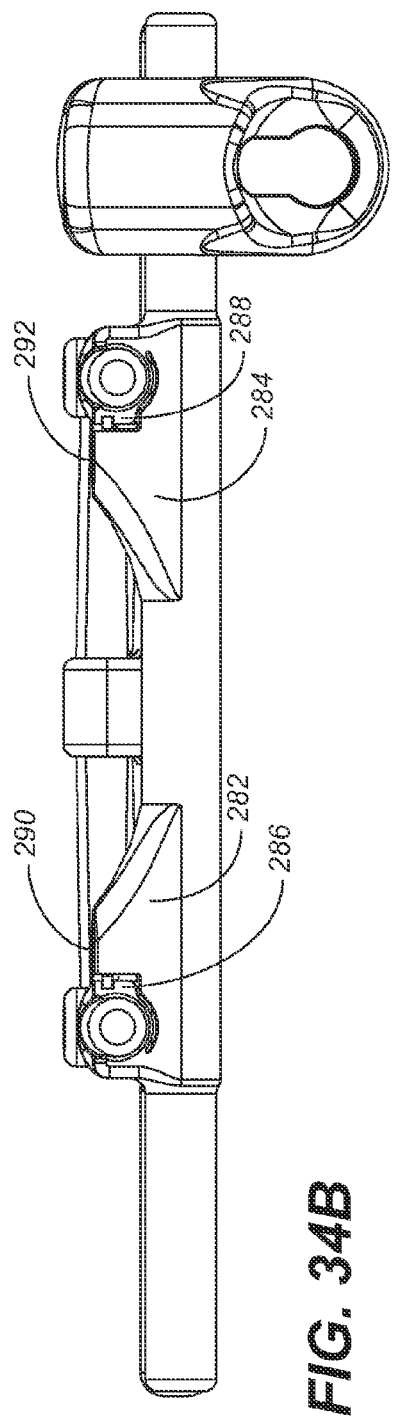
FIG. 34A
FIG. 34B

MODULAR SPINE TREATMENT KIT FOR DYNAMIC STABILIZATION AND MOTION PRESERVATION OF THE SPINE

CLAIM OF PRIORITY

This application claims benefit to U.S. Provisional Application No. 60/942,162, filed Jun. 5, 2007, entitled "Dynamic Stabilization and Motion Preservation Spinal Implantation System and Method", which is incorporated herein by reference and in its entirety.

CROSS-REFERENCES

This application relates to, and incorporates herein by reference and in their entireties, U.S. Patent Application No. 60/801,871, filed Jun. 14, 2006, entitled "Implant Positioned Between the Lamina to Treat Degenerative Disorders of the Spine";

U.S. patent application Ser. No. 11/761,006, filed Jun. 11, 2007, entitled "Implant System and Method to Treat Degenerative Disorders of the Spine";

U.S. patent application Ser. No. 11/761,100, filed Jun. 11, 2007, entitled "Implant System and Method to Treat Degenerative Disorders of the Spine"; and U.S. patent application Ser. No. 11/761,116, filed Jun. 11, 2007, entitled "Implant System and Method to Treat Degenerative Disorders of the Spine".

BACKGROUND OF INVENTION

The most dynamic segment of orthopedic and neurosurgical medical practice over the past decade has been spinal devices designed to fuse the spine to treat a broad range of degenerative spinal disorders. Back pain is a significant clinical problem and the annual costs to treat it, both surgical and medical, is estimated to be over $2 billion. Motion preserving devices to treat back and extremity pain has, however, created a treatment alternative to fusion for degenerative disc disease. These devices offer the possibility of eliminating the long term clinical consequences of fusing the spine that is associated with accelerated degenerative changes at adjacent disc levels.

BRIEF DESCRIPTION OF THE DRAWINGS

FIG. 1 is a perspective view of an embodiment of a dynamic spine stabilization system of the invention.

FIG. 1A is a posterior view of the embodiment of FIG. 1 implanted in a spine.

FIG. 3 is a perspective view of an embodiment of a horizontal rod system of the invention for use with a dynamic spine stabilization system such as depicted in FIG. 1.

FIG. 4 is a perspective view of an alternative embodiment of a horizontal rod system of the invention for use with a dynamic spine stabilization system such as depicted in FIG. 1.

FIG. 8 is a sectioned view of a portion of embodiment of the alternative anchor system of FIG. 7 of the invention.

FIG. 11 is a side view of the anchor system of FIG. 7 depicting yet another degree of freedom of movement of the anchor system of FIG. 7.

FIG. 11A is an end view of the anchor system of FIG. 11.

FIG. 12 is a perspective view of yet another embodiment of the anchor system of the invention.

FIG. 18 is a perspective view of yet another embodiment of the anchor system of the invention.

FIG. 19A is a perspective view of another horizontal rod system of the invention as depicted in FIG. 19 and partially shown in phantom form.

FIG. 19C is a side view of the embodiment of FIG. 19.

FIG. 26 is a perspective view of yet another embodiment of the horizontal rod system of the invention.

FIG. 27 is a side view of the embodiment of the horizontal rod system of the invention of FIG. 26.

FIG. 28 is a perspective view of still another embodiment of the horizontal rod system of the invention.

FIG. 29 is a side view of the embodiment of the horizontal rod system of the invention of FIG. 28.

FIG. 34A is a perspective view of yet another embodiment of the horizontal rod system of the invention.

FIG. 34B is a side view of the embodiment of FIG. 34A.

DETAILED DESCRIPTION OF THE PREFERRED EMBODIMENTS

Figure 2:
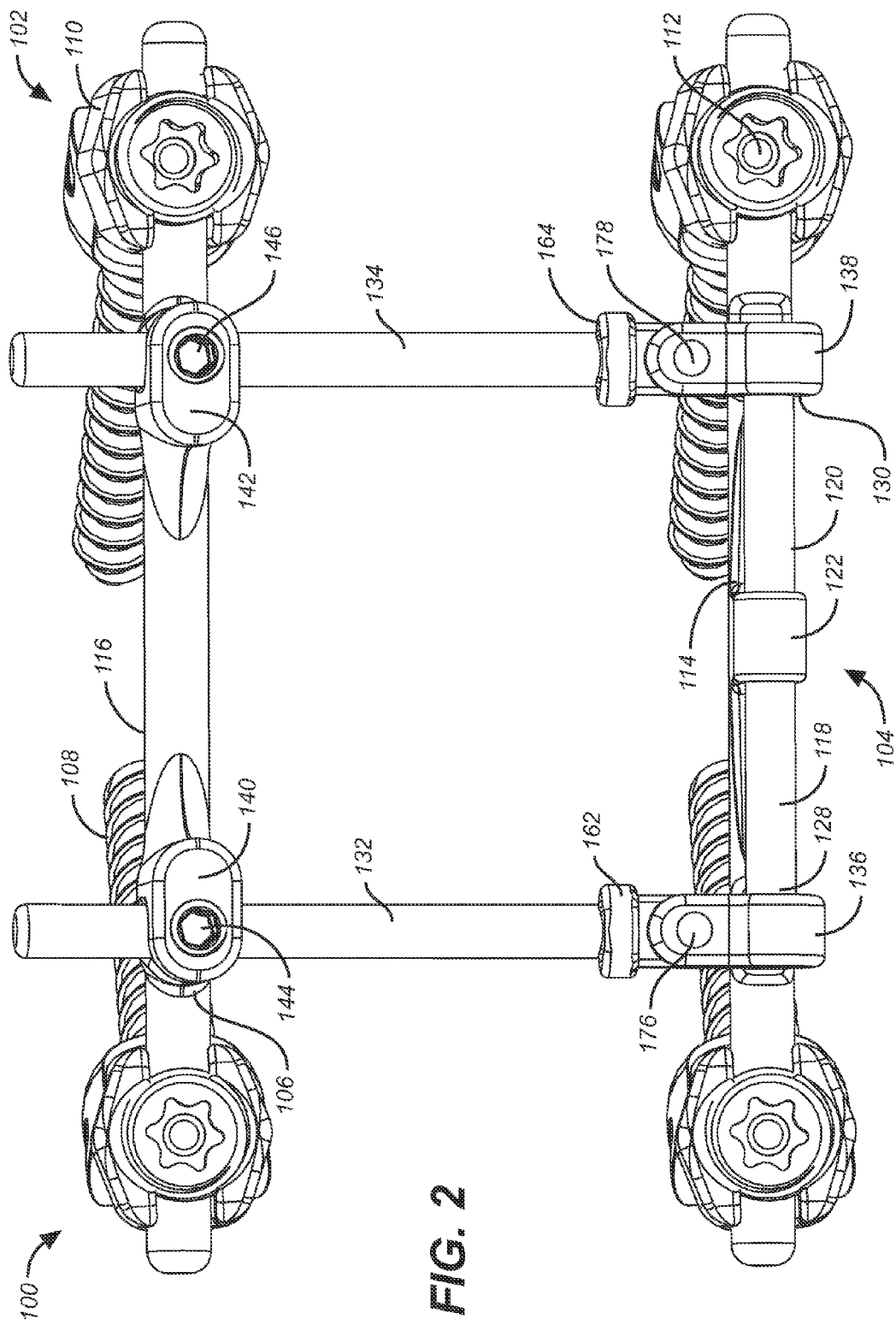
FIG. 2 is a top view of the embodiment of FIG. 1.

Embodiments of the present invention include a system or implant and method that can dynamically stabilize the spine while providing for preservation of spinal motion. Alternative embodiments can be used for spine fusion.

Embodiments of the invention include a construct with an anchoring system, a horizontal rod system that is associated with the anchoring system and a vertical rod system that is associated with the anchoring system and the horizontal rod system.

An advantage and aspect of the system is that the anchoring system includes a head or saddle that allows for appropriate, efficient and convenient placement of the anchoring system relative to the spine in order to reduce the force that is placed on the anchoring system. The anchor system has enhanced degrees of freedom which contribute to the ease of implantation of the anchor system. Accordingly, the anchor system is designed to isolate the head and the screw from the rest of the dynamic stabilization system and the forces that the rest of the dynamic stabilization system can place on the anchor system and the anchor system/bone interface. Thus, the anchor system can provide a secure purchase in the spine.

Another advantage and aspect of the system is that the horizontal rod system is in part comprised of a super elastic material that allows for convenient positioning of the horizontal rod system relative to the anchor system and allows for isolation of the horizontal rod system from the anchor system so that less force is placed on the anchor system from the horizontal rod system and on the anchor system/bone interface. Accordingly, unlike prior devices the anchor system stays secure in the bone of the spine.

An aspect and advantage of the invention is the ability to maximize the range of motion of the spine after embodiments of the dynamic stabilization, motion preservation implant of the invention are implanted in a patient. While traditional solutions to back pain include fusion, discectomy, and artificial implants that replace spine structure, embodiments of the present invention preserve the bone and ligament structure of the spine and preserve a wide range of motion of the spine, while stabilizing spines that were heretofore unstable due to degenerative and other spinal diseases.

Still another aspect of the invention is the preservation of the natural motion of the spine and the maintenance of the quality of motion as well as the wide range of motion so that the spine motion is as close to that of the natural spine as possible. The present embodiments of the invention allow for the selection of a less stiff, yet dynamically stable implant for use in a non-fusion situation. A less stiff, yet dynamically stable implant relates directly to a positive patient outcome, including patient comfort and the quality of motion of the spine.

In another aspect of the invention, load sharing is provided by the embodiment, and, in particular, the deflection rod or loading rod of the embodiment. For embodiments of this invention, the terms "deflection rod" and "loading rod" can be used interchangeably. Accordingly this aspect of the invention is directed to restoring the normal motion of the spine. The embodiment provides stiffness and support where needed to support the loads exerted on the spine during normal spine motion, which loads, the soft tissues of the spine are no longer able to accommodate since these spine tissues are either degenerated or damaged. Load sharing is enhanced by the ability to select the appropriate stiffness of the deflection rod or loading rod in order to match the load sharing desired. By selecting the appropriate stiffness of the deflection rod or loading rod to match the physiology of the patient and the loads that the patient places on the spine, a better outcome is realized for the patient. Prior to implantation of the embodiment, the stiffness of the implant of the system can be selected among a number of loading rods. In other words, the stiffness is variable depending on the deflection rod or loading rod selected. In another aspect, the load sharing is between the spine and the embodiment of the invention.

In another aspect of the invention, the deflection rod or loading rod is cantilevered. In another aspect the deflection rod or loading rod is cantilevered from a horizontal rod. In yet another aspect the deflection rod or loading rod is cantilevered from a horizontal rod that is connected between two anchors that are affixed to the same vertebra. In yet another aspect the deflection rod or loading rod is about parallel to the horizontal rod in a resting position. In still a further, aspect the deflection rod or loading rod is cantilevered from a mount on the horizontal rod and said deflection rod or loading rod is about parallel to the horizontal rod in a resting position.

In another aspect of the invention the horizontal rod attached directly to opposite anchors is stiff and rigid, and the cantilevered deflection rod or cantilevered loading rod shares the load with the spine resulting from the motions of the body of the patient.

In another aspect of embodiments of the invention, the load being absorbed or carried by the embodiment is being distributed along at least part of the length of the deflection rod or loading rod. In another aspect of the invention, the load being absorbed or carried by the embodiment is distributed along at least part of the length of the horizontal cantilevered deflection rod or horizontal cantilevered loading rod.

As the load is carried horizontally along the deflection rod or loading rod, rather than vertically, the embodiments of the invention can be made smaller in order to fit in more spaces relative to the spine. Advantageously, the embodiments can fit in the L5-S1 space of the spine.

An aspect of the invention is to preserve and not restrict motion between the pedicles of the spine through the use of appropriately selected horizontal and vertical rods of embodiments of the invention.

An aspect of the invention is to provide for load bearing on horizontal elements such as horizontal rods instead of vertical elements or rods, and, in particular, vertical elements that are connected between bone anchoring systems.

An aspect of the invention is the use of horizontal rods in the embodiments of the invention in order to isolate each level of the implantation system from the other so as not to put undue force and/or torque on anchoring systems of embodiment of the invention and associated bone, and so as to allow customization of the implantation system to the need of the patient. Accordingly, an aspect of the invention is to provide for minimized loading on the bone/implantation system interface. Customization, in preferred embodiments, can be achieved by the selection of the horizontal rod with the desired stiffness and stiffness characteristics. Different materials and different implant configurations enable the selection of various stiffness characteristics.

Another aspect of the invention is the ability to control stiffness for extension, flexion, lateral bending and axial rotation, and to control stiffness for each of these motions independently of the other motions.

An aspect of the invention is to use the stiffness and load bearing characteristics of super elastic materials.

Another aspect of the invention is to use super elastic materials to customize the implant to the motion preservation and the dynamic stabilization needs of a patient. An aspect of such embodiments of the invention is to provide for a force plateau where motion of the implantation system continues without placement of additional force of the bone anchor system, or, in other words, the bone/implantation system interface.

Thus, an aspect of the invention is to use the horizontal bar to offset loading on the anchor system and on the implantation system in general.

Accordingly, an aspect of the invention is to be able to selectively vary the stiffness and selectively vary the orientation and direction that the stiffness is felt by varying the structure of the implantation system of the invention, and, in particular, to vary the stiffness of the horizontal rod system of the invention.

Another aspect of embodiments of the invention is to prevent any off-axis implantation by allowing the implantation system to have enhanced degrees of freedom of placement of the implant. Embodiments of the invention provide for off-axis placement of bone anchor or pedicle screw systems.

A further aspect of embodiments of the invention is to control stabilized motion from micro-motion to broad extension, flexion, axial rotation, and lateral bending motions of the spine.

Yet another aspect of the embodiments of the invention is to be able to revise a dynamic stabilization implant should a fusion implant be indicated. This procedure can be accomplished by, for example, the removal of the horizontal rods of the implantation system and replacement of such rods with stiffer rods. Accordingly, an aspect of the invention is to provide for a convenient path for a revision of the original implantation system, if needed.

A further aspect of the invention, due to the ease of implanting the anchoring system and the ease of affixing vertical rods to the horizontal rods of the invention, is the ability to accommodate the bone structure of the spine, even if adjacent vertebra are misaligned with respect to each other.

A further aspect of the invention is that the implant is constructed around features of the spine such as the spinous processes and, thus, such features do not need to be removed and the implant does not get in the way of the normal motion of the spine features and the spine features do not get in the way of the operation of the implant.

Another aspect of embodiments of the invention is the ability to stabilize two, three and/or more levels of the spine by the selection of appropriate embodiments and components of embodiments of the invention for implantation in a patient. Further embodiments of the invention allow for fused levels (in conjunction with, if desired, bone graphs) to be placed next to dynamically stabilized levels with the same implantation system. Such embodiments of the invention enable vertebral levels adjacent to fusion levels to be shielded by avoiding an abrupt change from a rigid fusion level to a dynamically stable, motion preserved, and more mobile level.

Accordingly, another aspect of the embodiments of the invention is to provide a modular system that can be customized to the needs of the patient. Horizontal rods can be selectively chosen for the particular patient as well the particular levels of the vertebrae of the spine that are treated. Further, the positioning of the various selected horizontal rods can be selected to control stiffness and stability.

Another aspect of embodiments of the invention is that embodiments can be constructed to provide for higher stiffness and fusion at one level while allowing for lower stiffness and dynamic stabilization at another adjacent level.

Yet a further aspect of the invention is to provide for dynamic stabilization and motion preservation while preserving the bone and tissues of the spine in order to lessen trauma to the patient and to use the existing functional bone and tissue of the patient as optimally as possible in cooperation with embodiments of the invention.

Another object of the invention is to implant the embodiments of the invention in order to unload force from the spinal facets and other posterior spinal structures and also the intervertebral disk.

A further aspect of the invention is to implant the embodiment of the invention with a procedure that does not remove or alter bone or tear or sever tissue. In an aspect of the invention the muscle and other tissue can be urged out of the way during the inventive implantation procedure.

Accordingly, an aspect of the invention is to provide for a novel implantation procedure that is minimally invasive.

Dynamic Stabilization, Motion Preservation System for the Spine

A dynamic stabilization, motion preservation system 100 embodiment of the invention is depicted in FIG. 1 and includes an anchor system 102, a horizontal rod system 104, and a vertical rod system 106. For these embodiments horizontal refers to a horizontal orientation with respect to a human patient that is standing and vertical refers to a vertical orientation with respect to a patient that is standing (FIG. 1A). As will be more fully disclosed herein below, one embodiment for the anchor system 102 includes a bone screw 108 which is mounted to a head or saddle 110. Alternatively, the bone screw 108 can be replaced by a bone hook as more fully described in U.S. Provisional Patent Application No. 60/801, 871, entitled "An Implant Position Between the Lamina to Treat Degenerative Disorders of the Spine," which was filed on Jun. 14, 2006, and is incorporated herein by reference and in its entirety. The mounting of the head or saddle 110 to the bone screw 108 allows for multiple degrees of freedom in order that the bone screw 108 may be appropriately, conveniently, and easily placed in the bone of the spine and in order to assist in isolating the bone screw 108 from the remainder of the system 100 so that less force is placed on the anchor system 102 and on the bone screw/bone interface. Some prior art devices, which use such bone screws, have, on occasion, had the bone screws loosen from the spine, and the present embodiment is designed to reduce the force on the bone screw and on the bone screw/bone interface. Preferably, the anchor system 102 is comprised of titanium. However, other biocompatible materials such as stainless steal and/or PEEK can be used.

In the embodiment of FIG. 1, the horizontal bar system 104 is preferably secured through the head 110 of the anchor system 102 with a locking set screw 112. This embodiment includes a first horizontal rod 114 and a second horizontal rod 116. The first horizontal rod 114 has first and second deflection rods or loading rods 118 and 120 secured thereto. In a preferred embodiment, the first horizontal rod can be comprised of titanium, stainless steel or PEEK or another biocompatible material, and the first and second deflection rods or loading rods can be comprised of a super elastic material. Preferably, the super elastic material is comprised on Nitinol (NiTi). In addition to Nitinol or nickel-titanium (NiTi), other super elastic materials include copper-zinc-aluminum and copper-aluminum-nickel. However, for biocompatibility, the nickel-titanium is the preferred material.

Such an arrangement allows for the horizontal rod system 104 to isolate forces placed thereon from the anchor system 102 and, thus, isolate forces that could be placed on the bone screw 108 and the bone screw/bone interface of the spine, and, thus, prevent the loosening of the bone screw 108 in the spine. As shown in FIG. 1 the deflection rods or loading rods 118 and 120, in this preferred embodiment, are mounted in the center of the first horizontal rod 114 to a mount 122. Preferably, the deflection rods or loading rods 118 and 120 are force fit into the mount 122. Alternatively, the deflection rods or loading rods may be screwed, glued, or laser welded to the mount 122 and to bores placed in the mount 122. Other fastening techniques are within the scope and spirit of the invention. As can be seen in FIGS. 1, 3, and 4, the first horizontal rod 114 includes first and second ridges 124, 126 located on either side of the mount 122 and extend at least partially along the length of the first horizontal rod 114 toward the respective ends of the horizontal rod 114. These ridges 124, 126 add rigidity to the mount 122 relative to the rest of the horizontal rod system 104.

As seen in FIG. 1, the deflection rods or loading rods 118, 120 have a constant diameter extending outwardly toward the respective ends 128, 130 of the deflection rods or loading rods 118, 120. Alternatively, the deflection rods or loading rods 118, 120 can have a varying diameter as the rods 118, 120 approach their respective ends 128, 130. Preferably, as depicted and discussed below, the rods 118 and 120 can have a decreasing diameter as the rods approach the respective ends 128, 130. The decreasing diameter allows the super elastic rods 118, 120 to be more flexible and bendable along the length of the rods as the rods approach the ends 128, 130 and to more evenly distribute the load placed on the system 100 by the spine. Preferably, the diameter of the deflection rods or loading rods continuously decreases in diameter. However, it can be understood that the diameter can decrease in discrete steps along the length, with the diameter of one step not being continuous with the diameter of the next adjacent step. Alternatively, for different force and load carrying criteria the diameters of the deflection rods or loading rods can continuously increase in diameter or can have discreet step increases in diameter along the length of the deflection rods or loading rods as the rods extent toward the respective ends 128, 130. Still further, the rods can have at least one step of decreasing diameter and at least one step of increasing diameter in any order along the length of the deflection rods or loading rods as the rods approach the respective ends 128, 130, as desired for the force and load carrying characteristics of the deflection rods or loading rods 118, 120.

With respect to FIG. 3, for example, the horizontal rod system 104, and, in particular, the deflection rods 118, 120, share the load carried by the spine. This load sharing is directed to restoring the normal motion of the spine. This embodiment, and, in particular, the deflection rods or loading rods 118, 120, provide stiffness and support where needed to support the loads exerted on the spine during spine motion, which loads, the soft tissues of the spine are no longer able to accommodate since these spine tissues are either degenerated or damaged. Such load sharing is enhanced by the ability to select the appropriate stiffness of the deflection rods or loading rods 118, 120 in order to match the load sharing desired. By selecting the appropriate stiffness of the deflection or loading rods, to match the physiology of the patient, and the loads that the patient places on the spine, a better outcome is realized by the patient. Prior to implantation, the stiffness of the deflection or loading rods can be selected from a number of deflection or loading rods. The stiffness is variable depending on the deflection or load rod selected. As indicated herein, the stiffness of the deflection or loading rod can be varied by the shape of the rod and the selection of the material. Shape variations can include diameter, taper, direction of taper, stepped tapering, and material variation can include composition of material, just to name a few variations.

It is to be understood that the load carried by the deflection or loading rods is distributed along at least part of the length of the deflection or loading rods. Preferably, the load is distributed along the entire length of the deflection or loading rods. Further, as the load is carried horizontally and the stiffness can be varied along a horizontal member, rather than vertically, the embodiments of the invention can be made smaller in order to fit in more spaces relative to the spine. Advantageously, embodiments can fit, for example, in the L5-S1 space of the spine in addition to generally less constrained spaces such as the L4-L5 space of the spine.

With respect to the embodiment of the horizontal rod system of the invention as depicted for example in FIG. 3, the deflection rods or loading rods 118, 120 are cantilevered from mount 122. Thus, these deflection rods 118, 120 have a free end and an end fixed by the mount 112, which mount is located on the horizontal rod 114. As is evident in FIG. 3, the cantilevered deflection rods 118, 120 are about parallel in a rested position to the horizontal rod 114, and, in this embodiment, the horizontal rod is directly connected to the anchor systems and, in particular, to the heads or saddles of the anchor system. Preferably, the horizontal rod 114 is stiff and rigid and, particularly, in comparison to the deflection rods. In this arrangement, the horizontal rod system and, in particular, the deflection rods 118, 120 share the load resulting from the motions of the body of the patient.

Figure 43:
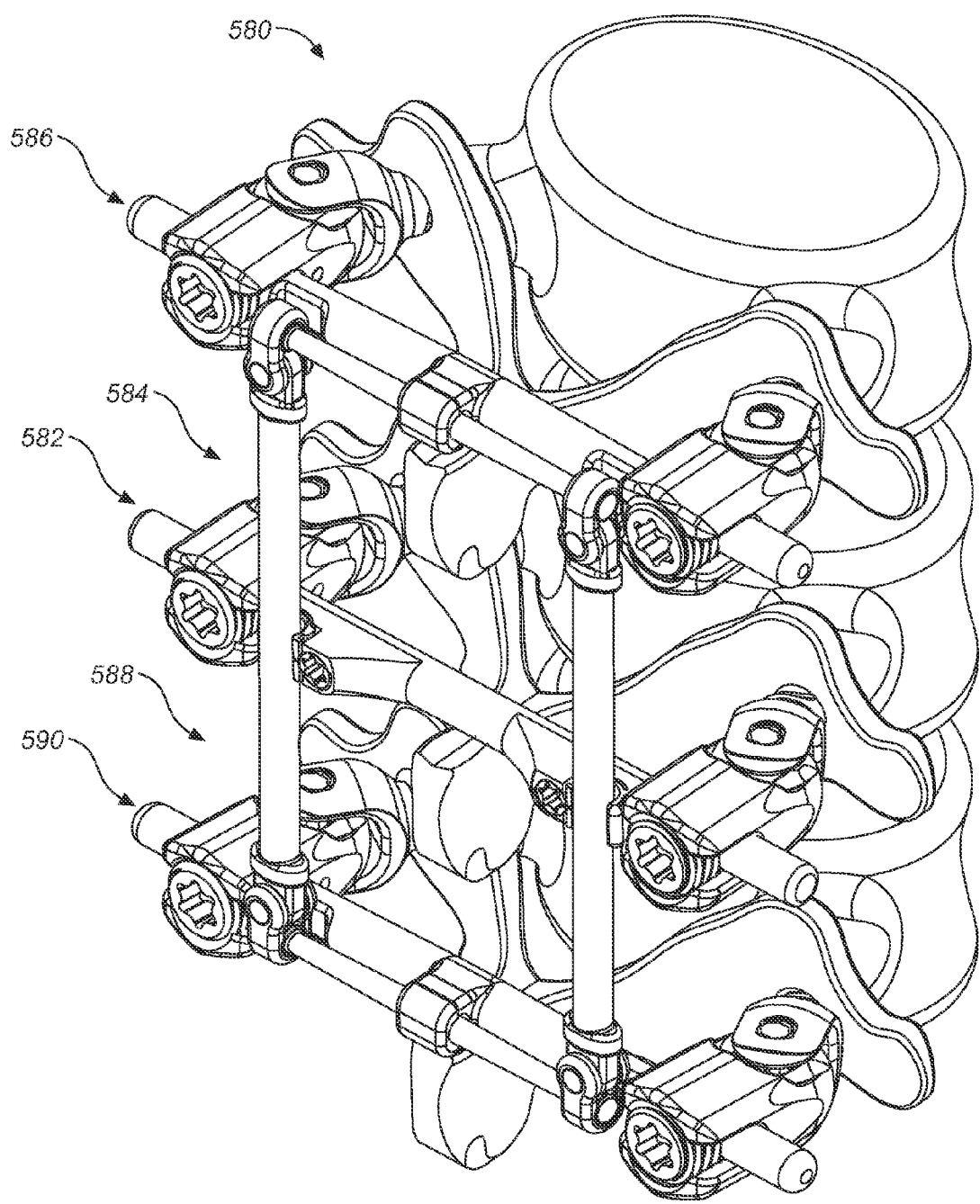
FIG. 43 is a side view of yet another embodiment of a two level dynamic spine stabilization system of the invention.
Figure 43A:
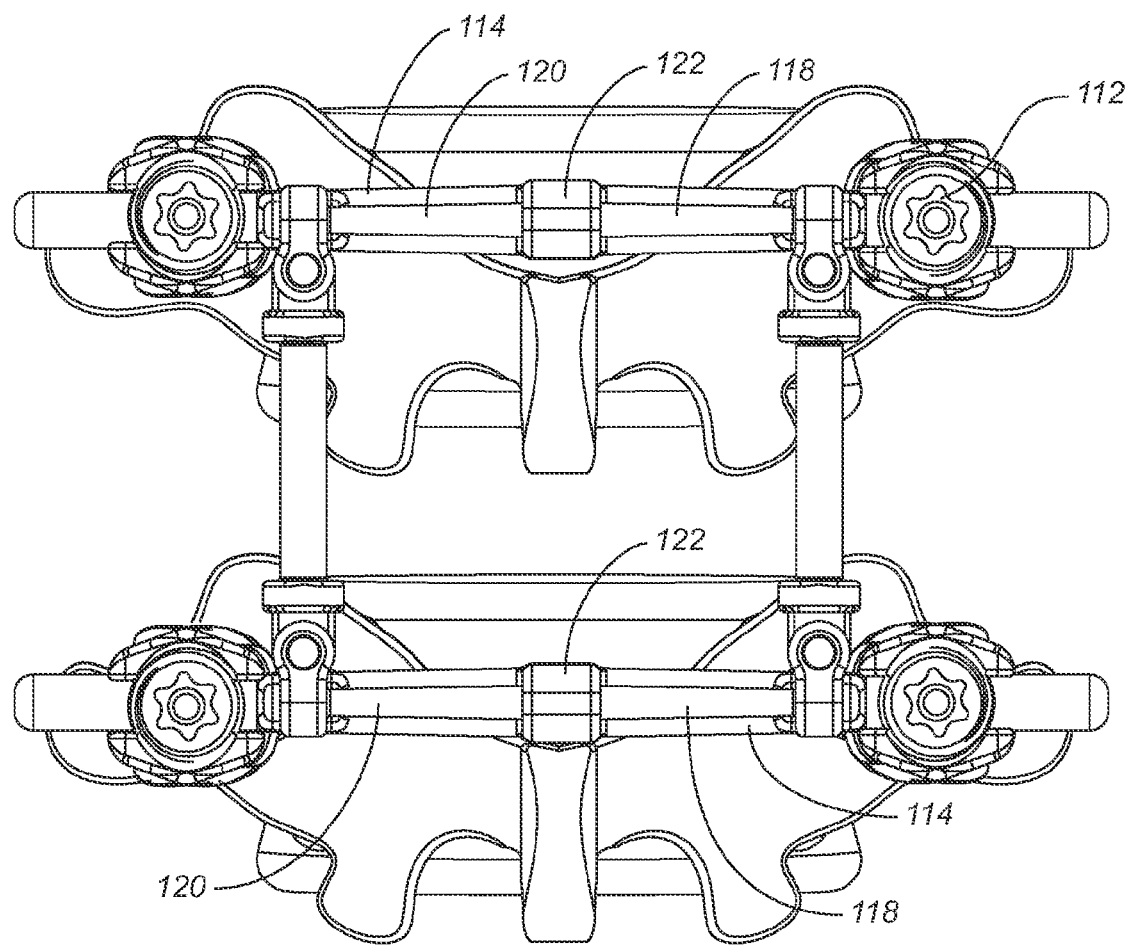
FIG. 43A is a side view of an alternative embodiment of a dynamic spine stabilization system of the invention.

As an alternate embodiment, the second horizontal rod 116 could be replaced with a horizontal rod 114 which has deflection rods or loading rods (FIG. 43A). Thus, both horizontal rods would have deflection rods or loading rods. The deflection rods or loading rods mounted on one horizontal rod would be connected to vertical rods and the vertical rods would be connected to deflection rods or loading rods mounted on the other horizontal rod. Such an embodiment provides for more flexibility. Further, the deflection rods or loading rods 118, 120 can have other configurations and be within the spirit and scope of the invention.

Further, as can be seen in FIG. 1, the vertical rod system is comprised of, in this embodiment, first and second vertical rods 132, 134 which are secured to first and second connectors 136, 138 located at the ends 128, 130 of the first and second deflection rods or loading rods 118, 120. As will be described below, the vertical rods 132, 134 are preferably connected in such a way as to be pivotal for purposes of implantation in a patient and for purposes of adding flexibility and dynamic stability to the system as a whole. These vertical rods 132, 134 are preferably made of titanium. However, other bio-compatible materials can be used. The vertical rods 132, 134 are also connected to the second horizontal rod 116 by being received in C-shaped mounts 140, 142 located on the second horizontal rods and in this embodiment, held in place by set screws 144,146. It is to be understood by one of ordinary skill in the art that other structures can be used to connect the vertical rods to the horizontal rods.

Preferably, the vertical rods are only connected to the horizontal rods and not to the anchoring system 102 in order to isolate the anchor system 102 and, in particular, the heads 110 from stress and forces that could be placed on the heads, and from forces transferred to the heads where the vertical rods connect to the heads. Thus, the system 100 through the vertical and horizontal rods allow for dynamic stability, and a wide range of motion without causing undue force to be placed on the heads of the anchor systems. These embodiments also allow for each level of the spine to move as freely as possible without being unduly restrictively tied to another level.

More lateral placement of the vertical rods toward the heads of the anchor system provides for more stiffness in lateral bending and an easier implant approach by, for example, a Wiltse approach as described in "The Paraspinal Sacraspinalis-Splitting Approach to the Lumber Spine," by Leon L. Wiltse et al., *The Journal of Bone & Joint Surgery*, Vol. 50-A, No. 5, July 1968, which is incorporated herein by reference.

The stiffness of the system 100 can preferably be adjusted by the selection of the materials and placement and diameters of the horizontal and vertical rods and also the deflection rods or loading rods. Larger diameter rods would increase the resistance of the system 100 to flexion, extension rotation, and bending of the spine, while smaller diameter rods would decrease the resistance of the system 100 to flexion, extension, rotation and bending of the spine. Further, continually or discretely changing the diameter of the rods such as the deflection rods or loading rods along the length of the rods changes the stiffness characteristics. Thus, with the deflection rods or loading rods 118, 120 tapered from the mount 122 toward the ends 128, 130, the system can have more flexibility in flexion and extension of the spine. Further, using a super elastic material for the horizontal rods and the vertical rods in addition to the horizontal deflection rods or loading rods adds to the flexibility of the system 100. Further, all of the horizontal and vertical rods, in addition to the deflection rods or loading rods, can be made of titanium or stainless steel or PEEK should a stiffer system 100 be required. Thus, it can be appreciated that the system 100 can easily accommodate the desired stiffness for the patient depending on the materials uses, and the diameter of the materials, and the placement of the elements of the system 100.

Should an implanted system 100 need to be revised, that can be accomplished by removing and replacing the horizontal and/or vertical rods to obtain the desired stiffness. By way of example only, should a stiffer revised system be desired, more akin to a fusion, or, in fact, a fusion, then the horizontal rods having the deflection rods or loading rods can be removed and replaced by horizontal rods having deflection rods or loading rods made of titanium, or stainless steel, or non-super elastic rods to increase the stiffness of the system. This can be accomplished by leaving the anchor system 102 in place and removing the existing horizontal rods from the heads 110 and replacing the horizontal rods with stiffer horizontal rods and associated vertical rods.

FIG. 3 depicts a view of the horizontal rod 104 as previously described. In this embodiment the connectors 136, 138 are shown on the ends of the deflection rods or loading rods 118, 120. The connectors can be forced-fitted to the deflection rods or fastened in other methods known in the art for this material and as further disclosed below. The connectors 136, 138 have slits 148, 150 to aid in placing the connectors onto the ends of the deflection rods. As is evident from FIG. 3, the connectors 136, 138 each include upper and lower arms 160, 162 which can capture there between the vertical rods 132, 134. The arms each include an aperture 168, 170 that can accept a pin or screw 176, 178 (FIG. 1) for either fixedly or pivotally securing the vertical rods 132, 134. In this embodiment the vertical rods include a head 162, 164 that can be force fit or screwed onto the rest of the vertical rods. The heads include apertures 172, 174 for accepting the pins or screws 176, 178.

In order that the system 100 has as low a profile as possible and extends from the spine as little as possible, it is advantageous to place the deflection rods or loading rods 118, 120 as close to the first horizontal rod 114 as possible. In order to accomplish this low profile, preferably notches 152, 154 are placed in horizontal rod 114 to accommodate the connectors 136, 138.

Accordingly, the purpose for the notches is to provide for a horizontal rod with a low profile when implanted relative to the bones and tissues of the spine so that there is, for example, clearance for implant and the motion of the implant, and to keep the deflection rods or loading rods as close as possible to the horizontal rods in order to reduce any potential moment arm relative to the mounts on the horizontal rod.

Figure 46:
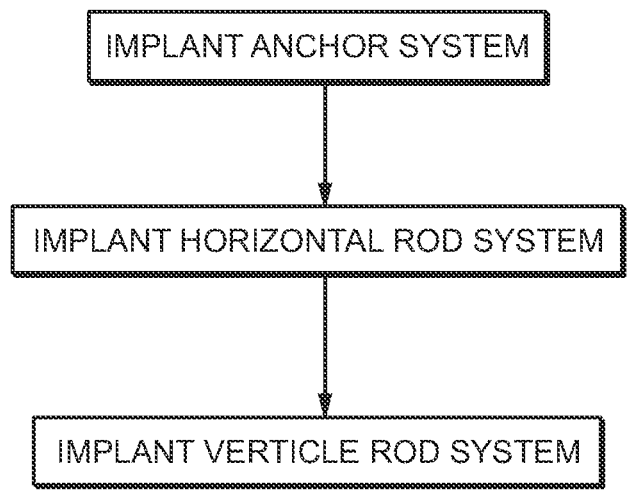
FIG. 46 is a flow chart of an embodiment of the method of the invention.

FIG. 4 depicts another embodiment of the horizontal rod 114 with deflection rods or loading rods 118, 120 and with difference connectors 156, 158. Connectors 156, 158 each include two pairs of upper and lower arms 160, 162 extending in opposite directions in order for each connector 156, 158 to mount an upper and a lower vertical rod as presented with respect to FIG. 46. This configuration allows for a three level system as will be described below.

Embodiments of the Anchor System of the Invention

Figure 5:
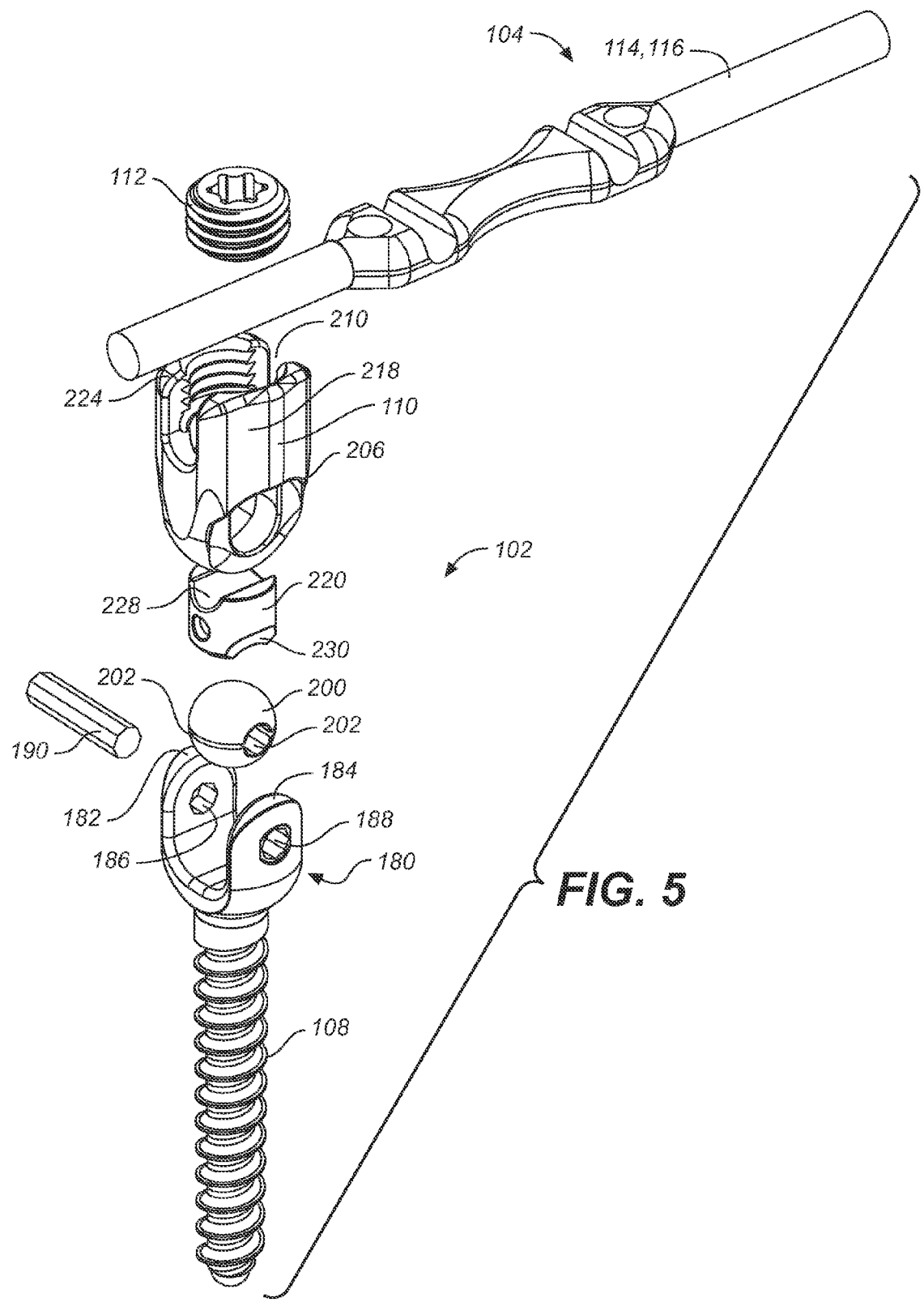
FIG. 5 is a perspective view of an embodiment of an anchor system of the invention for use with a dynamic spine stabilization system such as depicted in FIG. 1.
Figure 7:
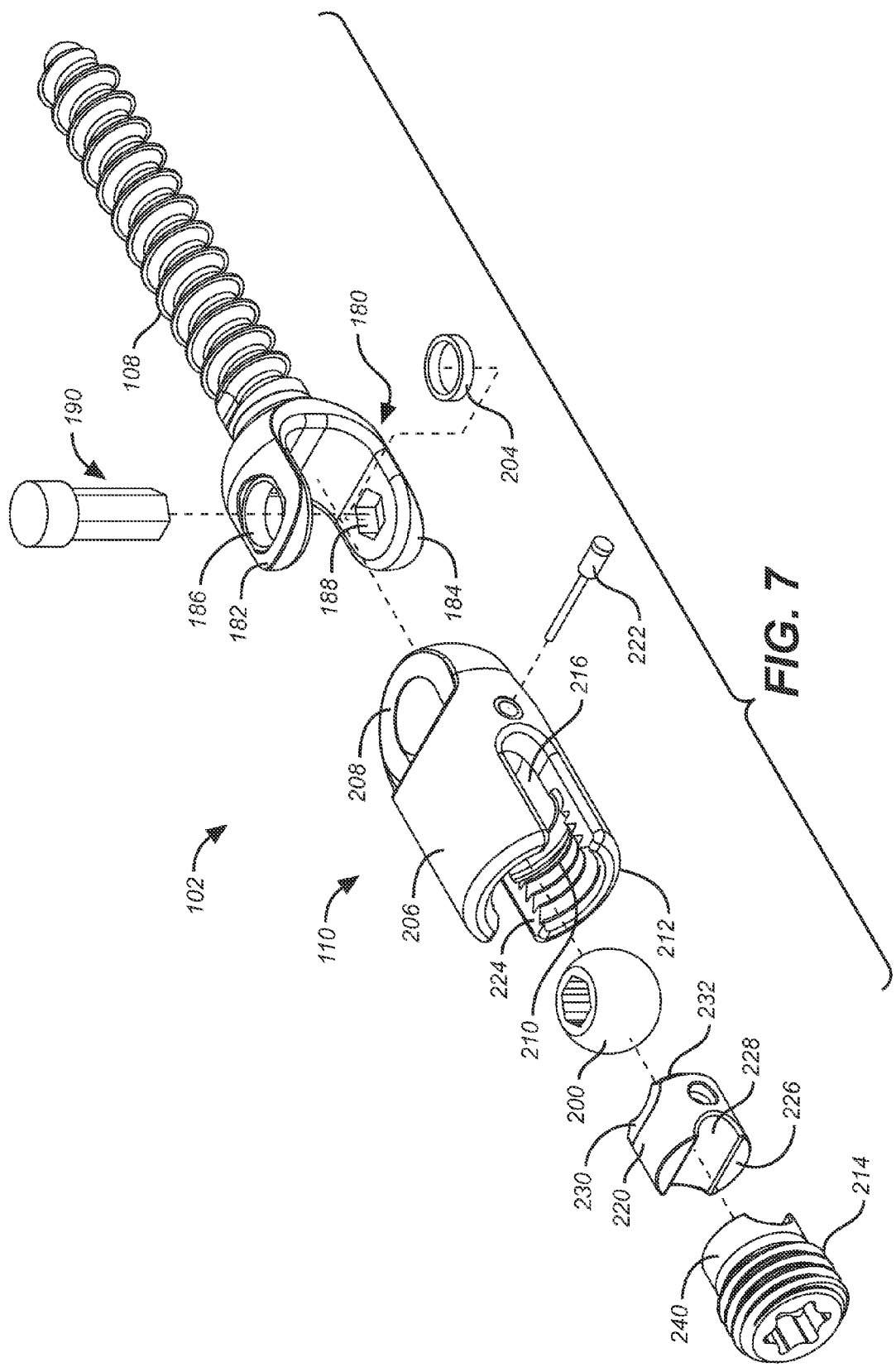
FIG. 7 is an exploded perspective view of an alternative embodiment of the anchor system of the invention for use with a dynamic spine stabilization system such as depicted in FIG. 1.

A preferred embodiment of the anchor system 102 invention can be seen in FIG. 5. This is similar to the anchor system 102 depicted in FIG. 1. In particular, this anchor system 102 includes a bone screw 108 with a head 110 in the form of a U-shaped yoke 180 with arms 182, 184. As will be discussed further, a hook, preferably with bone engaging barbs or projections, can be substituted for the bone screw 108. The hook embodiment is further described in the above referenced and incorporated provisional application. The hooks are used to hook to the bone, such as the vertebra instead of having screws anchored into the bone. Each of the arms 182, 814 of yoke 180 includes an aperture 186, 188 through which a pin 190 can be placed. The pin 190 can be laser welded or force fit or glued into the yoke 180, as desired. The pin 190 can be smooth or roughened as discussed below. Further, the pin 190 can be cylindrical or be comprised of a multiple sides as shown in FIG. 7. In FIG. 7, pin 190 has six sides and one or more of the accommodating apertures 186, 188 can also include mating sides in order to fix the position of the pin 190 in the yoke 180. A compression sphere 200 is placed over the pin 190. The compression sphere 200 can have a roughened surface if desired to assist in locking the sphere in place as described below. The compression sphere 200 can include one or more slits 202 to assist in compressing the sphere 200 about the pin 190. The compression sphere 200 can have an inner bore that is cylindrical or with multiple sides in order conform to and be received over the pin 190. As can be seen in FIG. 8, one or more spacer rings 204 can be used to space the compression ring from the yoke 180 in order to assist in providing the range of motion and degrees of freedom that are advantageous to the embodiments of the invention.

Mounted about the compression sphere 200 is the head or saddle 110. Head 110 in FIGS. 7, 8 is somewhat different from head 110 in FIG. 1 as will be described below. Head 110 in FIGS. 7, 8 includes a cylindrical body 206 with a lower end having an aperture 208 that can receive the compression sphere 200. The aperture 208 can have a concave surface as depicted in FIGS. 7, 8. Accordingly, the compression sphere 200 fits inside of the concave surface of aperture 208 and is free to move therein until restrained as described below. As is evident from the figures, the lower end of the cylindrical body 206 about the aperture 208 has some of the material that comprised wall 224 removed in order to accommodate the motion of the yoke 180 of the bone screw 108. Essentially, the portion of the wall 224 adjacent to the arms 182, 184 of the yoke 180 has been removed to accommodate the yoke 180 and the range of motion of the yoke.

The head 110 of the anchor system 102 includes an internal cylindrical bore 210 which is preferably substantially parallel to a longitudinal axis of the head 110. This bore 210 is open to the aperture 208 and is open and preferably substantially perpendicular to the distal end 212 of the head 110. At the distal end 212 of the head 110, the bore 210 is threaded and can accept the set screw 112. Along the side of the head 110 are defined aligned U-shaped slots that extend through the head 110 from the outer surface to the bore 210. These U-shaped slots are also open to the distal end 212 of the head 110 in order to have the set screw 112 accepted by the threads of the bore 210. Located in the bore 210 between the set screw 112 and the compression sphere 200 is a compressor element or cradle 220. The compressor element or cradle 220 can slide somewhat in the bore 210, but the compressor element or cradle 220 is restrained by a pin 222 (FIG. 7) received through the wall 224 of the head 110 and into the compressor element or cradle 220. Thus, the compressor element or cradle 220, until locked into position, can move somewhat in the bore 210.

The compressor element or cradle 220 has a generally cylindrical body so that the compressor element 220 can fit into bore 210. An upper end 226 of the compressor element 220 includes a concave surface 228. This surface 228 is shaped to fit the horizontal rod system 104 and, in particular, a horizontal rod 114, 116. The lower end of the compressor element 220 includes a concave surface 230 which can accommodate the compression sphere 200. The lower end of the compressor element 220 adjacent to the concave surface 230 has an additional concave surface 232 (FIG. 8) which is used to accommodate the motion of the upper end of the yoke 180 as the head 110 is moved relative to the bone screw 108. The concave surfaces 228 and 230 can be roughened, if desired, to assist in locking the head 110 relative to the bone screw 108. In this embodiment (FIGS. 5, 6) there is no top compression element or cradle (see, for example, FIGS. 7, 13) in order to reduce the profile of the head of the anchor system.

As is evident from the figures, with the anchor system 102 assembled and with a horizontal rod 114, 116 received in the U-shaped slot 216, the set screw can press against the horizontal rod 114, 116, which horizontal rod 114, 116, can press against the compressor element or cradle 220, which compressor element or cradle 220 can press against the compression sphere 220, which compression sphere can press against the pin 190 in order to lock the horizontal rod 114, 116 relative to the head 110 and to lock the head 110 relative to the bone screw 108. It is to be understood that all of the surfaces that are in contact, can be roughened to enable this locking, if desired. Alternatively, the surfaces may be smooth with the force of the set screw 112 urging of the elements together and the resultant locking.

Figure 6:
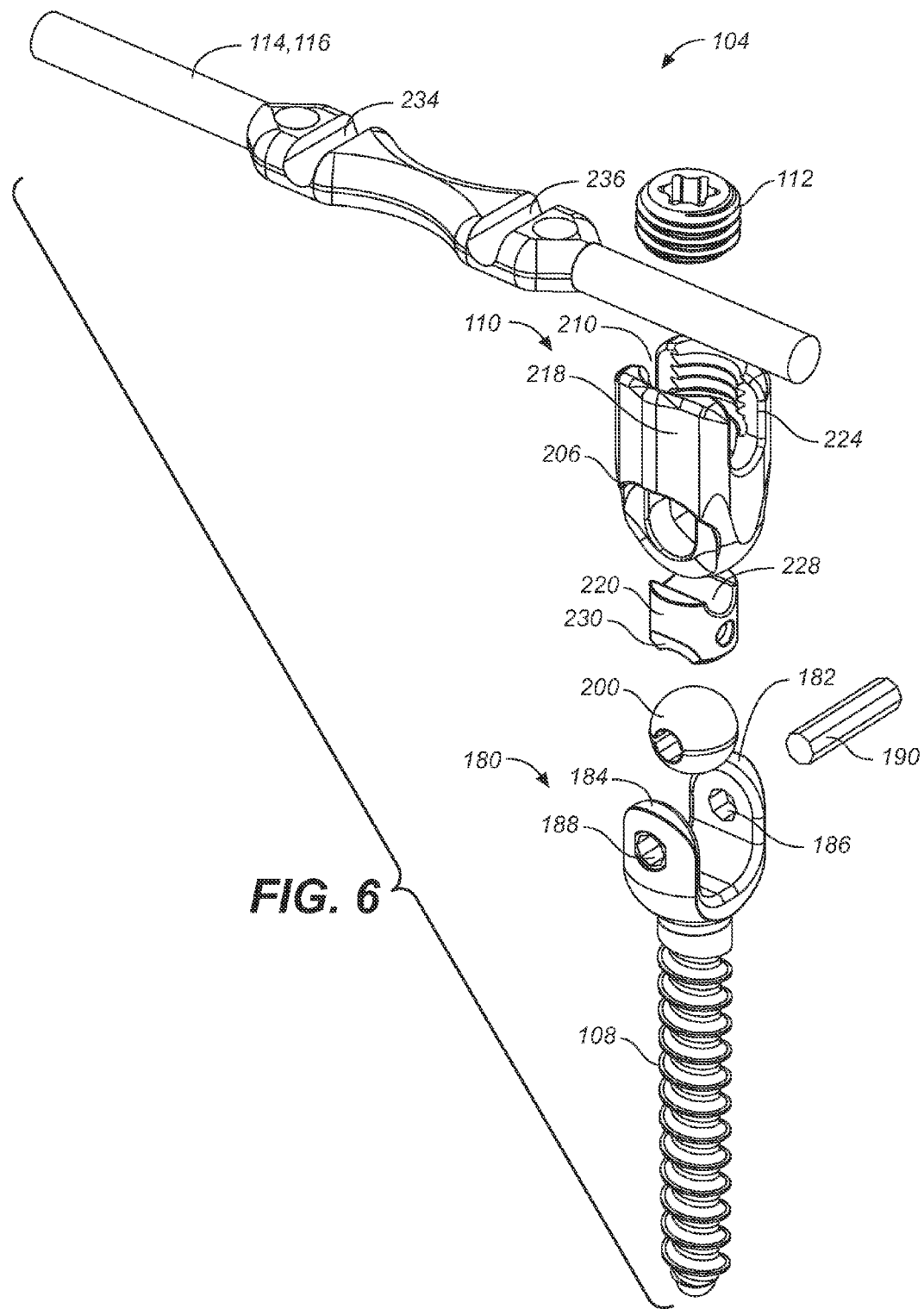
FIG. 6 is a another perspective view of the embodiment of the anchor system of FIG. 5.
Figure 34:
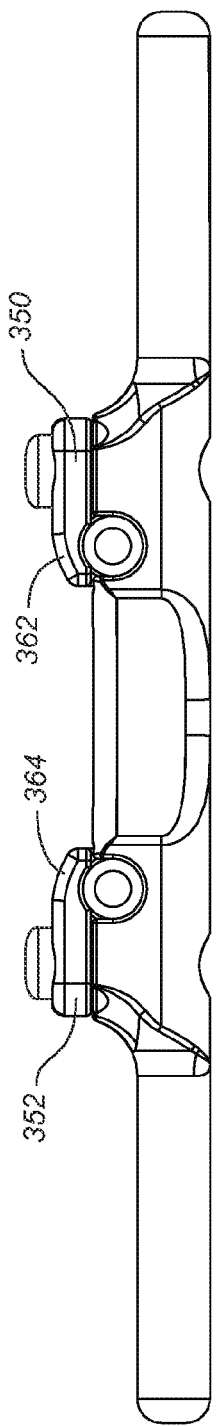
FIG. 34 is a side view of another alternative embodiment of the horizontal rod system of the invention.

As can be seen in FIGS. 5, 6 an alternative horizontal rod 114, 116 is depicted. This alternative horizontal rod 114, 116 includes first and second concave openings 234, 236 which can receive vertical rods such as vertical rods 132, 134 (FIG. 1). The horizontal rod 114, 116 is substantially cylindrical with the areas around the concave openings 234, 236 bulked up or reinforced as desired to support the forces. Additionally, threaded bores are provided adjacent to the concave openings 234, 236 and these bores can receive screws that have heads that can be used to lock vertical rods in place. Alternatively, the screws can retain short bars that project over the concave openings 234, 236 in order to hold the vertical rods in place (FIG. 34). If desired, the short retaining bars can also have concave openings that conform to the shape of, and receive at least part of, the vertical rods in order to retain the vertical rods in place with the system 100 implanted in a patient.

Turning again to FIGS. 1, 2, 5, 6, the head 110 depicted is a preferred embodiment and is somewhat different from the head 110 as seen in FIG. 8. In particular the head body 206, the outer surface 218 of the head and the head wall 224, have been configured in order to prevent splaying of the head 110 when the set screw 112 locks the anchor system 102 as explained above. As seen in FIGS. 1, 2, the head 110 and, in particular, the wall 224 is reinforced about the U-shaped slot 216 that received the horizontal bar system 104. By reinforcing or bulking up the area of the wall about the U-shaped slot 216, splaying of the head 110 when force is applied to the set screw 214, in order to lock the anchor system 102, is avoided. The head 110 can use a number of shapes to be reinforced in order to prevent splaying. The exemplary embodiment of FIGS. 1, 2, includes a pitched roof shape as seen in the top view looking down on distal end 212 of the head 110. In particular, the wall about the U-shaped slot 216 is thickened, while the portion of the head distal from the U-shaped slot can be less thick if desired in order to reduce the bulk and size of the head 110 and, thus, give the head 110 a smaller profile relative to the bone and tissue structures when implanted in a patient. Further, the small profile allows greater freedom of motion of the system 100 as described below. Also, it is to be understood that due to the design of the anchor system 102, as described above, the head 110 can be shorter and, thus, stand less prominently out of the bone when the bone screw 108 in implanted in a spine of a patient for example.

Freedom of Motion of the Embodiments of the Anchor System of the Invention

In order to accommodate embodiments of the horizontal rod systems 104 of the invention, to allow greater freedom in placing the horizontal rod systems and the anchor systems 102 relative to, for example, the spine of a patient, and to provide for a smaller implanted profile in a patient, the anchor system 102 includes a number of degrees of freedom of motion. These degrees of freedom of motion are depicted in FIGS. 9, 9A, 10, 10A, and 11, 11A.

Figure 9A:
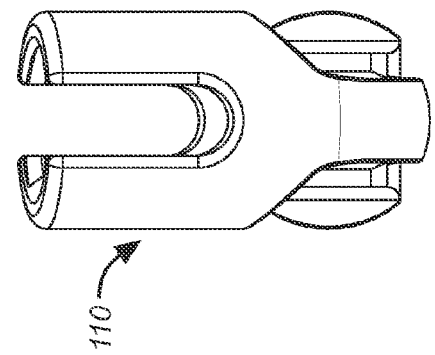
FIG. 9A is an end view of the anchor system of FIG. 9.
Figure 10A:
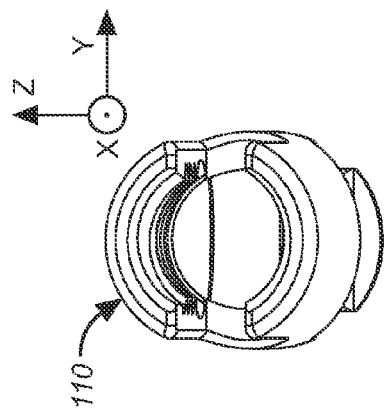
FIG. 10A is an end view of the anchor system of FIG. 10.
Figure 9:
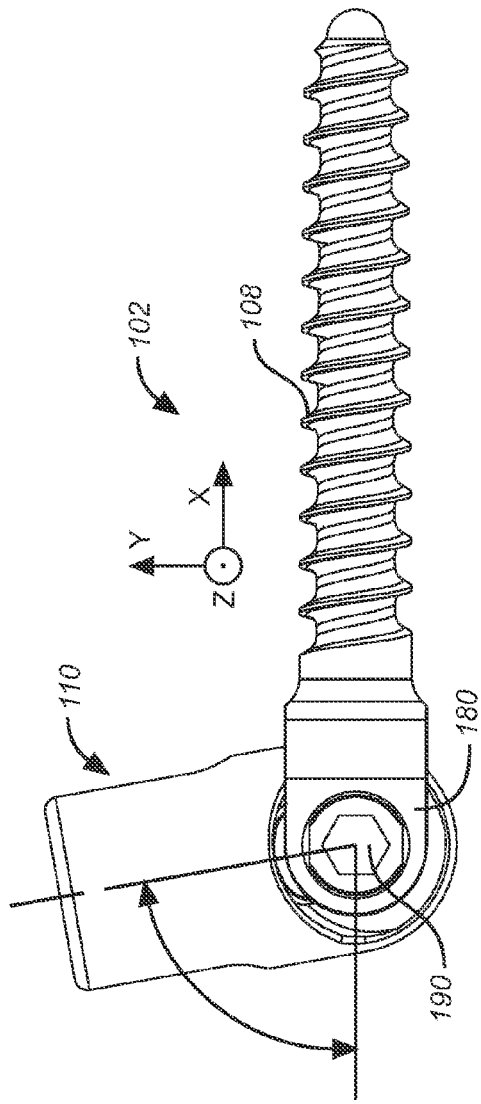
FIG. 9 is a side view of the anchor system of FIG. 7 depicting a degree of freedom of movement of the anchor system of FIG. 7.
Figure 10:
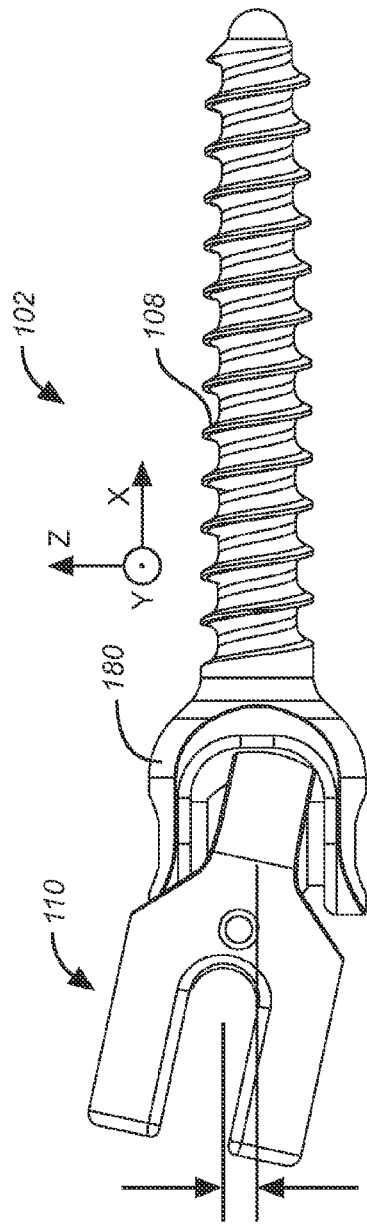
FIG. 10 is a side view of the anchor system of FIG. 7 depicting another degree of freedom of movement of the anchor system of FIG. 7.

FIG. 9 establishes a frame of reference including a longitudinal axis x which is along the longitudinal length of the bone screw 108, a y axis that extends perpendicular to the x axis, and a lateral axis z which is perpendicular to both the x axis and the y axis and extends outwardly from and parallel to the pin 190 of the yoke 180 of the anchor system 102. As depicted in the figures and, in particular, FIGS. 9, 9A, the system 100 due to the embodiments as disclosed herein is able to have the head 110 rotate about the z axis from about 80 degrees to about zero degrees and, thus, in line with the x axis and from the zero degree position to about 80 degrees on the other side of the x axis. Accordingly, the head is able to rotate about 160 degrees about the z axis relative to the bone screw 108. As seen in FIGS. 10, 10A the head 110 is able to tilt about 0.08 inches (2 mm) relative to and on both sides of the x axis. Accordingly, the head 110 can tilt from about 12 degrees to zero degrees where the head 110 is about parallel to the x axis and from zero degrees to 12 degrees about the y axis and on the other side of the x axis. Thus, the head can tilt through about 24 degrees about the y axis. As can be seen in FIGS. 11, 11A, the head 110 can swivel for a total of about 40 degrees about the x axis. With respect FIG. 11A, the head 110 can swivel about the x axis from about 20 degrees to one side of the z axis to zero degrees and from zero degrees to about 20 degrees on the other side of the z axis. The head is able to substantially exercise all of these degrees of freedom at once and, thus, can have a compound position relative to the bone screw by simultaneously moving the head within the ranges of about 160 degrees about the z axis (FIG. 9), about 24 degrees from the y axis (FIG. 10) and about 40 degrees about the x axis (FIG. 11A).

Thus, with respect to FIGS. 9, 9A the range of motion in the axial plane is about 180 degrees or about 90 degrees on each side of the centerline. In FIGS. 10, 10A the range of motion in the Caudal/Cephalad orientation is about 4 mm or about 2 mm on each side of the centerline or about 24 degrees or about 12 degrees on each side of the centerline. In FIGS. 11, 11A the range of motion in the coronal plane is about 40 degrees or about 20 degrees on each side of the centerline.

Figure 13:
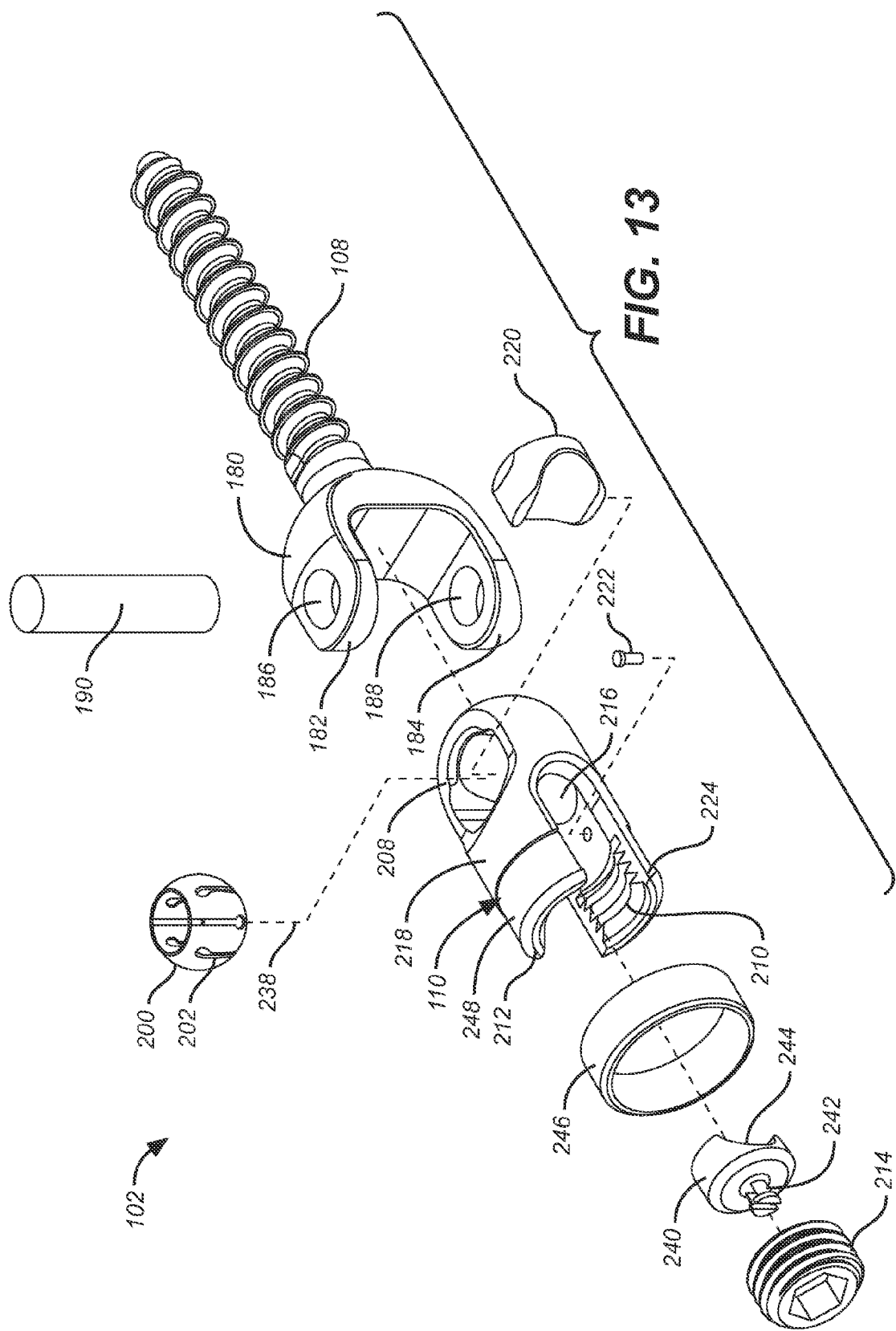
FIG. 13 is an exploded perspective view of the embodiment of the anchor system of the invention of FIG. 12.

FIGS. 12, 13 depict yet another embodiment of the anchor system 102 of the invention where elements that are similar to elements of other embodiments and have similar reference numbers.

As can be seen in FIG. 13, this embodiment includes a lower cradle or compressor element 220 that is similar to the cradle or compressor element 220 of the embodiment of FIG. 7 with the head 110 similar to the head 110 as seen in FIG. 7. The compression sphere 200 is similar to the compression sphere 200 in FIG. 7 with the compression sphere including a plurality of slits provided about the axis of rotation 238 of the sphere 200. In this embodiment, the slits 202 have openings that alternate between facing the north pole of the axis of rotation of the sphere 200 and facing the south pole of the axis of rotation of the sphere 200. Alternatively, the slits can be provided in the sphere and have no opening relative to the north or south pole of the axis of rotation of the sphere 200. Still further, the slits can open relative to only one of the north or south poles.

In the embodiment of FIGS. 12, 13, there is also an upper cradle or compressor element 240 which is positioned adjacent to the set screw 214 (see also FIG. 7). The upper cradle or compressor element 240 has a generally cylindrical body which can slide in the cylindrical bore of the head 110 with an upper end having fingers 242 extending therefrom. The fingers 242 can spring over a bore formed in the lower surface of the set screw 214 in order to retain the cradle 240 relative to the set screw 214 and to allow the cradle 240 to rotate relative to the set screw 214. The lower surface of the cradle 240 includes a concave surface 244 which can mate with a horizontal rod 114, 116 in order to lock the rod relative the head 110 and the head 110 relative to the bone screw 108. If desired, the concave surface 244 can be roughened to assist in locking the system 100.

Further, in FIGS. 12, 13, a retaining ring 246 is depicted. The retaining ring can be force fit over the outer surface 218 of the head 110, or pop over and snap under a ridge 248 at the distal end 212 of the head 110, or can have internal threads that mate with external threads located on the outer surface of the 218 of the head 110. With the anchor system 102 in place in a patient and with the horizontal rod 114, 116 received in the anchor system, before the set screw 214 is tightened in order to lock the horizontal rod and the anchor system, the retaining ring 246 can be attached to the head 110 in order to prevent splaying of the head 110 as the set screw 214 locks the system 110.

Figure 14:
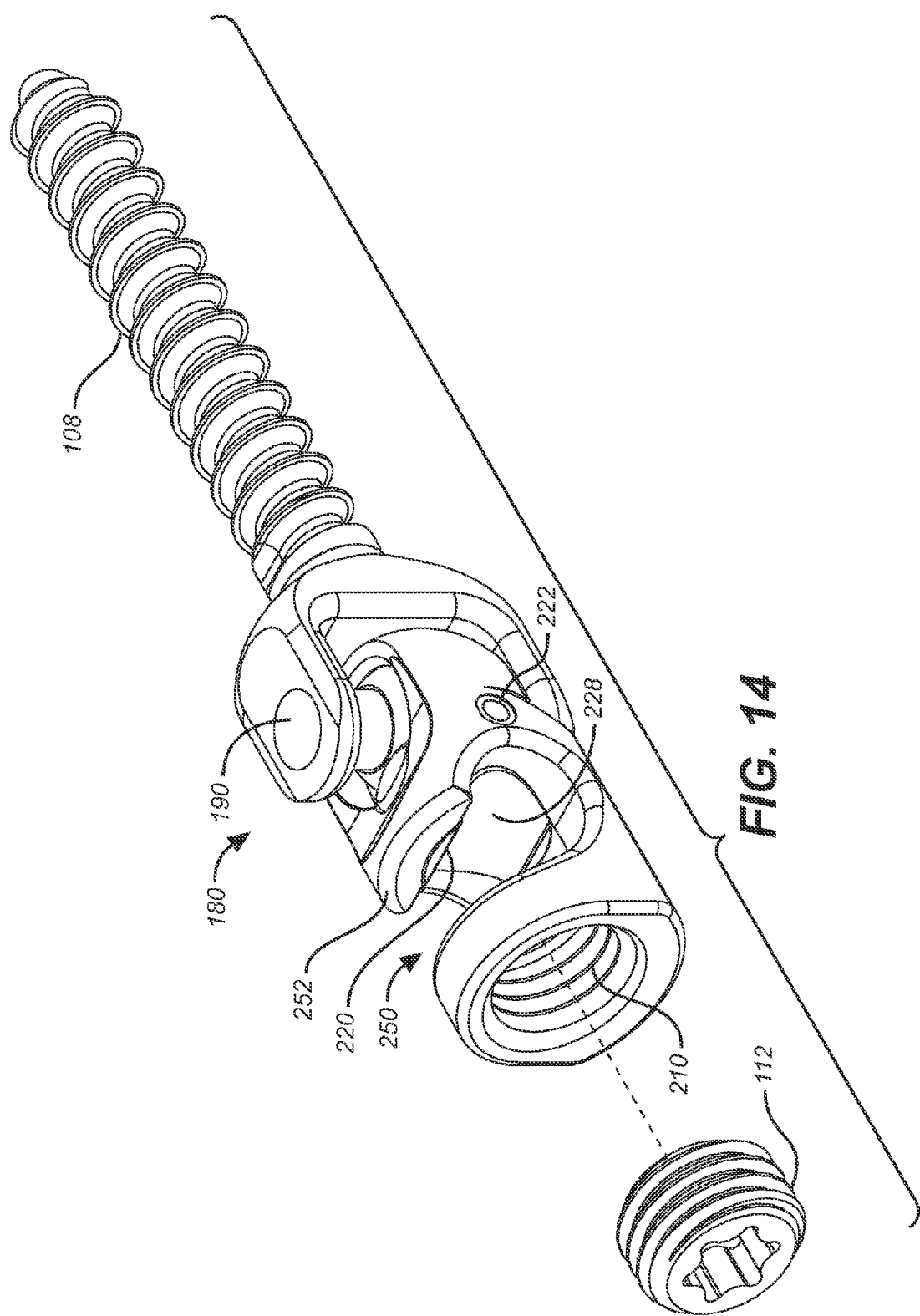
FIG. 14 is a perspective view of yet another embodiment of the anchor system of the invention.
Figure 15:
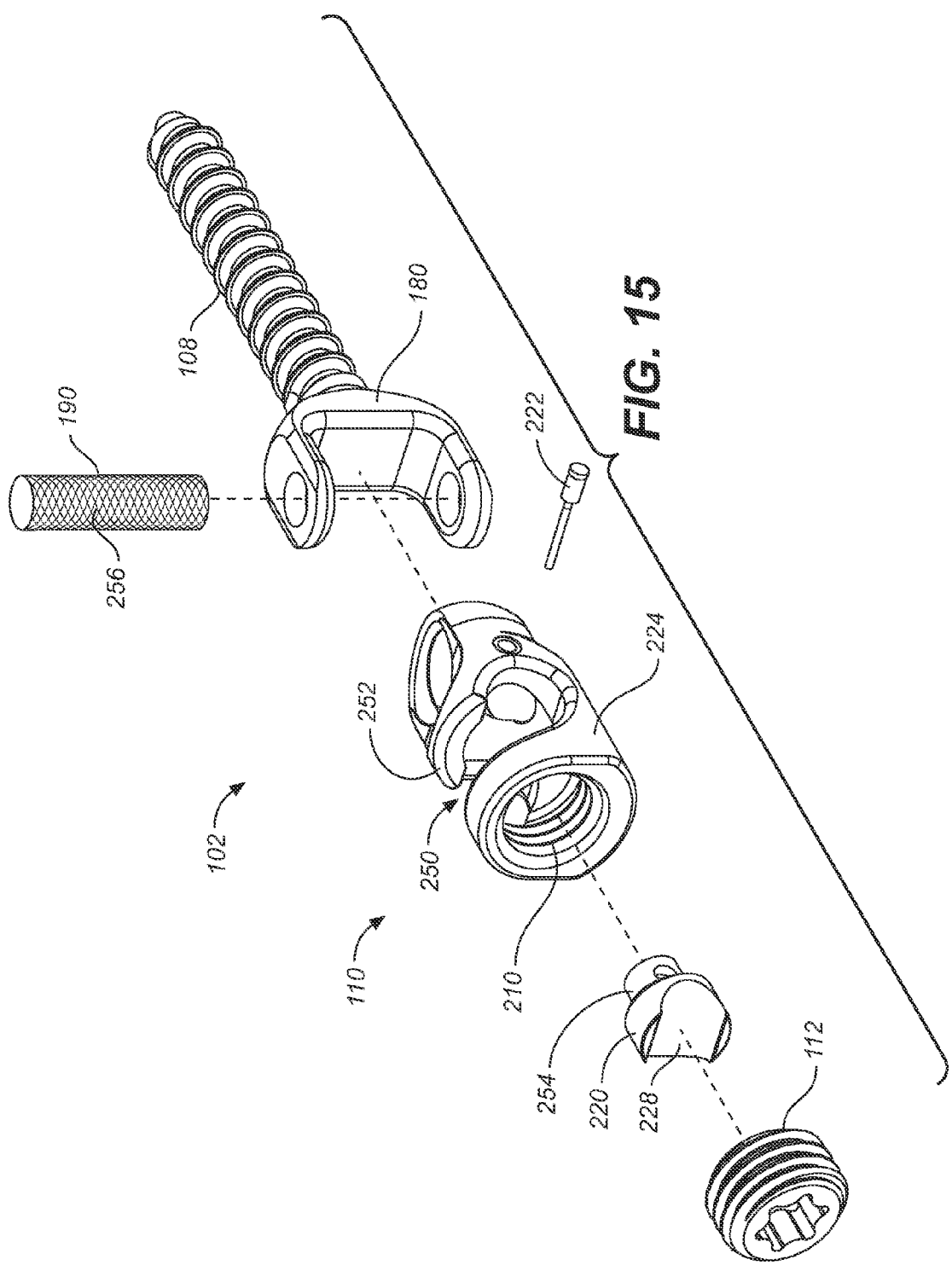
FIG. 15 is an exploded perspective view of the embodiment of the anchor system of the invention of FIG. 14.
Figure 16:
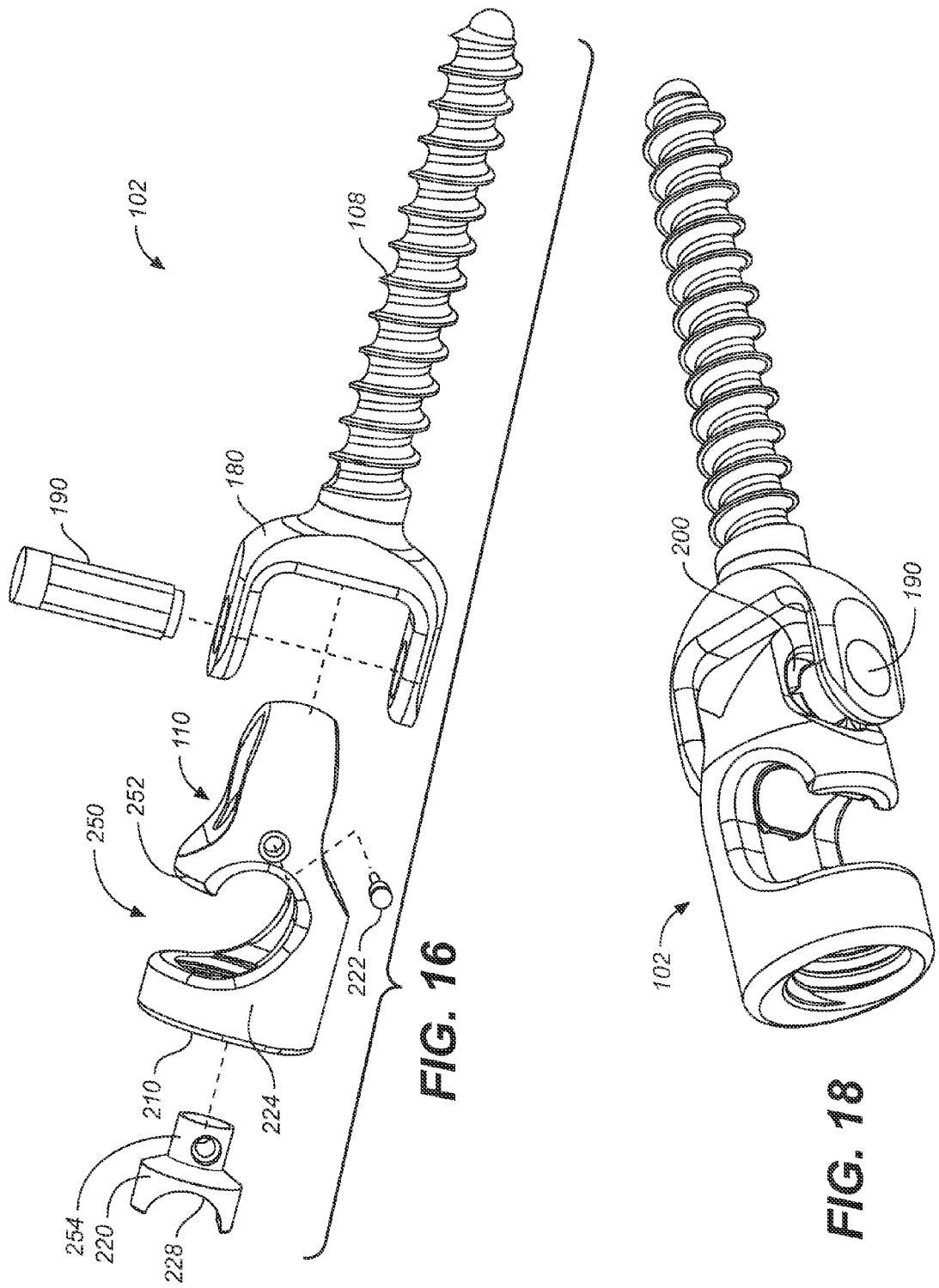
FIG. 16 is another exploded perspective view of the embodiment of the anchor system of the invention of FIG. 14.

Further embodiments of the anchor system 102 which can side load the horizontal rods 114, 116 are seen in FIGS. 14, 15, and 16, where similar elements from other embodiments of the anchor system are given similar numeral references. With respect to the embodiment in FIG. 15, the head side wall 224 includes a lateral or side opening 250 which communicates with the cylindrical bore 210 which is located in head 110. The lateral or side opening preferably extends more than 180 degrees about the outer surface of the head. The side opening 250 includes a lip 252 and the side opening extends down below the lip into communication with the cylindrical bore 210 and follows the outline of the concave surface 228 of the cradle 220. Accordingly, a horizontal rod 114, 116, can be positioned through the side opening 250 and urged downwardly into contact with the concave surface 228 of the cradle 220. In this embodiment the cradle 220 includes a downward projecting post 254. Also, this embodiment does not include a compression sphere, and instead the pin 190, which can have a larger diameter than a pin 190 in other embodiments, comes in direct contact with the post 254 when the set screw 112 locks the anchor system 100. If desired the pin 190 can have a roughened surface 256 to assist in the locking of the anchor system 100. As is evident from FIGS. 14, 15, 16, as this embodiment has a side loading head 110, the distal end of the head is a fully cylindrical without communicating with any lateral U-shaped slots of the other embodiments. Accordingly, this embodiment does not include any retaining ring or reinforced areas that can be used to prevent splaying.

Figure 17:
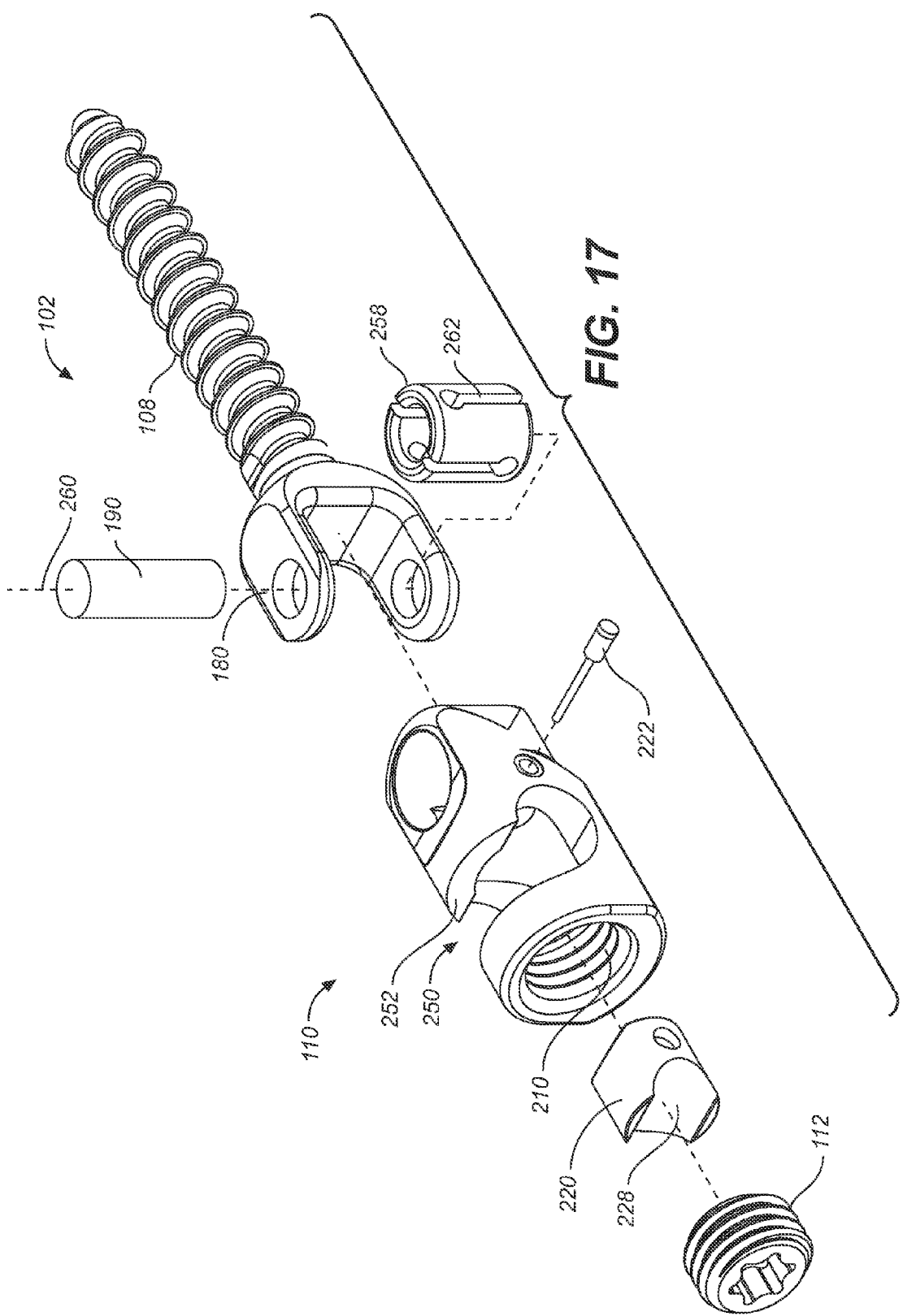
FIG. 17 is an exploded perspective view of another embodiment of the anchor system of the invention.

FIG. 17 depicts yet another embodiment of the anchor system 102 that has a lateral or side loading head 110. In this embodiment, a compression cylinder 258 is placed over the pin 190. Such a compression cylinder 258 may offer less freedom of motion of the anchor system 100 with added stability. The compression cylinder 258 can slide along the longitudinal axis 260 of the pin 190, if desired. The head 110 can rotate about the pin 190 and the compression cylinder 258. The head 110 can also slide or translate along the longitudinal axis 260 of the pin as well as the longitudinal axis of the compression cylinder 258. Compression cylinder 258 has slits 262 that can be configured similarly as the slits 202 of the other embodiments of the anchor system 100 described and depicted herein.

FIG. 18 depicts still another embodiment of the anchor system 100 that has a lateral or side loading head 110. This embodiment includes a compression sphere 200 provided over a pin 190 which is similar to the other compression spheres 200 depicted and described herein. Accordingly, this embodiment has the freedom of motion described with respect to the other embodiments which use a compression sphere.

It is to be understood that although each embodiment of the anchor system does not necessarily depict all the elements of another embodiment of the anchor system, that one of ordinary skill in the art would be able to use elements of one embodiment of the anchor system in another embodiment of the anchor system.

Embodiments of the Horizontal Rod System of the Invention

Embodiments of the horizontal rod system 104 of the invention include the embodiments describes above, in addition to the embodiments that follow. An aspect of the horizontal rod system 104 is to isolate the anchor system 102 and reduce the stress and forces on the anchor system. This aspect is accomplished by not transmitting such stresses and forces placed on the horizontal rod system by, for example, flexion, extension, rotation or bending of the spine to the anchor system. This aspect thus maintains the integrity of the placement of the anchor system in, for example, the spine and prevents loosening of the bone screw or bone hook of the anchor system. In addition, various horizontal rod systems can be used to control the rigidity, stiffness and/or springiness of the dynamic stabilization system 100 by the various elements that comprise the horizontal rod system. Further the horizontal rod system can be used to have one level of rigidity, stiffness and/or springiness in one direction and another level in a different direction. For example, the horizontal rod system can offer one level of stiffness in flexion of the spine and a different level of stiffness in extension of the spine. Additionally, the resistance to lateral bending can be controlled by the horizontal rod system. Select horizontal rod systems allow for more resistance to lateral bending with other select horizontal rod systems allow for less lateral bending. As discussed below, placement of the vertical rods also effects lateral bending. The more laterally the vertical rods are placed, the more stiff the embodiment is to lateral bending.

As is evident from the figures, the horizontal rod system connects to the heads of the anchor system without the vertical rod system connecting to the heads. Generally, two anchor systems are secured to each vertebral level with a horizontal rod system connected between the two anchor systems. This further ensures that less stress and force is placed on the anchor systems secured to each level and also enables dynamic stability of the vertebra of the spine. Accordingly, movement of the vertebra relative to each other vertebra, as the spine extends, flexes, rotates and bends, is stabilized by the horizontal rods and the entire system 100 without placing excessive force or stress on the anchor system as there are no vertical rods that connect the anchor systems of one vertebra level with the anchor system of another vertebra.

Figure 19:
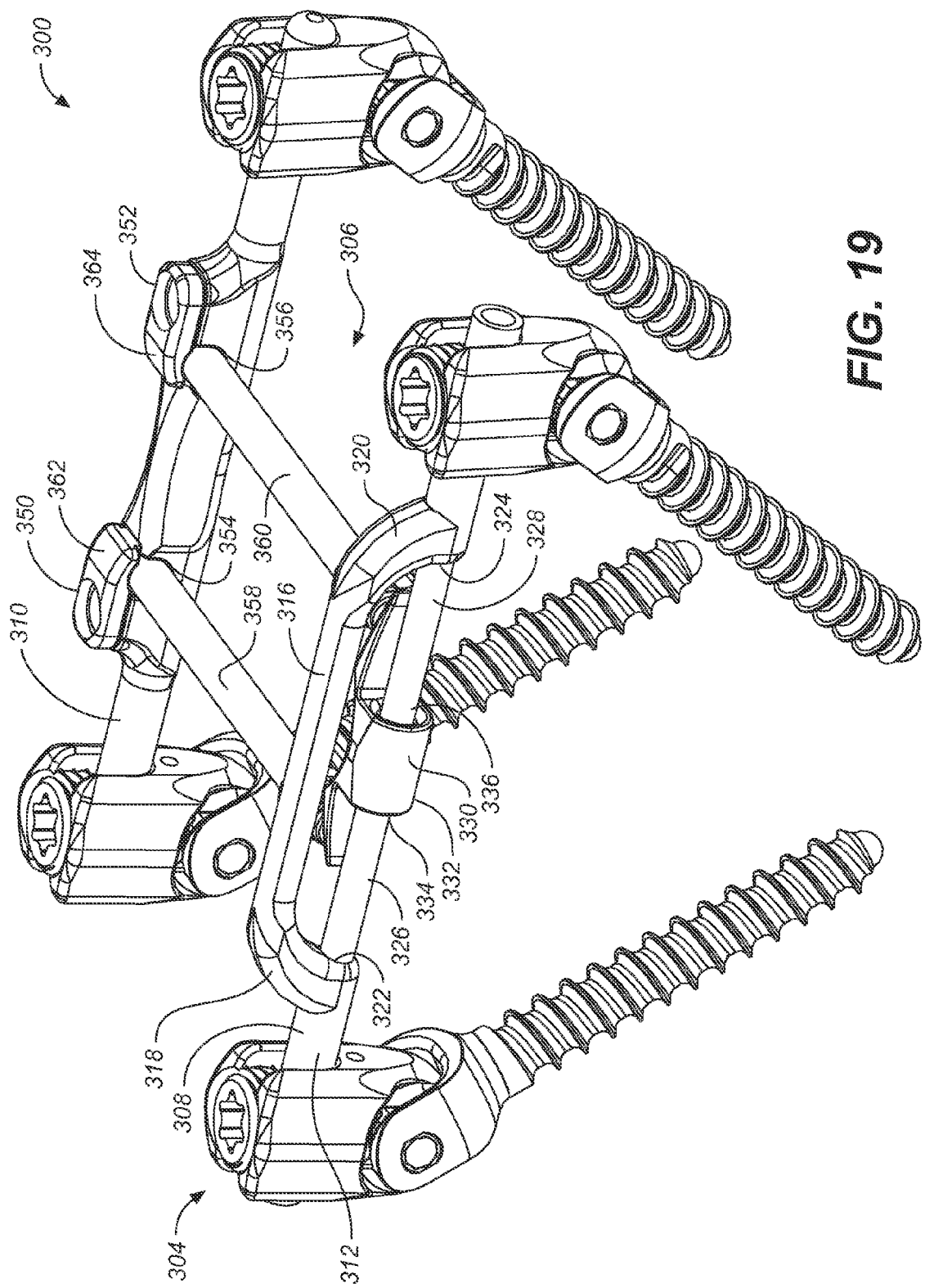
FIG. 19 is a perspective view of another embodiment of a dynamic spine stabilization system of the invention with another horizontal rod system.
Figure 19B:
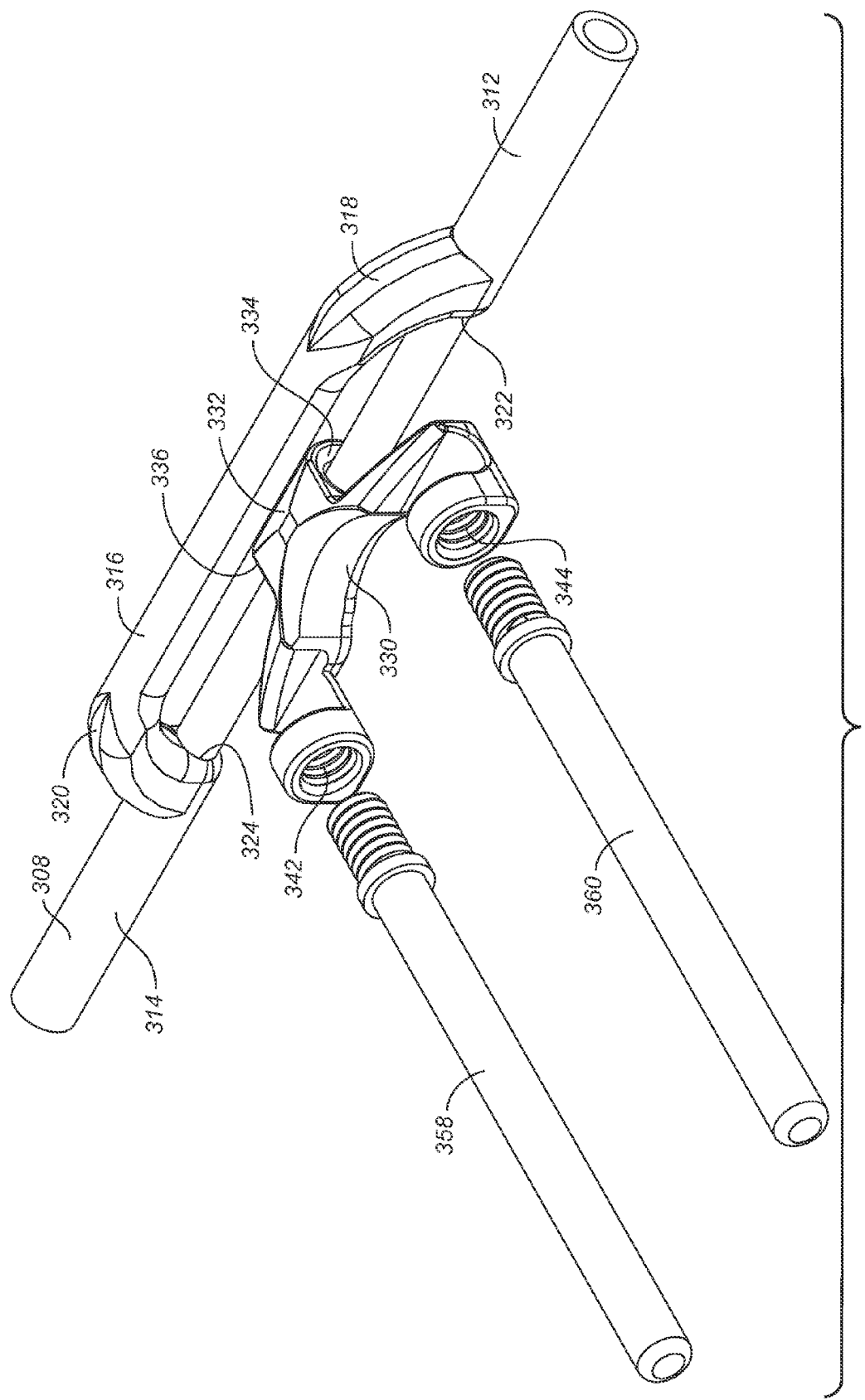
FIG. 19B is an exploded perspective view of the embodiment of FIG. 19.
Figure 20:
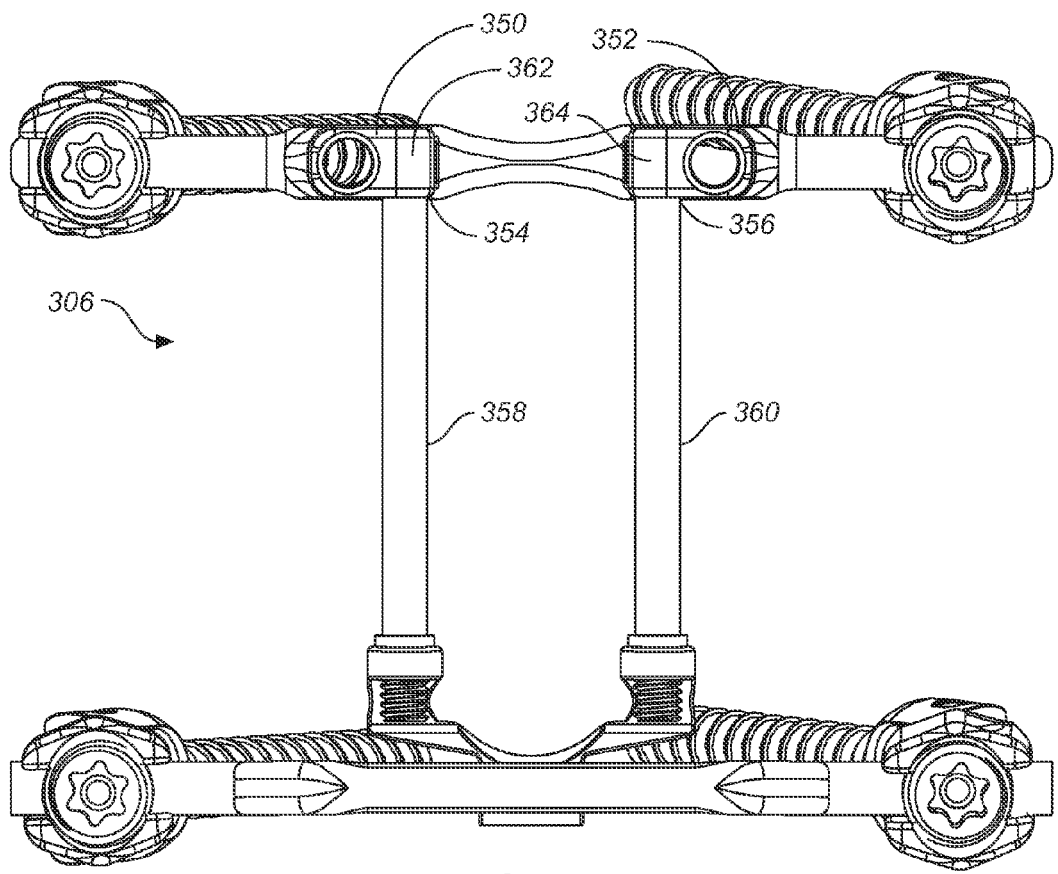
FIG. 20 is a top view of the another embodiment of the dynamic spine stabilization of the system of the invention of FIG. 19.
Figure 20A:
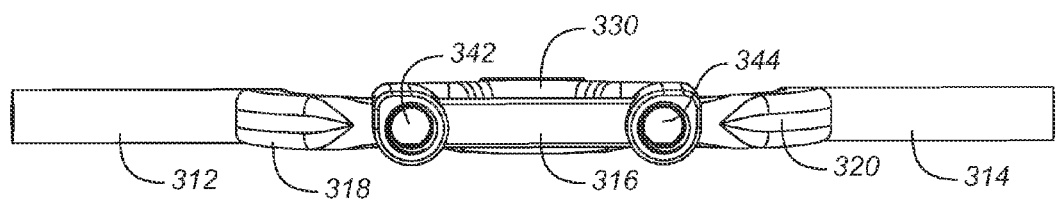
FIG. 20A is a top side of the embodiment depicted in FIG. 19A.
Figure 21:
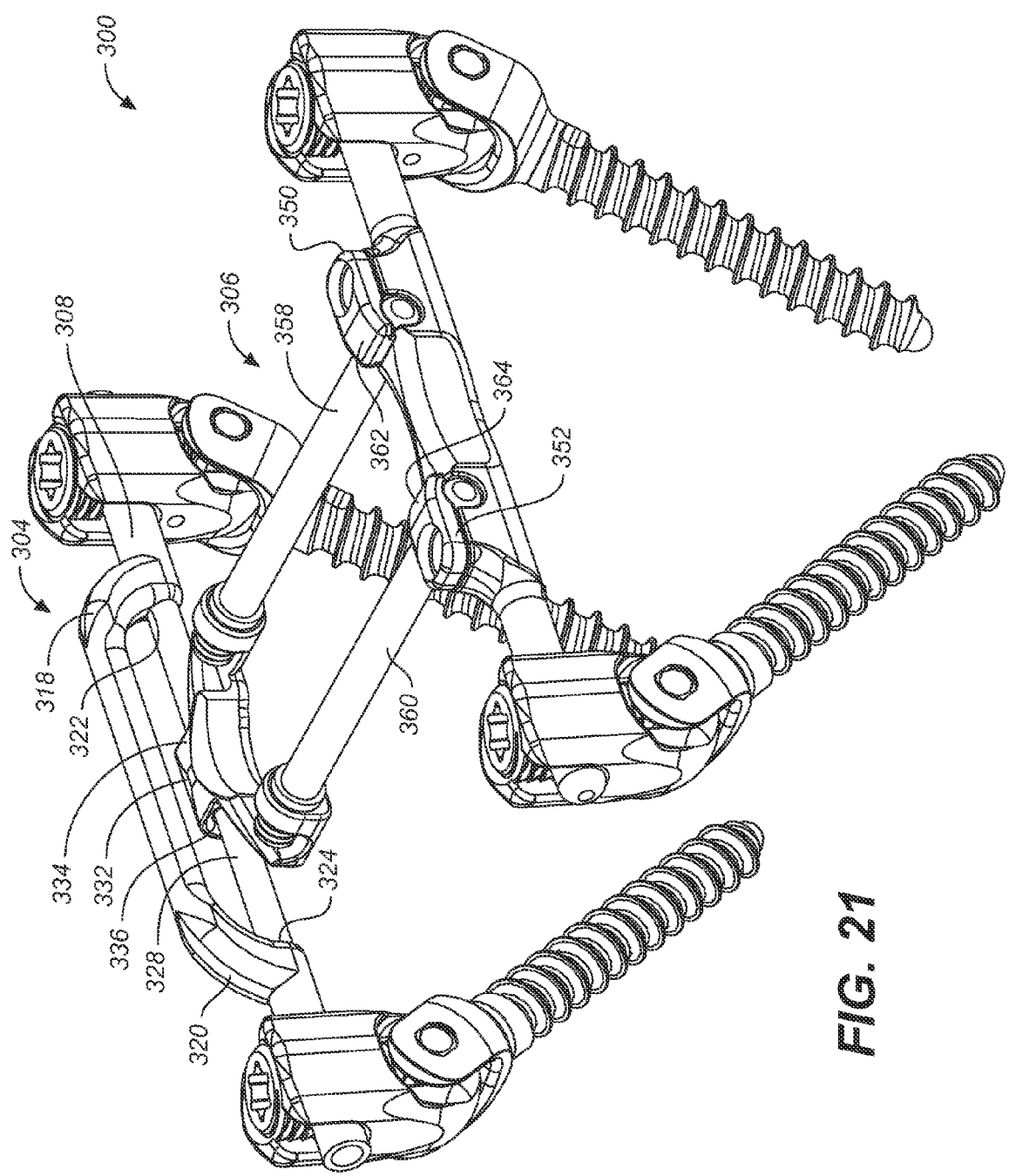
FIG. 21 is another perspective view of the embodiment of the dynamic spine stabilization of the invention of FIG. 19.
Figure 22A:
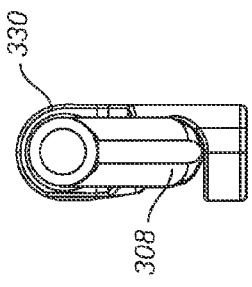
FIG. 22A is an end view of the embodiment depicted in FIG. 22.
Figure 22:
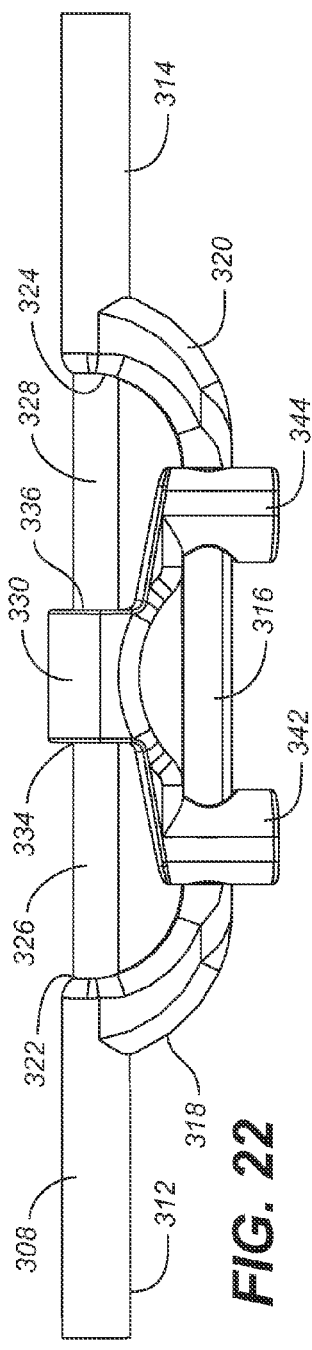
FIG. 22 is a side view the embodiment of the horizontal rod system of the invention as depicted in FIG. 19 configured in a closed position for implantation.
Figure 23:
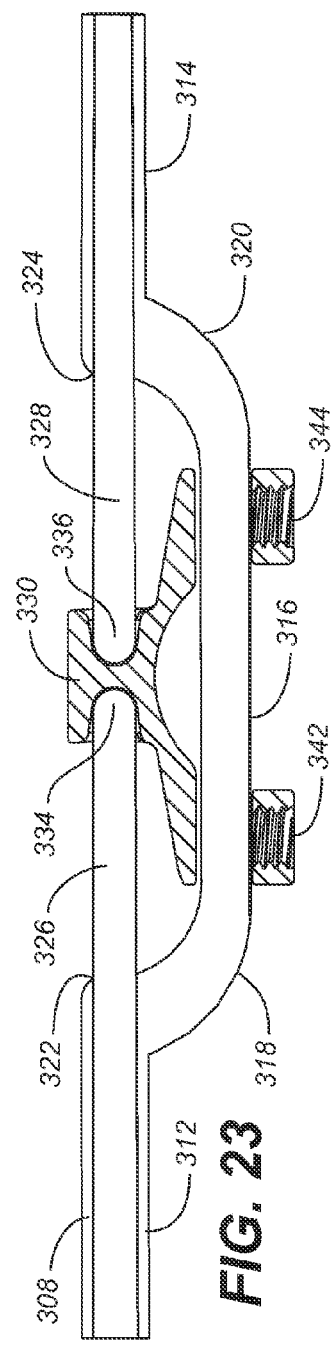
FIG. 23 is a side view partially in phantom form of the horizontal rod system of FIG. 22.
Figure 24:
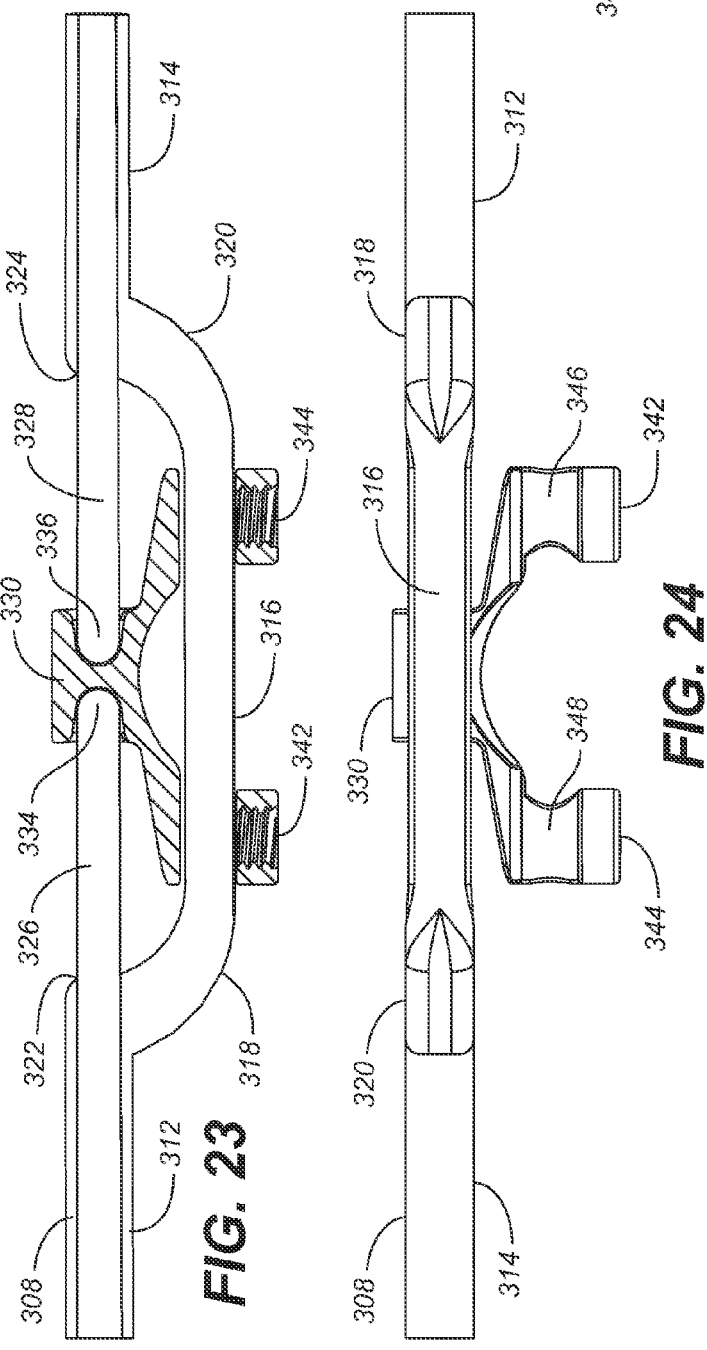
FIG. 24 is a side view of the embodiment of FIG. 22 in an open position as used when the embodiment is deployed in a spine.
Figure 25:
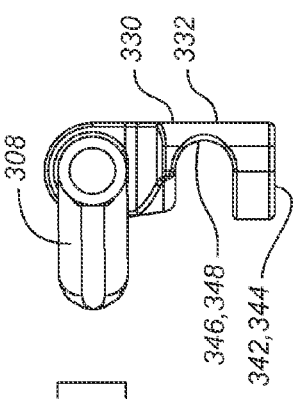
FIG. 25 is an end view of the embodiment depicted in FIG. 24.

With respect to FIG. 19 through FIG. 25 another embodiment of the horizontal rod system 304 of the dynamic stabilization system 300 is depicted as used with an anchor system 102 of the embodiment depicted in FIG. 1. Also shown in FIGS. 19, 19A, is the vertical rod system 306. The horizontal rod system 304 includes first and second horizontal rods 308, 310. It is to be understood that FIG. 19A shows a second image of only the horizontal rod 308 in a first undeployed position and that FIG. 19 shows a deployed position with the horizontal rod 308 connected with vertical rods 306 and, thus, the entire system 300.

The horizontal rod 308 includes first and second aligned end rods 312, 314 which are connected together with an offset rod 316 located between the first and second end rods 312, 314. In this embodiment, the horizontal rod 308 looks much like a yoke with the offset rod joining each of the end rods 312, 314 with a curved section 318, 320. At the junction of the first end rod 312 and the offset rod 316 is a first bore 322 which is aligned with the first end rod 312, and at the junction of the second end rod 314 and the offset rod 316 is a second bore 324 which is aligned with the second end rod 314 and, thus, aligned with the first end rod 312. Positioned in and extending from the first bore 322 is a first deflection rod or loading rod 326 and positioned in and extending from the second bore 324 is a second deflection rod or loading rod 328. As with the other deflection rods or loading rods, preferably deflection rods or loading rods 324, 328 are made of a super elastic material such as, for example, Nitinol (NiTi) and the rest of system 300 is comprised of titanium, stainless steel, a biocompatible polymer such as PEEK or other biocompatible material. In addition to Nitinol or nickel-titanium (NiTi), other super elastic materials include copper-zinc-aluminum and copper-aluminum-nickel. However, for biocompatibility the nickel-titanium is the desired material. The super elastic material has been selected for the deflection rods as the stress or force/deflection chart for a super elastic material has a plateau where the force is relatively constant as the deflection increases. Stated differently, a super elastic rod has a load (y) axis/deflection (x) axis curve which has a plateau at a certain level where the load plateaus or flattens out with increased deflection. In other words, the rod continues to deflect with the load staying constant at the plateau. In one embodiment, the load plateau is about 250 Newtons to about 300 Newtons. It is to be understood that the plateau can be customized to the needs of the patient by the selection of the type and composition of the super elastic material. For some patients, the plateau should be lower, and, for others, the plateau should be higher. Accordingly, and, for example, at the plateau, additional force is not put on the anchor system 102 and, thus, additional force is not put on the area of implantation of the bone screw 108 and the surrounding bone of the spine where the bone screw 108 is implanted. The deflection rods or loading rods 326, 328 are force fit, screwed, welded, or glued into the bores 322, 324 as desired.

The first and second deflection rods or loading rods 326, 328 extend from the respective bores 322, 324 toward each other and are joined by a Y-shaped connector 330. The Y-shaped connector 330 includes a base 332 which has opposed and aligned bores 334, 336 that can receive the deflection rods or loading rods 326, 328 in a manner that preferably allows the Y-shaped connector to pivot about the longitudinal axis defined by the aligned first and second deflection rods or loading rods 326, 328. The Y-shaped connector 330 includes first and second arms that preferably end in threaded bores 342, 344 that can receive the threaded ends of the vertical bar system 306 as described below. Just behind the threaded bores 342, 344 are recesses 346, 348 (FIG. 24) which are shaped to accept the offset rod 316 with the horizontal rod 308 in the undeployed configuration depicted in FIG. 19A. In the undeployed configuration, the horizontal rod 308 can be more easily implanted between the tissues and bones of the spine and, in particular, guided between the spinous processes. Once the first horizontal rod 308 is implanted, the Y-shaped connector 330 can be deployed by rotating it about 90 degrees or as required by the anatomy of the spine of the patient and connected with the vertical rod system 306.

The second horizontal rod 310 is similar to the second horizontal rod 116 of the embodiment of FIG. 1. This second horizontal rod 310 is preferably comprised of titanium or other biocompatible material and includes first and second mounts 350, 352 which can receive the ends of the vertical rod system 306. The mounts 350, 352 include respective recesses 354, 356 which can receive the vertical rods 358, 360 of the vertical rod system 306. The mounts 350, 352 also include tabs 362, 364 which can capture the vertical rods 358, 360 in the respective recesses 354, 356. The tabs 362, 364 can be secured to the mounts 350, 352 with screws or other appropriate fastening devices.

The first and second vertical rods 358, 360 are preferably comprised of titanium or other biocompatible material and include a threaded end and a non-threaded end. The threaded end can be formed on the end of the rod or threaded elements can be force fit or glued to the end of the vertical rods 358, 360. Once the first and second horizontal rods are deployed in the patient, the first and second vertical rods can be screwed into or otherwise captured by the Y-shaped connector 330 of the first horizontal bar 308 and the first and second vertical rods can be captured or otherwise secured to the second horizontal bar 310.

FIGS. 26, 27, and FIGS. 28, 29 depict yet more alternative embodiments of the horizontal rod systems of the invention. The horizontal rod 370 in FIG. 26, 27 is similar to the horizontal rod 118 in FIG. 1. Horizontal rod 370 includes a mount 372 which has bores that can receive first and second deflection rods or loading rods 374, 376 which are preferably made of a super elastic material. At the ends of the first and second deflection rods or loading rods 374, 376 are connectors which include a tab having a threaded bore therethrough. The connectors can be used to connect vertical rods to the deflection rods or loading rods.

FIGS. 28, 29 depict a horizontal rod 380 with first mount 382 and second mount 384. Each of the mounts 382, 884, includes a bore that is substantially parallel to the horizontal rod 380. First and second deflection rods or loading rods 386, 388 extend respectively from the bores of the first and second mounts 382, 382. In the embodiment depicted the deflection rods or loading rods 386, 388 are parallel to the horizontal rod 380 and are directed toward each other. Alternatively, the deflection rods or loading rods 386, 388 can be directed away from each other. In that configuration, the mounts 382, 384 would be spaced apart and the deflection rods or loading rods would be shorter as the deflection rods or loading rods extended parallel to and toward the ends of the horizontal rod 380.

Figures 30, 31:
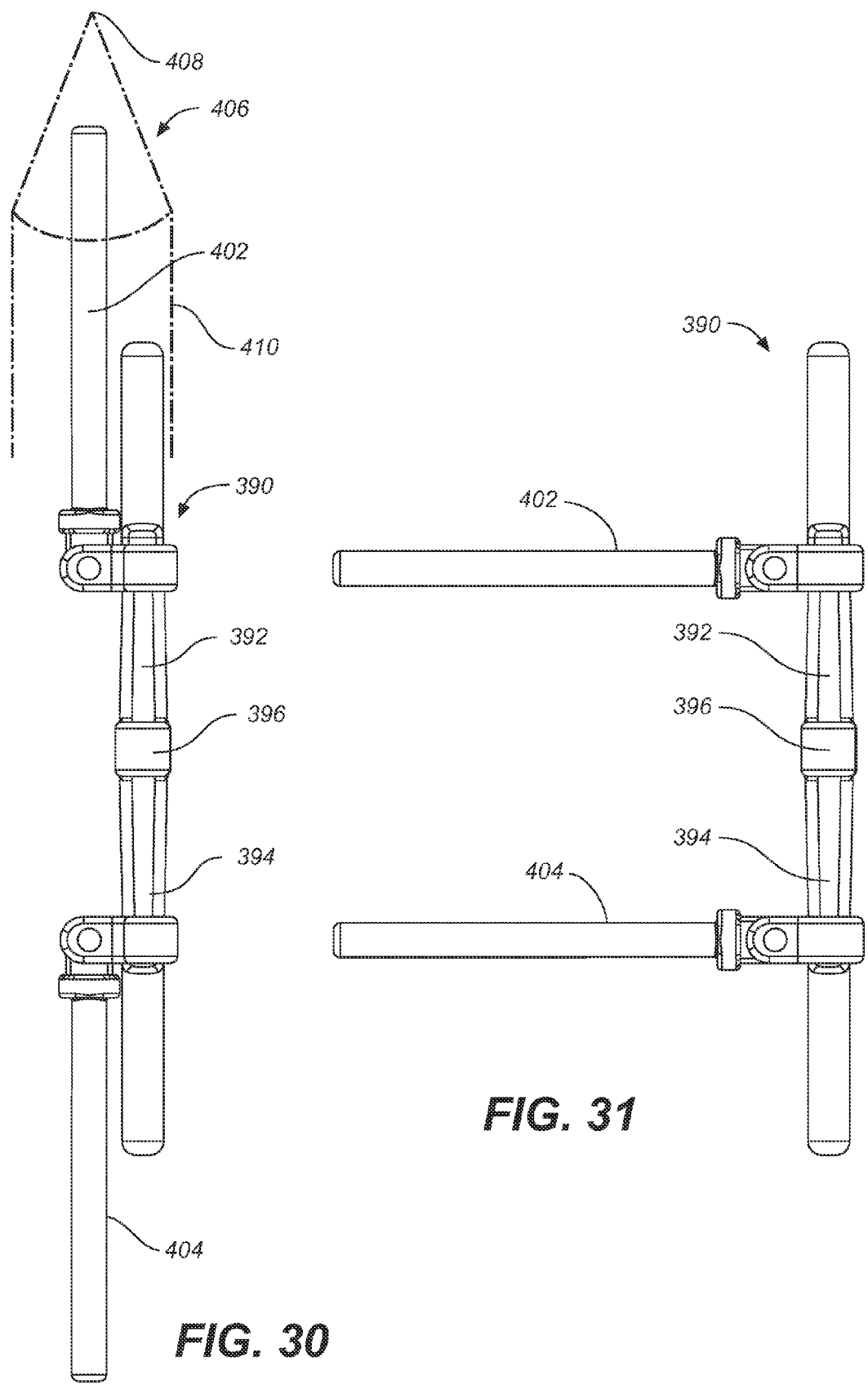
FIG. 30 is a top view of another embodiment of the horizontal rod system of the invention as depicted in FIG. 1 with the horizontal rod system in an undeployed position ready for implantation.
FIG. 31 is a top view of the embodiment of the horizontal rod system of FIG. 30 in a deployed position after implantation.
Figure 32:
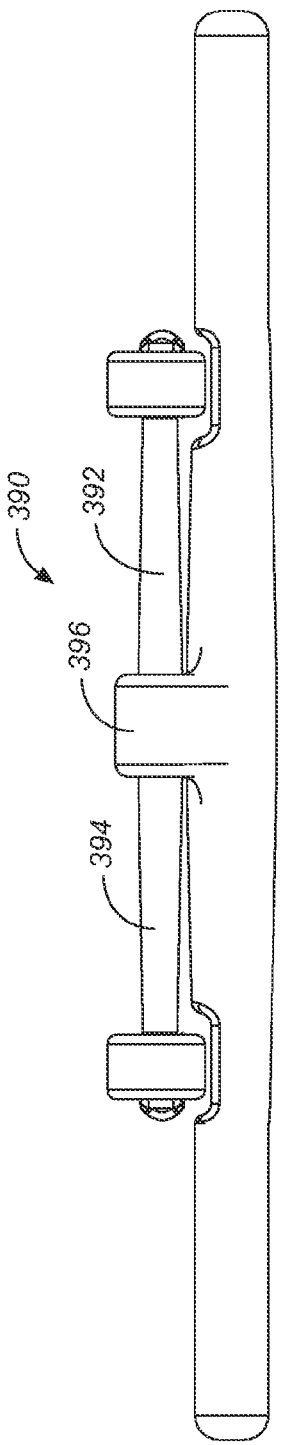
FIG. 32 is a side view, partially in phantom of the embodiment depicted in FIG. 30.

FIGS. 30, 31, 32 depict yet another embodiment of the horizontal rod system 390 of the invention which is similar to the horizontal bar system 104 as depicted in FIG. 1. Horizontal bar system 390 includes tapered deflection rods or loading rods 392, 394. The deflection rods or loading rods are tapered and reduce in diameter from the mount 396 toward the ends of the horizontal rod 390. As previously discussed the deflection rods or loading rods can taper continuously or in discrete steps and can also have an decreasing diameter from the ends of the deflection rods or loading rods towards the mount 396. In other words, a reverse taper than what is depicted in FIG. 30. Connected to the deflection rod or loading rods 392, 394 are the vertical rods 402, 404. The vertical rods 402, 404 are connected to the deflection rods or loading rods 392, 394 as explained above.

The conically shaped or tapered deflection rods or loading rods can be formed by drawing or grinding the material which is preferably a super elastic material. The tapered shape of the deflection rods or loading rods distributes the load or forces placed by the spine on the system evenly over the relatively short length of the deflection rods or loading rods as the rods extend from the central mount outwardly toward the ends of the horizontal rod. In this embodiment, in order to be operatively positioned relative to the spine and between the anchor systems, the deflection rods or loading rods are less than half the length of the horizontal rods.

FIG. 30 depicts the vertical rods 402, 404 in undeployed positions that are about parallel to the horizontal rod 390 and with the vertical rods 402, 404 directed away from each other and toward the respective ends of the horizontal rod 390. In this position the horizontal rod 390 can be more conveniently directed through the bone and tissue of the spine and, for example, directed between the spinous processes to the implant position. Once in position, the vertical rods 402, 404 can be deployed so that the vertical rods are parallel to each other and about parallel to the horizontal rod 390 as depicted in FIG. 31. Accordingly, this embodiment can be inserted from the side of the spine in the undeployed configuration depicted in FIG. 30 and then the vertical rods can be rotated or deployed by about 90 degrees (from FIG. 30 to FIG. 31) each into the coronal plane of the patient. The vertical rods are also free to rotate about 180 degrees about the deflection rods and in the sagittal plane of patient. This allows this embodiment to conform to the different sagittal contours that may be encountered relative to the spine of a patient. The deflection rods or loading rods are rigidly connected to the horizontal rod allowing for an easier surgical technique as sections of the spine and, in particular, the spinous processes and associated ligaments and tissues do not have to be removed in order to accommodate the implantation system 100. The moving action of the system, and, in particular, the flexing of the deflection rods and the motion of the vertical rods connected to the deflection rods or loading rods, takes place about the spinous processes and associated tissues and ligaments, and, thus, the spinous processes do not interfere with this motion. Further, having the horizontal rods more lateral than central also allows for a more simple surgical technique through, for example, a Wiltse approach.

To assist in implantation, a cone 406 can be slipped over the end of the horizontal rod 390 and the vertical rod 402 to assist in urging the tissues and bone associated with the spine out of the way. Once the horizontal rod is implanted the cone 406 can be removed. The cone 406 includes an end 408 which can be pointed or bulbous and the cone 406 has an increasing diameter in the direction to the sleeve 410 portion of the cone 406. The sleeve can be cylindrical and receive the end of the horizontal rod and the end of the deflection rod or loading rod 402.

FIG. 32 depicts how the connectors 412, 414 are secured to the respective deflection rods 392, 394. The deflection rods have flanges, such as spaced apart flange 416, 418 on the deflection rod 392. The connectors 412, 414 can snap over and be retained between respective pairs of flanges.

Figure 33:
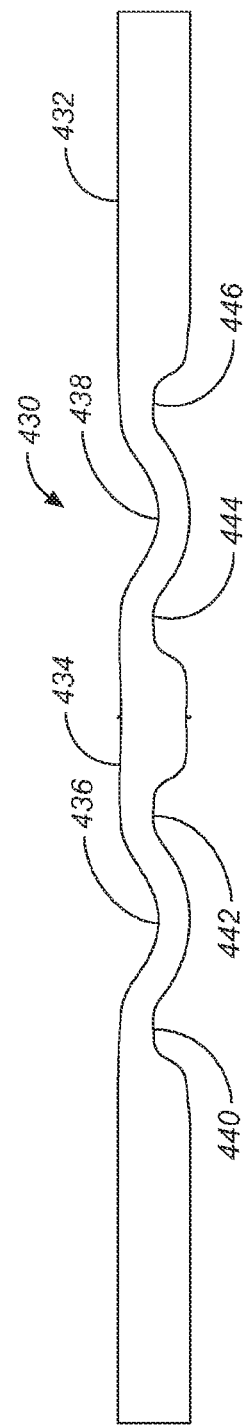
FIG. 33 is a side view of an alternative embodiment of the horizontal rod system of the invention.

FIG. 33 depicts yet another embodiment of the horizontal rod system 430 of the invention. The horizontal rod system 430 includes horizontal rod 432 which is preferably comprised of a super elastic material such as Nitinol. The horizontal rod 432 includes a generally central platform 434, and on each side of the central platform 434 are first and second upwardly facing scallops or recesses 436, 438. On each side of the upwardly facing scallop or recess 436 are downwardly facing scallops or recesses 440, 442. On each side of the upwardly facing scallop or recess 438 are downwardly facing scallops or recesses 444, 446. The platform 434 accepts a connector for connecting the horizontal rod to vertical rods (FIG. 40) as will be explained below, and the scallops 436, 440, 442 on one side of the platform 434 act as a spring and the scallop 438, 444, 446 on the other side of the platform 434 acts as a spring. These springs assist the platform in carrying the load that the spine can place on the horizontal rod and isolate the anchor systems 102 from that load. That isolation has the advantage of preventing loosening of the anchor system as implanted in the patient. It is to be understood that by varying the pattern of the scallops, that the stiffness or rigidity of the horizontal bar can be varied and customized for each patient. Fewer scallops will generally result in a more stiff horizontal bar and more scallops will generally result in a less rigid horizontal bar. Additionally, the stiffness can be different depending on the direction of the force that is placed on the horizontal bar depending on the orientation and location of the scallops. For the embodiment depicted in FIG. 33, with the scallops 436, 438 pointed upward to the head of a patient and the scallops 440, 442, 444, 446 pointed downward toward the feet of a patient, the horizontal bar is stiffer in extension and less stiff in flexion. It is noted that in this embodiment the rod is of a uniform diameter, although the diameter can be non-uniform as, for example, being larger where the platform 434 is and tapering to the ends of the horizontal rod 432, or having a large diameter at the ends of the horizontal rod 432, tapering to a smaller diameter at the platform 434. In this embodiment with a substantially uniform diameter, the scallops are formed within the uniform diameter. In other forms, the scallops are molded into the horizontal rod or machined out of the preformed horizontal rod. With this configuration, the horizontal rod is more easily inserted into the spine and between bones and tissues of the spine. Further, this horizontal rod can be more easily delivered to the spine through a cannula due to the substantially uniform diameter. For purposes of forming the scallops a machining technique known as wire electric discharge machining or wire EDM can be used. Thus, an approach for shaping the super elastic material is through wire EDM followed by electro-polishing. Additionally, the super elastic material in this and the other embodiments can be cold rolled, drawn or worked in order to increase the super elastic property of the material.

In this embodiment, the deflection takes place almost exclusively in the middle portion of the horizontal rod and principally at the platform and spring thus relieving the load or force on the ends of the horizontal rod and on the anchor system/bone interface.

Accordingly, in this preferred embodiment, there are two superior scallops pointing upwardly having a relatively gentler radius compared to the tighter radii of the inferior scallops pointing downwardly. It is to be understood that in this preferred embodiment, the inferior scallops are not symmetrical the way the superior scallops are. The lateral most cuts in both of the most lateral inferior scallops are steep and not radiused. These cuts allow the rod to bend at these points enhancing the spring effect. The ratio of the radii of the superior scallop to the inferior scallop in this preferred embodiment is two to one. The result is to create two curved and flat (in cross-section) sections, one on each side of the platform and these two flat sections in this preferred embodiment have about the same uniform thickness. Again, in this embodiment, the scallops and the platform is formed into an otherwise uniformly diametered cylindrical rod. Accordingly, none of these formed elements in this preferred embodiment extend beyond the diameter of the rod. In this preferred embodiment, the diameter of the horizontal rod is about 4 mm.

If desired, the rod could be bent in such a way that the platform and/or the scallops extend outside of the diameter of the cylindrical rod. However that configuration would not be as suitable for implantation through a cannula or percutaneously as would the horizontal rod as shown in FIG. 33 and described above.

Figure 47:
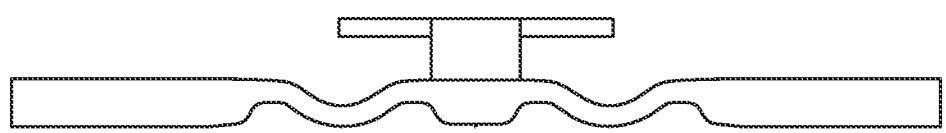
FIG. 47 is yet another embodiment of the horizontal rod system of the invention.

It is to be understood that to have enhanced flexibility, that the torsion rod and connector elements used in the horizontal rod embodiment of FIG. 1 can be used with the horizontal rod of FIG. 33. In this embodiment (FIG. 47), the connector is secured to the platform of the horizontal rod of FIG. 33 with the two deflection rods or loading rods extending toward the ends of the horizontal rod of FIG. 33 and about parallel to that horizontal rod.

Figure 33A:
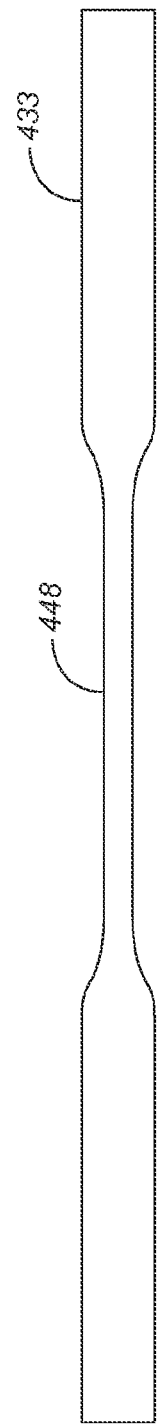
FIG. 33A is a side view of yet another embodiment of the horizontal rod system of the invention.

Another embodiment of the horizontal rod 433 is depicted in FIG. 33A. In this embodiment the horizontal rod 433 is similar to the horizontal rod in FIG. 33 with the exception that the platform and scallops are replaced with a reduced diameter central potion 448. Each end of the central portion 448 gradually increases in diameter until the diameter is the full diameter of the ends of the horizontal rod 433. This embodiment can be formed of a super elastic material and ground to the reduced diameter shape from a rod stock of the super elastic material. The rod stock could also be drawn to this shape. Generally after such operations the horizontal rod would be electro polished. In this embodiment, a connector such as the connector shown in FIG. 40 could be used to connect vertical rods to preferably the middle of the central portion 448.

Figure 34C:
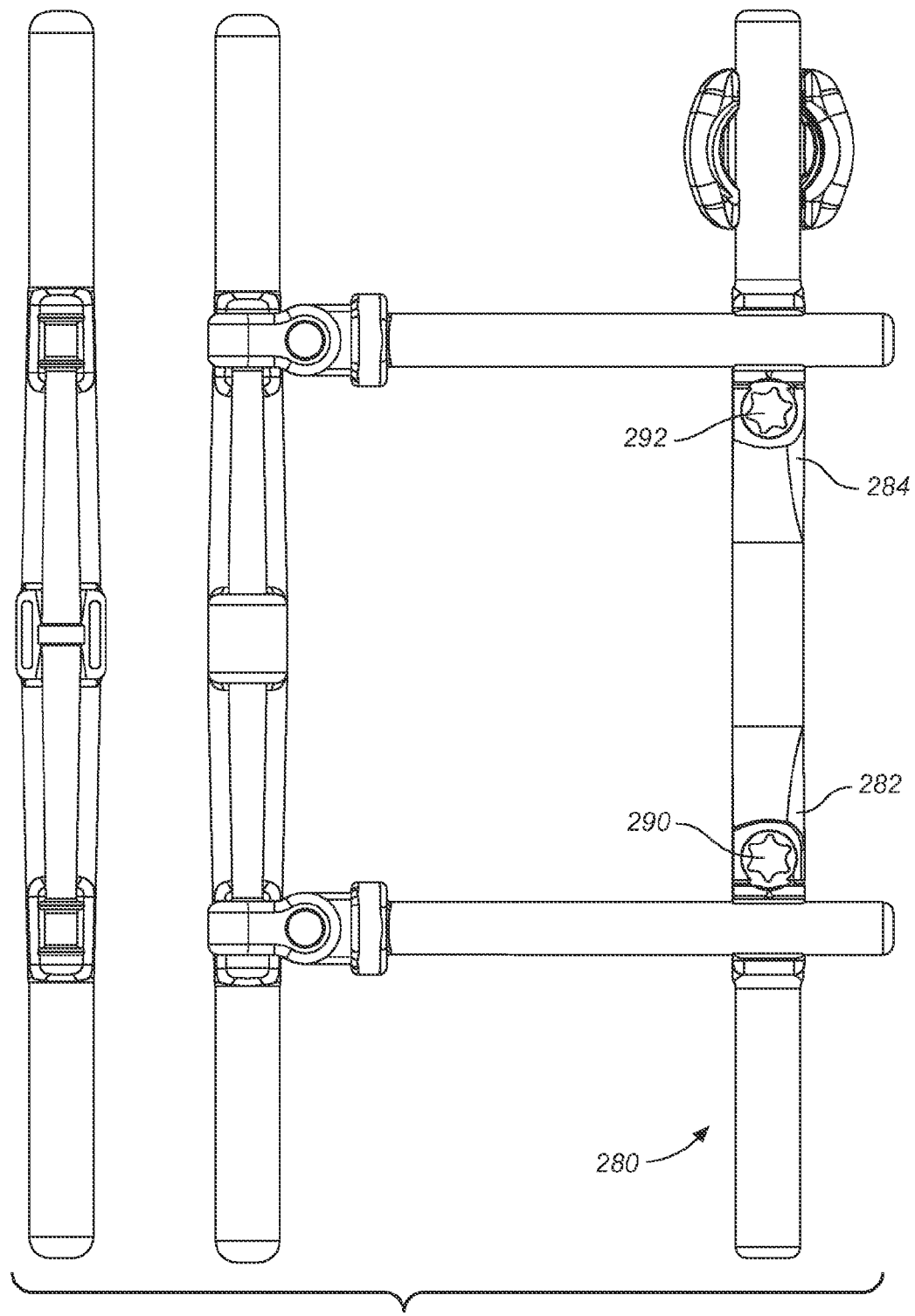
FIG. 34C is a top view of the embodiment of FIG. 34A.

FIGS. 34A, 34B, 34C depict yet an alternative embodiment of a horizontal rod 280 such as horizontal rod 116 as shown in FIG. 1 that is meant to rigidly hold the vertical rods secured thereto. The mounts 282, 284 formed in this horizontal rod 280 include a body that can be formed with the rod 280. The mounts are then provided with a movable capture arm 286, 288 that have recesses, which capture arms are formed out of the mount preferably using a wire EDM process that leaves the capture arm still connected to the horizontal rod with a living hinge. Eccentric headed set screws 290, 292 are mounted on the horizontal bar. With vertical rods captured in the recesses of the capture arms, the eccentric set screws can be turned to urge the capture arms against the living hinge, and thereby capturing the vertical rods in the recesses of the capture arms.

Figure 40:
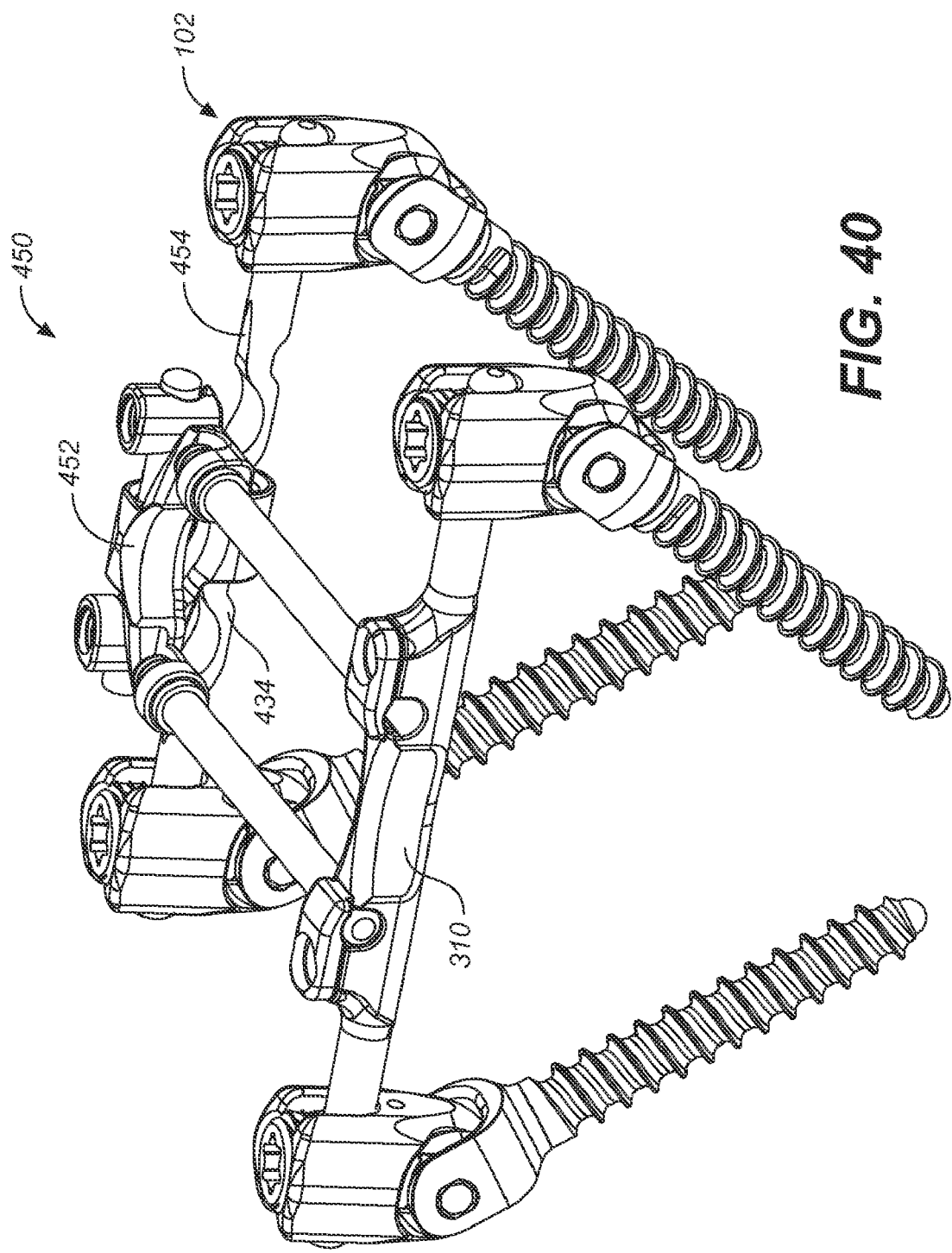
FIG. 40 is a perspective view of another embodiment of a dynamic spine stabilization system of the invention.

FIG. 40 depicts a dynamic stabilization system 450 that uses the horizontal rod system 454 of the invention. The system 450 additionally uses the anchor system 102 as depicted in FIG. 1 and the other horizontal rod 310 as depicted in FIGS. 19, 34. A connector 452 is secured to the platform 434 of the horizontal rod 454 and vertical rods are connected to the connector and to the other horizontal rod 310. In FIG. 40 for the horizontal rod 454, the scallops are formed by bending a bar and not by forming the scallops in a straight horizontal bar as depicted in the horizontal bar 432 of FIG. 33. The horizontal rod 430 of FIG. 33 could also be used in the embodiment of FIG. 40.

Figure 35:
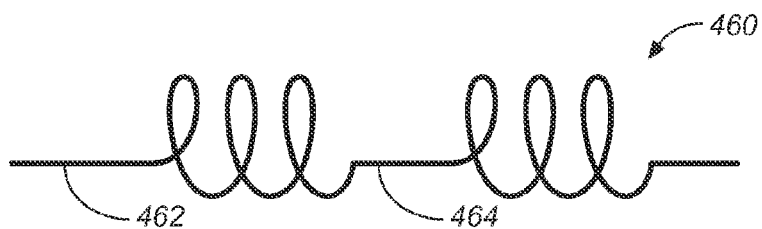
FIG. 35 is a side view of still another alternative embodiment of the horizontal rod system of the invention.

FIG. 35 depicts an alternative embodiment of a horizontal rod system 460 of the invention. Horizontal rod system 460 includes a horizontal rod 462 with a central platform 464 and first and second spring regions 466, 468 located on either side of the platform 464. Extending outwardly from each spring region are respective ends of the horizontal rod 462. The spring regions include coils that are wound about the longitudinal axis of the horizontal rod 462. If desired, the entire horizontal rod 462 can be comprised of a rod wound around a longitudinal axis with the platform 464 and the ends of the horizontal rod being more tightly wound and/or with a smaller diameter and the spring regions 466, 468 more loosely wound and/or with a larger diameter. Such a horizontal rod 462 can preferably be comprised of super elastic material such as Nitinol or alternatively titanium or other biocompatible material which demonstrates the ability to flex repeatedly.

Figure 36:
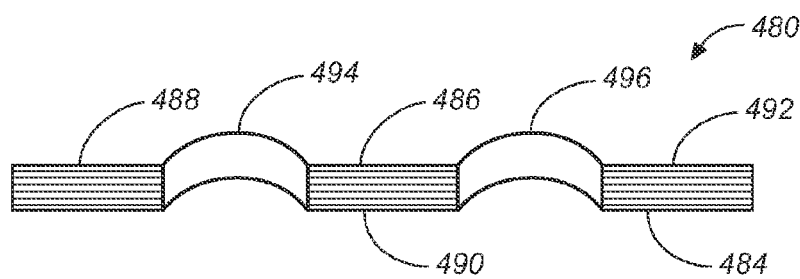
FIG. 36 is a side view of yet another alternative embodiment of the horizontal rod system of the invention.

FIG. 36 depicts yet another alternative embodiment of a horizontal rod system 480 which includes first and second horizontal rods 482, 484 which can be flat rods if desired. The horizontal rods 482, 484, include spring region 494, 496. In the spring region the horizontal rod is formed into an arc, much like a leaf spring. Located at the ends and at the central platform 486 and between the horizontal rods 482, 484 are spacers 488, 490, 492. The spacers are glued, bonded, welded or otherwise secured between the first and second horizontal rods 482, 484 in order to form the horizontal rod system 480. This system 480 can be comprised of super elastic materials or other materials that are biocompatible with the patient.

Figure 37:
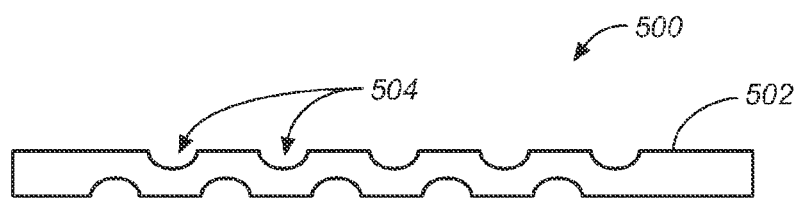
FIG. 37 is a side view of another alternative embodiment of the horizontal rod system of the invention.

FIG. 37 depicts another embodiment of the horizontal rod system 500 including a horizontal rod 502. In this embodiment, recesses 504 are formed in the horizontal rod in order to define the stiffness of the horizontal rod 502. This system can be formed of a super elastic material or other biocompatible material.

Figure 38:
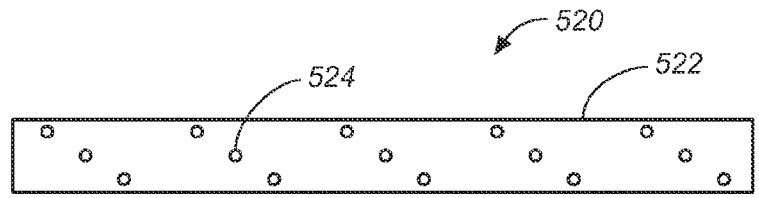
FIG. 38 is a side view of another alternative embodiment of the horizontal rod system of the invention.

FIG. 38 depicts still another embodiment of the horizontal rod system 520 of the invention with a horizontal rod 522. The horizontal rod 522 includes dimples 524 distributed around and along the horizontal rod 522. As this other embodiment, depending on the distribution of the dimples, the stiffness of the horizontal rod 522 can be determined. Further is more dimples are placed on the lower surface than on the upper surface, when placed in a patient, the horizontal rod 522 would tend to be stiffer in extension and less stiff in flexion. This horizontal rod 522 can also be made of a super elastic material or other biocompatible material.

Figure 39:
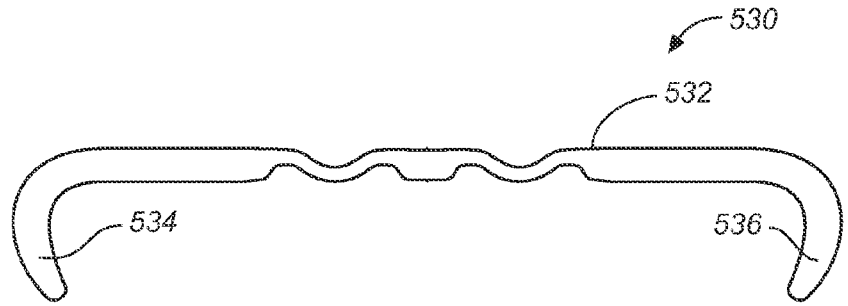
FIG. 39 is a side view of yet another alternative embodiment of the horizontal rod system of the invention.

FIG. 39 depicts another embodiment of the horizontal rod system 530 of the invention which has a horizontal rod 532 which is similar to the horizontal rod 432 of FIG. 33 and, thus, similar elements will number with similar numbers. In addition, the ends 534, 536 of the horizontal rod 532 are curved so as to create hooks that can fit around portions of the vertebra so as to secure the horizontal rod 532 to the vertebra. In this embodiment, preferably the rod is comprised of super elastic material or other biocompatible material. In order to implant the rod, the hooks at ends 534, 536 are sprung open and allowed to spring closed around the vertebra. An anchor system which includes a hook (as discussed above) could be used with this system.

Figure 39A:
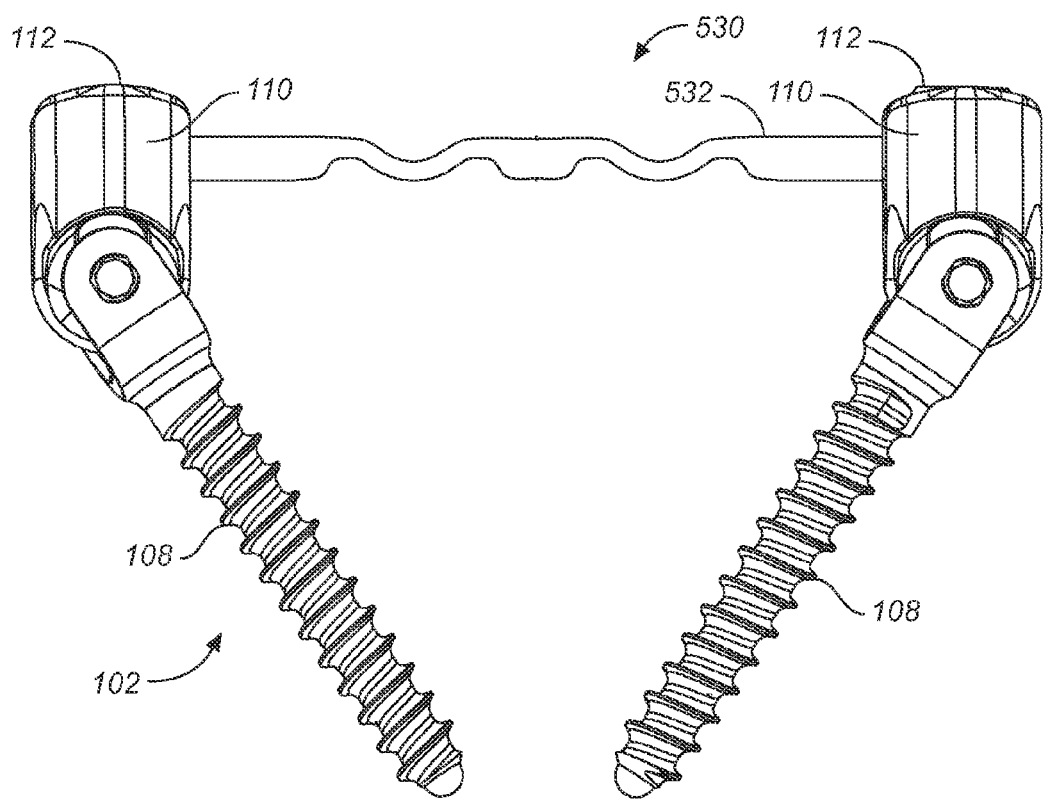
FIG. 39A is still another embodiment of the horizontal rod system and the anchor system of the invention.
Figure 39B:
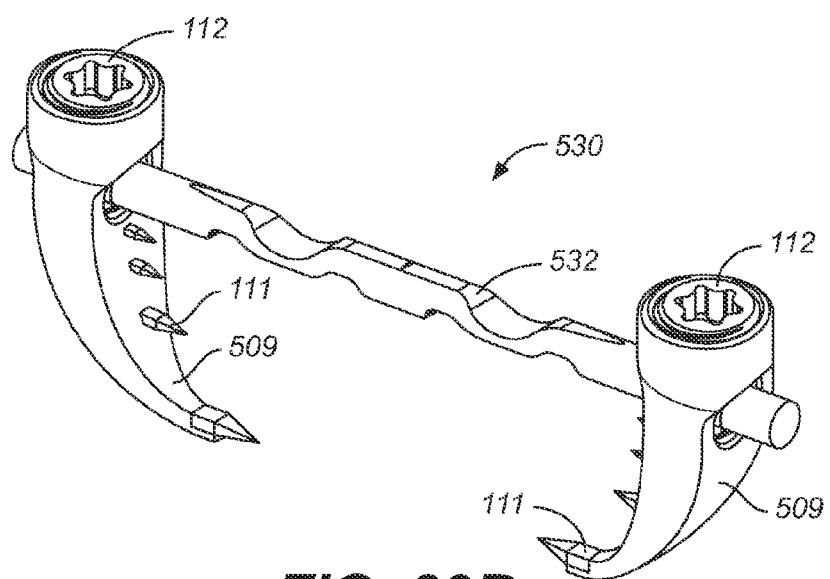
FIG. 39B is yet another embodiment of the horizontal rod system and the anchor system of the invention.

FIGS. 39A, 39B are similar to FIG. 39. In FIGS. 39A, 39B, a horizontal rod 532 is held in place relative to the spine by two anchor systems 102. The anchor systems are similar to the anchor systems depicted in FIG. 1. The anchor systems 102 include an anchor or bone screw 108 or bone hook 109 with spikes 111 (FIG. 39B), as well as the head 110 into which the horizontal rod is received. A set screw 112 secures the horizontal rod relative to the anchor systems.

Figure 41:
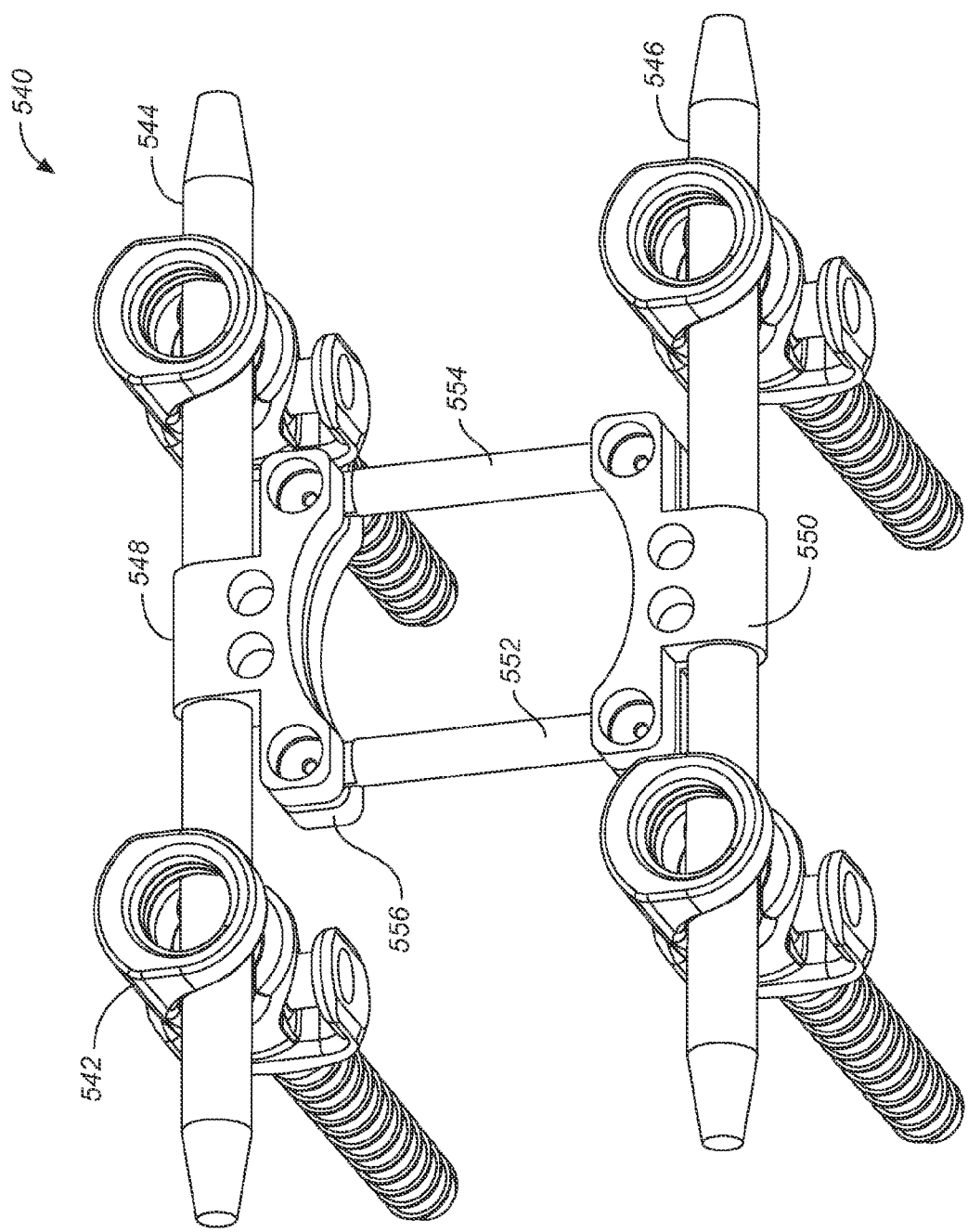
FIG. 41 is a perspective view of still another embodiment of a dynamic spine stabilization system of the invention.

FIG. 41 depicts another embodiment of the dynamic stabilization system 540 of the invention. This embodiment includes side loading anchor systems 542 as described above, although top loading anchor systems would also be appropriate for this embodiment. In this embodiment the horizontal rods 544, 546 are preferably comprised of a polymer such as PEEK and mounted on the horizontal rods 544, 546 are first and second connectors 548, 550. Vertical rods 552 and 554 are connected to the first and second connectors 548, 550 at points 556 with screws, rivets or other devices so that the connection is rigid or, alternatively, so that the vertical rods 552, 554 can pivot or rotate about the points. As the horizontal rods are comprised of PEEK, the system tends to be more rigid than if the rods were comprised of a super elastic material. Rigidity also depends on the diameter of the rod.

Embodiments of the Vertical Rod System of the Invention

Embodiments of vertical rod systems of the invention such as vertical rod system 106 are presented throughout this description of the invention. Generally, the vertical rod systems are comprised of vertical rods that can be pivoted or inserted into position after the horizontal rods are deployed in the patient. The vertical rods are preferably connected to the horizontal rods and not to the anchor systems in order to reduce the forces and stress on the anchor systems. The vertical rods are connected to the horizontal rod systems, which horizontal rod systems include mechanisms as described herein that reduce the forces and stresses on the anchor systems. The vertical rods can generally be comprised of titanium, stainless steel, PEEK or other biocompatible material. Should more flexibility be desired, the vertical rods can be comprised of a super elastic material.

Figure 42:
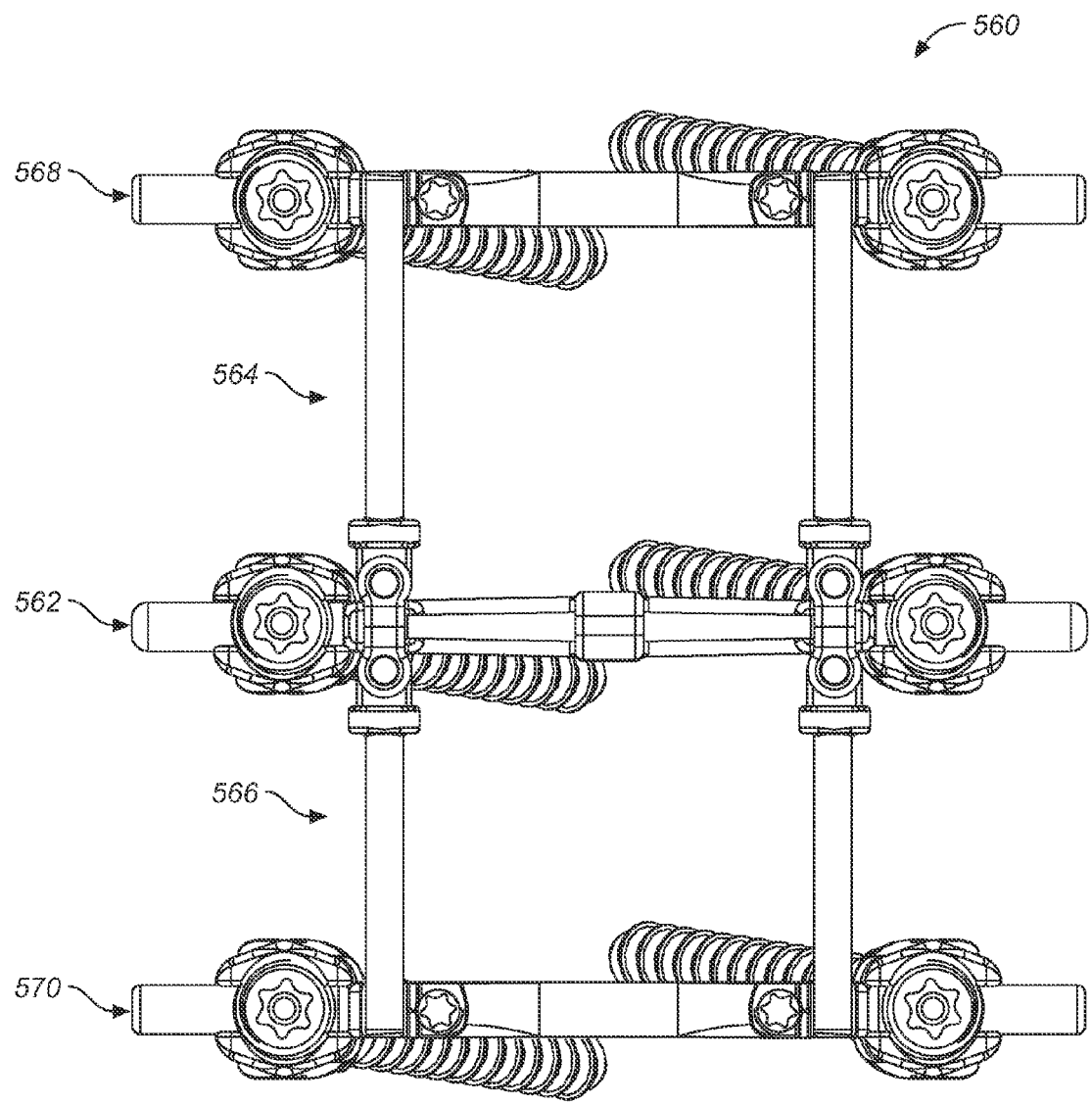
FIG. 42 is a side view of an embodiment of a two level dynamic spine stabilization system of the invention.

Embodiments of Alternative Multi-Level Dynamic Stabilization Systems for the Spine FIGS. 42 and 43 depict multi-level dynamic stabilization systems 560, 580. Each of these systems 560, 580 are two level systems. All of these systems use anchor systems as described herein. In system 560 of FIG. 42 the middle level horizontal rod 562 is secured to a vertebra and includes a horizontal rod system 104 having first and second deflection rods or loading rods such as that depicted in FIG. 4, whereby a first pair of vertical rods 564 can extend upwardly from horizontal rod system and a second pair of vertical rods 566 can extend downwardly from the horizontal rod system. The vertical rods that extend upwardly are connected to an upper horizontal rod 568 such as depicted in FIG. 34 and the vertical rods that extend downward are connected to a lower horizontal rod 568 such as depicted in FIG. 34. The upper horizontal rod 568 is secured with anchor systems to a vertebra located above the vertebra to which the middle level horizontal rod 562 is secured. The lower horizontal rod 570 is secured with anchor systems to a vertebra located below the vertebra to which the middle level horizontal rod 562 is secured. This embodiment offers more stability for the middle level vertebra relative to the upper and lower vertebra while allowing for extension, flexion, rotation and bending relative to the middle level vertebra.

FIG. 43 depicts another multi-level dynamic stabilization system 580. All of these systems use anchor systems as described herein. In system 580 of FIG. 43, the middle level horizontal rod 582 is secured to a vertebra and includes a horizontal rod such as that depicted in FIG. 34. The upper and lower horizontal rods 586, 590 can be similar to the horizontal rod 114 including the deflection rods or loading rods and deflection rod or loading rod mount depicted in FIG. 3. Vertical rods are pivotally and rotationally mounted to the upper and lower horizontal rods 586, 590 and, respectively, to the deflection or loading rods thereof and are also rigidly mounted to the middle level horizontal rod 582. The upper horizontal rod 586 is secured with anchor systems to a vertebra located above the vertebra to which the middle level horizontal rod 582 is secured. The lower horizontal rod 590 is secured with anchor systems to a vertebra located below the vertebra to which the middle level horizontal rod 582 is secured. This embodiment offers more dynamic stability for the upper and lower vertebra relative to the middle level vertebra while allowing for extension, flexion, rotation and bending relative to the middle level vertebra. Alternatively, the middle level horizontal rod 582 has four mounts instead of the two mounts depicted in FIG. 34 or FIG. 34A so that a first pair of vertical rods 588 can extend upwardly from a lower horizontal rod 590 and a second pair of vertical rods 566 extending downwardly from the upper horizontal rod 586, can be secured to the middle level horizontal rod 582.

Embodiments of Spine Fusion Systems of the Invention

Figure 44:
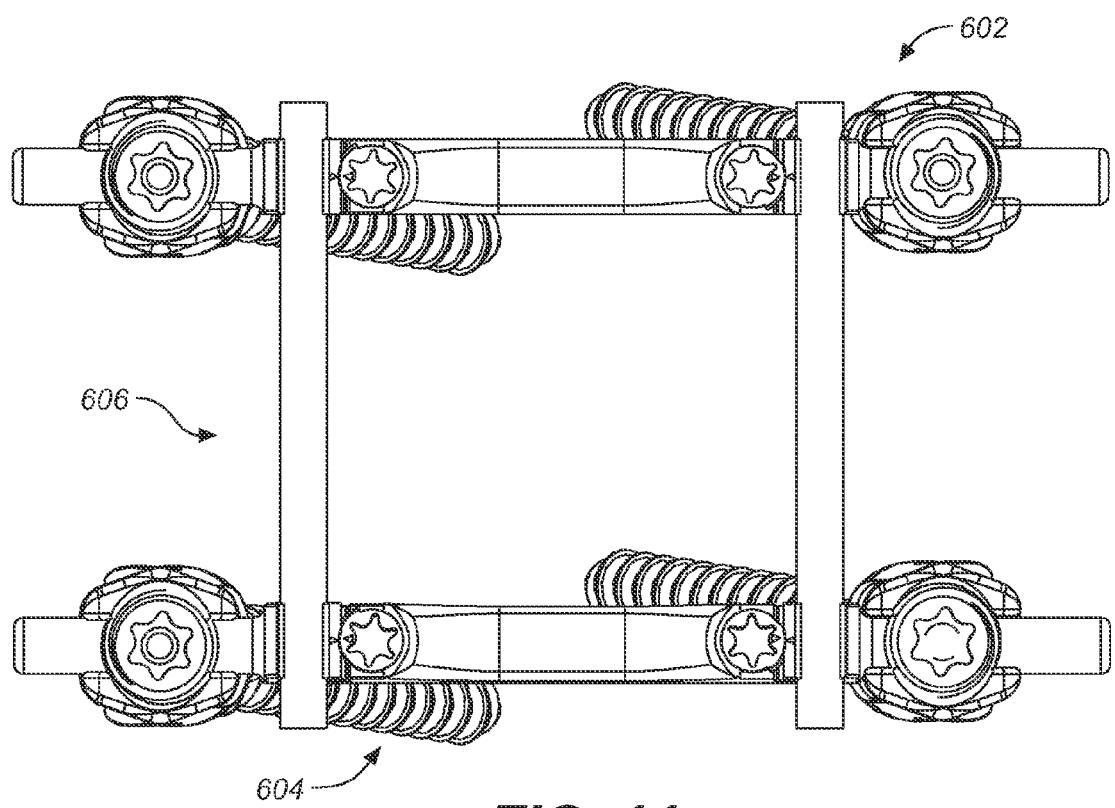
FIG. 44 is a side view of an embodiment of a fusion system of the invention.
Figure 45:
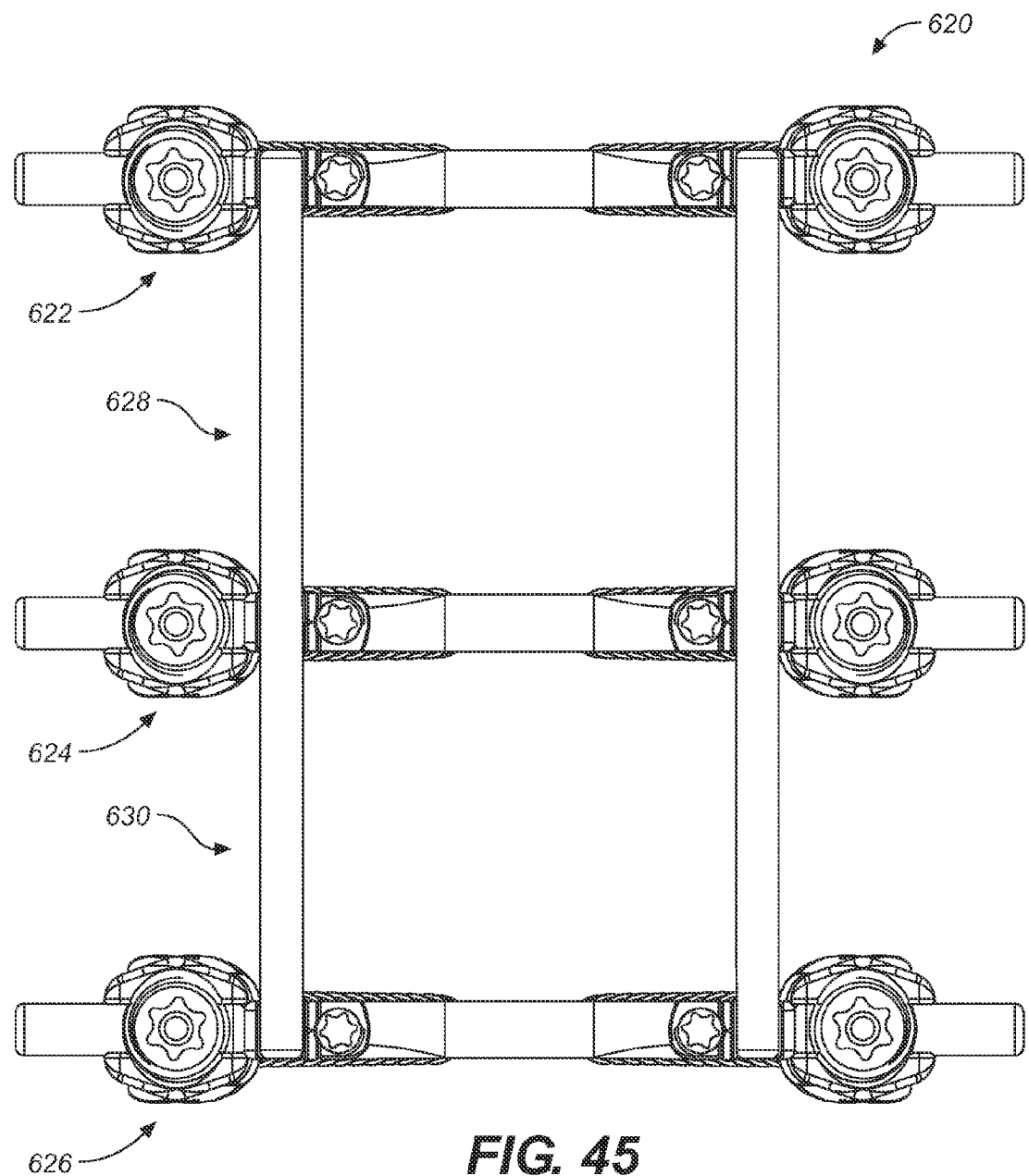
FIG. 45 is a side view of an embodiment of a two level fusion system of the invention.

FIGS. 44, 45 depict one and two level systems that are more preferably used for fusion. The system 600 depicted in FIG. 44 resembles the system depicted in FIG. 41. When PEEK is used for the horizontal rods 602, 604, the system is substantially rigid and can be used in conjunction with spine fusion. For example, this system can be used with the placement of bone or a fusion cage between vertebra to which this system is attached. In fusion, bone can be placed between the vertebral bodies or, alternatively, fusion can be accomplished by placing bone in the valleys on each side of the spinous processes. The horizontal rods 602, 604 an also be comprised of titanium, or other biocompatible material and be used for spine fusion. For this embodiment, the vertical rods 606 can be rigidly attached to the horizontal rods through the use of a horizontal rod with mounts, as depicted in FIG. 34, so that the vertical rods 606 do not move or pivot with respect to the horizontal rods.

FIG. 45 depicts a two level system 620 that is more preferably used for a two level fusion. Each level can use an anchor system for example described with respect to anchor system 102 of FIG. 1. The horizontal rods 622, 624, 626 are can be similar to the horizontal rod in FIG. 34 with either two vertical rod mounts for the upper and lower horizontal rods 622, 626 or four vertical rod mounts for the middle level horizontal rod 624. For this embodiment, the vertical rods 628, 630 can be rigidly attached to the horizontal rods through the use of a horizontal rod with mounts as depicted in FIG. 34 so that the vertical rods 628, 630 do not move or pivot with respect to the horizontal rods. Vertical rods 628 extend between the upper and middle horizontal rods 622, 624, and vertical rods 630 extend between the middle and lower horizontal rods 624, 626. The system 620 depicted in FIG. 44 resembles the system depicted in FIG. 41, but with respect to three levels. When PEEK is used for the horizontal rods 622, 624, 626, the system is substantially rigid and can be used in conjunction with spine fusion. For example, this system can be used with the placement of bone or a fusion cage between vertebra to which this system is attached. Bone can also be placed along the valleys on either side of the spinous processes for this system. The horizontal rods 622, 624, 626 can also be comprised of titanium, PEEK or other biocompatible material and be used for spine fusion.

Figure 45A:
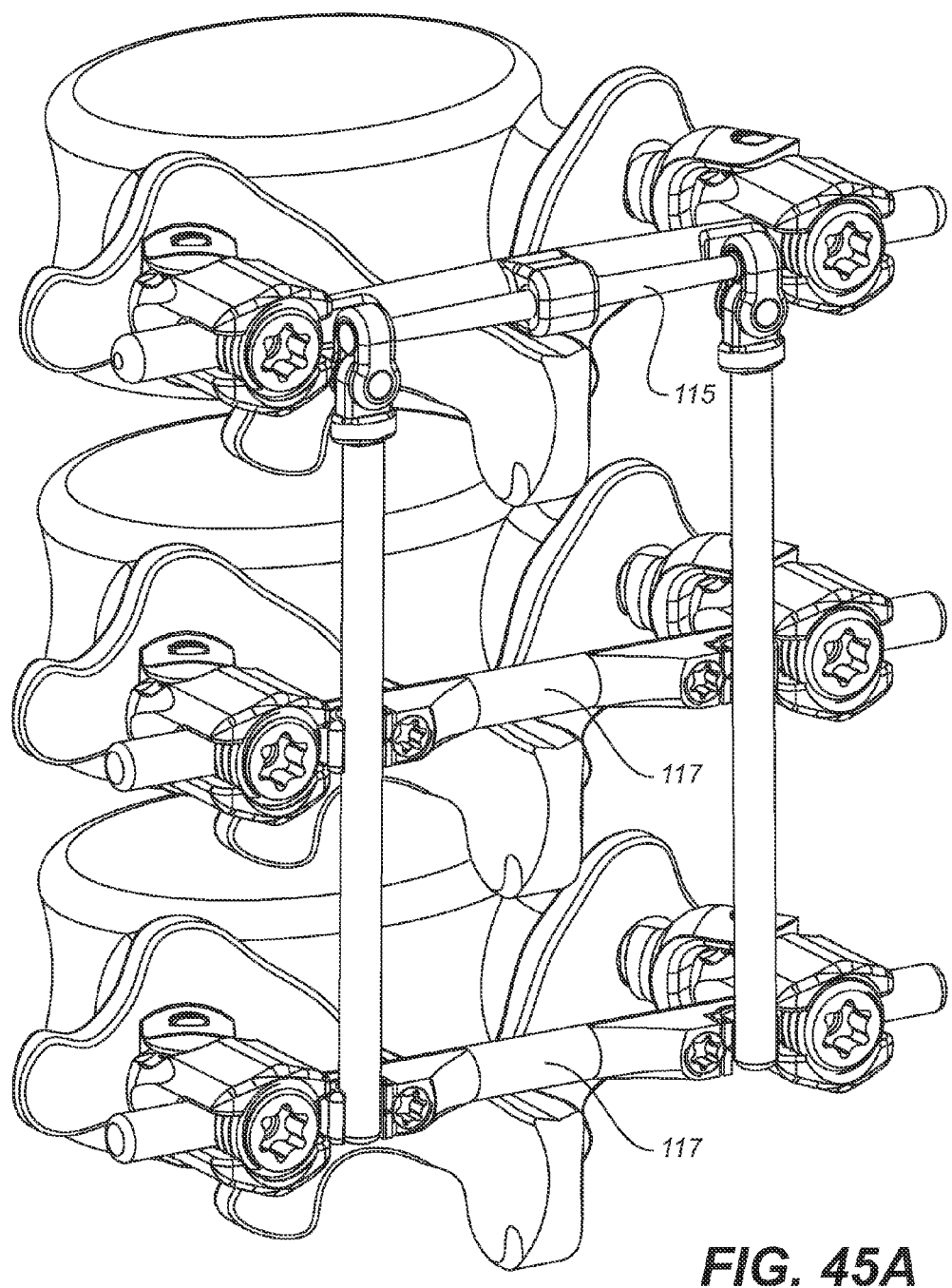
FIGS. 45A, 45B are perspective and side views of still another fusion system of an embodiment of the invention that has a transition level.
Figure 45B:
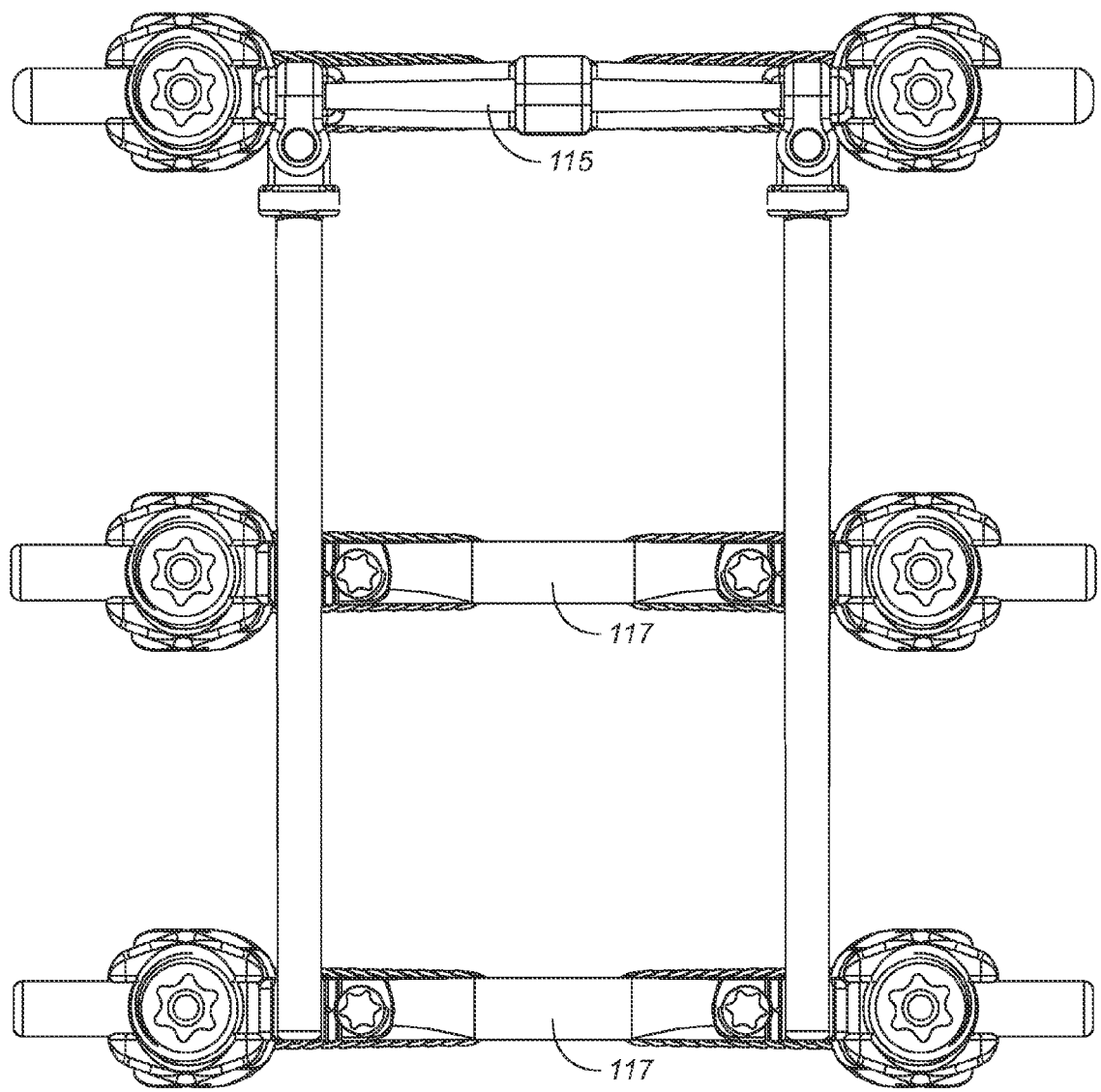

With respect to FIG. 45, to ease the transition to a one level fused area of the spine this two level system can be modified by replacing the horizontal rod 622 with a horizontal rod 115 (FIGS. 45A, 45B), which is much like horizontal rod 104 with deflection or loading rods 118, 120 of FIG. 1. This embodiment is depicted in FIG. 45A. Thus, fusion is accomplished between the two lower horizontal rods 117 which rods are like those depicted in FIG. 34, or like horizontal rods 116 in FIG. 1, and made of, preferably, titanium, and flexibility is provided by the upper horizontal rod 115 that is like horizontal rod 114 with deflection or loading rods that are shown in FIG. 1. Accordingly, there is more gradual transition from a healthier portion of the spine located above horizontal rod 115 through horizontal rod 115 to the fused part of the spine located between horizontal rod 624 and horizontal rod 606 of FIG. 45 or between the horizontal rods 117 (FIG. 45A).

Method of Implantation and Revised Implantation

A method of implantation of the system in the spine of a human patient is as follows.

First the vertebral levels that are to receive the system are identified. Then the anchor systems are implanted, generally two anchor systems for each level. The anchor systems can be implanted using a cannula and under guidance imaging such as x-ray imaging. Alternatively, the anchor system can be implanted using traditional spinal surgery techniques. Then the horizontal rods are inserted and secured to the anchor systems. The horizontal rods can be inserted laterally through a cannula or with an incision and the use of, for example, a lead-in cone. Alternatively, the horizontal rods can be inserted using traditional techniques when the anchor systems are implanted. Thereafter, the vertical rods can be pivoted, rotated or placed into communication with and secured to the appropriate horizontal rod.

Should a dynamic stabilization system such as system 100 be initially implanted and then should there be a desire to make the system more rigid or to accomplish a fusion, the system 100 can be revised by removing the horizontal rod 104 that includes the deflection rods or loading rods and replace it with a horizontal rod 106 which has the vertical rod mounts (FIG. 34) and is thus substantially more rigid. Thus a revision to a fusion configuration can be accomplished with minimal trauma to the bone and tissue structures of the spine.

Materials of Embodiments of the Invention

In addition to Nitinol or nickel-titanium (NiTi) other super elastic materials include copper-zinc-aluminum and copper-aluminum-nickel. However for biocompatibility the nickel-titanium is the preferred material.

As desired, implant 100 can be made of titanium or stainless steel. Other suitable material includes by way of example only polyetheretherketone (PEEK), polyetherketoneketone (PEKK), polyetherketone (PEK), polyetherketoneetherketoneketone (PEKEKK), and polyetheretherketoneketone (PEEKK). Still, more specifically, the material can be PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

As will be appreciated by those of skill in the art, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention.

Reference to appropriate polymers that can be used in the spacer can be made to the following documents. These documents include: PCT Publication WO 02/02158 A1, dated Jan.

10, 2002, entitled "Bio-Compatible Polymeric Materials;" PCT Publication WO 02/00275 A1, dated Jan. 3, 2002, entitled "Bio-Compatible Polymeric Materials;" and PCT Publication WO 02/00270 A1, dated Jan. 3, 2002, entitled "Bio-Compatible Polymeric Materials."

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A modular spine treatment kit comprising:
a plurality of anchor systems adapted to be anchored to the spine of a patient;
each of said anchors including a head and a bone anchor;
a plurality of first deflection horizontal rod systems wherein each deflection horizontal rod system includes a horizontal rod having a first end, a second end, and a mount extending from the horizontal rod substantially midway between the first end and the second end, a flexible deflection rod having a fixed end mounted to the mount of the horizontal rod and a deflectable end capable of deflecting relative to the horizontal rod in response to a load applied to the deflectable end;
at least one second horizontal rod that is rigid;
each of said anchor heads including a channel that can receive one of said first deflection horizontal rod systems and said second horizontal rod;
at least one vertical rod that can be connected between the at least one rigid second horizontal rod and a deflectable end of a flexible deflection rod of one of said plurality of first deflection horizontal rod systems; and
wherein the above components of the modular spine treatment kit can be selected and assembled in order to match the loading characteristics of the spine in order to dynamically stabilize the spine and share the load placed on the spine.

2. The kit of claim 1 wherein the horizontal rod of each of said plurality of first deflection horizontal rod systems is substantially rigid.

3. The kit of claim 1 wherein the flexible deflection rod of each of said plurality of first deflection horizontal rod systems is cantilever mounted to the mount of the horizontal rod of the deflection rod system.

4. The kit of claim 1 wherein:
the flexible deflection rod of each of said plurality of first deflection horizontal rod systems is made of a superelastic material; and
the horizontal rod of each of said plurality of first deflection horizontal rod systems is made of one of titanium and stainless steel.

5. The kit of claim 1 wherein:
the flexible deflection rod of each of said plurality of first deflection horizontal rod systems is made of an alloy of nickel and titanium; and
the horizontal rod of each of said plurality of first deflection horizontal rod systems is made of one of titanium and stainless steel.

6. The kit of claim 1 wherein the load placed on the first deflection rod system is carried along a deflection rod that is mounted to a horizontal rod of the first deflection rod system.

7. The kit of claim 1 wherein said plurality of said first deflection horizontal rod systems includes deflection horizontal rod systems having deflection rods having different degrees of flexibility.

8. The kit of claim 1 with several second rigid horizontal rods that can be used to fuse a first level of the spine and with one of said first deflection horizontal rod systems used to provide a transition level between the fused level and the rest of the spine.

9. The kit of claim 1 including a cone shaped introduction tool that can be placed over at least the first deflection rod system to aid the introduction of the system between the bones and ligaments of the spine.

10. The kit of claim 1 including another vertical rod that can be connected between one of the first deflection horizontal rods and the at least one rigid second horizontal rod such that the spacing of the vertical rod and the another vertical rod can determine the resistance that the assembled components provide against lateral spine bending.

11. The kit of claim 1 wherein the flexible deflection rod of each of said plurality of first deflection horizontal rod systems is tapered.

12. The kit of claim 1, further comprising a joint for connecting the deflectable end of a flexible deflection rod to a vertical rod such that said vertical rod can rotate about and pivot relative to the flexible deflection rod.

13. A modular spine treatment kit comprising:
a plurality of anchor systems adapted to be anchored to the spine of a patient;
each of said anchors including a head and a bone anchor;
a first deflection horizontal rod system, which includes a first rigid horizontal rod having a first end, a second end, and a mount extending from the horizontal rod substantially midway between the first end and the second end, and a flexible deflection rod having a fixed end mounted to the mount of the first rigid horizontal rod and a deflectable end capable of deflecting relative to the first rigid horizontal rod in response to a load applied to the deflectable end;
a second horizontal rod that is rigid;
each of said anchor heads including a channel that can receive one of said first deflection horizontal rod system and said second horizontal rod;
at least one vertical rod that can be connected between the deflectable end of the flexible deflection rod of said first deflection horizontal rod system and the rigid second horizontal rod; and
wherein the above components of the modular spine treatment kit can be selected and assembled in order to match the loading characteristics of the spine in order to dynamically stabilize the spine and share the load placed on the spine.

14. The kit of claim 13 including another vertical rod that can be connected between the first deflection horizontal rod system and the rigid second horizontal rod such that the spacing of the vertical rod and the another vertical rod can determine the resistance that the assembled components provide against lateral spine bending.

15. The kit of claim 13 wherein:
the flexible deflection rod said first deflection horizontal rod system is made of a superelastic material; and
the first rigid horizontal rod of each of said first deflection horizontal rod system is made of one of titanium and stainless steel.

16. The kit of claim 13, wherein:
the flexible deflection rod of said first deflection horizontal rod system is made of an alloy of nickel and titanium; and
the first rigid horizontal rod of said first deflection horizontal rod system is made of one of titanium and stainless steel.

17. The kit of claim 13 wherein the flexible deflection rod is cantilever mounted to the mount of the first rigid horizontal rod such that a load placed on the first deflection rod system is carried along the cantilever mounted flexible deflection rod.

18. The kit of claim 13 wherein said flexible deflection rod is tapered.

19. The kit of claim 13, further comprising a joint for connecting the deflectable end of the deflection rod to the vertical rod such that said vertical rod can rotate about and pivot relative to said flexible deflection rod.

20. The kit of claim 13 including a cone shaped introduction tool that can be placed over the first deflection rod system to aid the introduction of the first deflection rod system between the bones and ligaments of the spine.

21. The kit of claim 13 with several second rigid horizontal rods which can be used to fuse a first level of the spine and with said first deflection horizontal rod system used to provide a transition level between the first level and adjacent levels of the spine.

22. A spine treatment kit comprising:
a plurality of anchor systems adapted to be anchored to the spine of a patient;
each of said anchor systems including an anchor head and a bone anchor;
a first deflection horizontal rod system, which includes a first horizontal rod having a first end, a second end, and a mount extending from the horizontal rod substantially midway between the first end and the second end, and a flexible deflection rod having a fixed end mounted to the mount of the first rigid horizontal rod and a deflectable end capable of deflecting relative to the first rigid horizontal rod in response to a load applied to the deflectable end, wherein the first horizontal rod is made of one of titanium and stainless steel and the flexible deflection rod is made of a superelastic material;
a second horizontal rod that is rigid;
each of said anchor heads including a channel that can receive one of said first deflection horizontal rod system and said second horizontal rod;
at least one vertical rod that can be connected between the deflectable end of the flexible deflection rod of said first deflection horizontal rod system and the rigid second horizontal rod; and
wherein the above components of the modular spine treatment kit can be selected and assembled in order to match the loading characteristics of the spine in order to dynamically stabilize the spine and share the load placed on the spine.

23. The spine treatment kit of claim 22, wherein the superelastic material is an alloy of nickel and titanium.

24. The spine treatment kit of claim 22, including a cone shaped introduction tool that can be placed over at the first deflection rod system to aid the introduction of the first deflection rod system between the bones and ligaments of the spine.

* * * * *